US011512356B2

(12) United States Patent
Byrnes et al.

(10) Patent No.: US 11,512,356 B2
(45) Date of Patent: Nov. 29, 2022

(54) SYSTEMS AND METHODS FOR PARTICLE MULTIPLEXING IN DROPLETS

(71) Applicant: Tokitae LLC, Bellevue, WA (US)

(72) Inventors: Samantha A. Byrnes, Seattle, WA (US); Kevin Paul Flood Nichols, Issaquah, WA (US); Bernhard Hans Weigl, Seattle, WA (US)

(73) Assignee: Tokitae LLC, Bellevue, WA (US)

( * ) Notice: Subject to any disclaimer, the term of this patent is extended or adjusted under 35 U.S.C. 154(b) by 410 days.

(21) Appl. No.: 16/184,397

(22) Filed: Nov. 8, 2018

(65) Prior Publication Data

US 2020/0149092 A1 May 14, 2020

(51) Int. Cl.
 *C12Q 1/689* (2018.01)
 *C12Q 1/6869* (2018.01)
 *G01N 21/64* (2006.01)

(52) U.S. Cl.
 CPC .......... *C12Q 1/689* (2013.01); *C12Q 1/6869* (2013.01); *G01N 21/6428* (2013.01); *C12Q 2600/158* (2013.01); *C12Q 2600/16* (2013.01); *G01N 2021/6439* (2013.01)

(58) Field of Classification Search
 CPC ....... C12Q 1/68; G01N 33/53; G01N 21/6428
 See application file for complete search history.

(56) References Cited

U.S. PATENT DOCUMENTS

| | | | |
|---|---|---|---|
| 8,470,586 B2 | 6/2013 | Wu et al. | |
| 9,017,948 B2 | 4/2015 | Agresti et al. | |
| 9,074,242 B2 | 7/2015 | Larson et al. | |
| 9,487,603 B2 | 11/2016 | Fonnum et al. | |
| 9,695,471 B2 | 7/2017 | Beechem et al. | |
| 9,724,692 B2 | 8/2017 | Chiou et al. | |
| 2005/0171434 A1 | 8/2005 | Madden et al. | |
| 2005/0221339 A1* | 10/2005 | Griffiths ................ | B01F 5/0647 435/6.11 |
| 2009/0186342 A1 | 7/2009 | Bruno et al. | |
| 2010/0015595 A1* | 1/2010 | Siegel .................. | G01N 33/555 435/5 |
| 2011/0218123 A1 | 9/2011 | Weitz et al. | |
| 2016/0244809 A1 | 8/2016 | Belgrader et al. | |

FOREIGN PATENT DOCUMENTS

| | | | | |
|---|---|---|---|---|
| KR | 1020180043068 A | 4/2018 | | |
| WO | WO 2014/210353 A2 | 12/2014 | | |
| WO | WO-2014210353 A2 * | 12/2014 | ........... | C12Q 1/6869 |
| WO | 2018140966 A1 | 8/2018 | | |

OTHER PUBLICATIONS

Han et al. Quantum-dot-tagged microbeads for multiplexed optical coding of biomolecules. Nature Biotechnology; 2001; 19; 631-635. (Year: 2001).*
Han et al. Nature Biotechnology; 2001; 19; 631-635. (Year: 2001).*
Kim et al., Multiplex real-time PCR using temperature sensitive primer-supplying hydrogel particles and its application for malaria species identification. Plos One (Jan. 2018) (Year: 2018).*
PCT International Search Report; International App. No. PCT/US2019/060227; dated Apr. 10, 2020; pp. 1-6.
Byrnes et al.; Polydisperse emulsion digital assay to enhance time to detection and extend dynamic range in bacterialn cultures enabled by a statistical framework; Analyst; Jan. 5, 2018; pp. 2828-2836; vol. 143; The Royal Society of Chemistry.
Cao et al.; Molecular Beacon Aptamers for Protein Monitoring in Real-Time and in Homogeneous Solutions; Current Proteomics; Jun. 17, 2004; pp. 31-40; vol. 2, No. 1; Bentham Science Publishers Ltd.
Crawford et al.; Peptide aptamers: Tools for biology and drug discovery; Briefings in Functional Genomics and Proteomics: Apr. 2003; pp. 72-79; vol. 2, No. 1; Henry Stewart Publications.
Du et al.; SlipChip; National Institutes of Health; Aug. 21, 2009; pp. 1-14; vol. 9, No. 16; The Royal Society of Chemistry.
Ahmed Enas M.; Hydrogel: Preparation, characterization, and applications: A review; Journal of Advanced Research; Jul. 18, 2013; pp. 105-121; vol. 6; Elsevier B.V.
Gao et al.; MVP: a microbe-phage interaction database; Nucleic Acids Research; Nov. 21, 2017; pp. D700-D707; vol. 46; Oxford University Press.
Greenwood et al.; Proximity assays for sensitive quantification of proteins; Biomolecular Detection and Quantification; May 20, 2015; pp. 10-16; vol. 4; Elsevier GmbH.
Gu et al.; Droplets Formation and Merging in Two-Phase Flow Microfluidics; International Journal of Molecular Sciences; Apr. 15, 2011; pp. 2572-2597; vol. 12; The authors.
Gullberg et al.; Cytokine detection by antibody-based proximity ligation; PNAS; Jun. 1, 2004; pp. 8420-8424; vol. 101, No. 22; The National Academy of Sciences of the USA.
Kaminski et al.; Droplet microfluidics for microbiology: techniques, applications and challenges; Lab on a Chip; May 6, 2016; pp. 2168-2187; vol. 16; The Royal Society of Chemistry.
Russell et al.; PhagesDB: the actinobacteriophage database; Bioinformatics; Dec. 6, 2016; pp. 784-786; vol. 33, No. 5; Oxford University Press.

(Continued)

*Primary Examiner* — Ethan C Whisenant
(74) *Attorney, Agent, or Firm* — AEON Law, PLLC; Adam L. K. Philipp; Shan Liao

(57) ABSTRACT

Described herein are systems and methods for multiplexed analysis of two or more targets in a test sample including a first set of particles including a first set of target-specific reagents and a first optically detectable identifier capable of emitting a first wavelength indicative of a first target, and at least one second set of particles including a second set of target-specific reagents and a second optically detectable identifier capable of emitting a second wavelength indicative of a second target; and at least one optically detectable reporter probe capable of constitutively emitting a third wavelength in response to reaction of the first set of target-specific reagents with the first target in the test sample and/or reaction of the second set of target-specific reagents with the second target in the test sample, wherein the first wavelength, the second wavelength, and the third wavelength are optically discernable from one another.

5 Claims, 12 Drawing Sheets

(56) References Cited

OTHER PUBLICATIONS

Smartt et al.; Bacteriophage reporter technology for sensing and detecting microbial targets; Analytical and Bioanalytical Chemistry; Dec. 2010; pp. 991-1007; Springer.
Grace X.Y. Zheng, et al.; "Massively Parallel Digital Transcriptional Profiling of Single Cells"; Nature Communications; Jan. 16, 2017; pp. 1-12 www.nature.com/naturecommunications.
Bian et al., "Quantum-Dot-Encapsulated Core-Shell Barcode Particles from Droplet Microfluidics", Journal of Materials Chemistry B, vol. 6, Epub. Jul. 19, 2018, pp. 7257-7262.
Kim et al., "Multiplex Real-Time PCR Using Temperature Sensitive Primer-Supplying Hydrogel Particles and Its Application for Malaria Species Identification", PLOS One, vol. 13, No. 1, Jan. 2, 2018, pp. 1-12.
Extended European Search Report and Search Opinion for European Patent Application No. 19882404.7 dated Jul. 8, 2022, 7 pages.

\* cited by examiner

FIG. 1
100 System for Multiplexed Analysis of Two or More Targets in a Test Sample
105 Two or More Sets of Particles
110 First Set of Particles
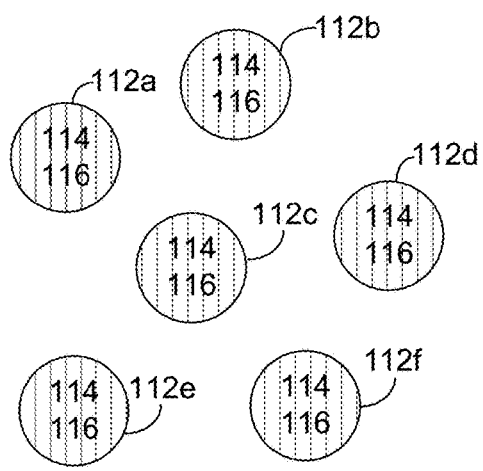
120 At least One Second Set of Particles
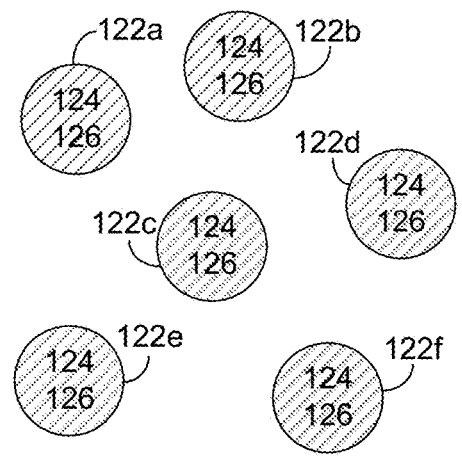
130 At least One Optically Detectable Reporter Probe
132
134

FIG. 3
300 System for Multiplexed Detection of Two or More Nucleic Acid Sequences in a Test Sample
305 Two or More Sets of Particles
310 First Set of Particles
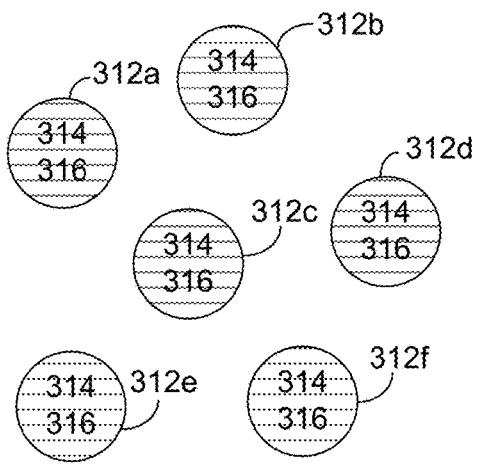
320 At least One Second Set of Particles
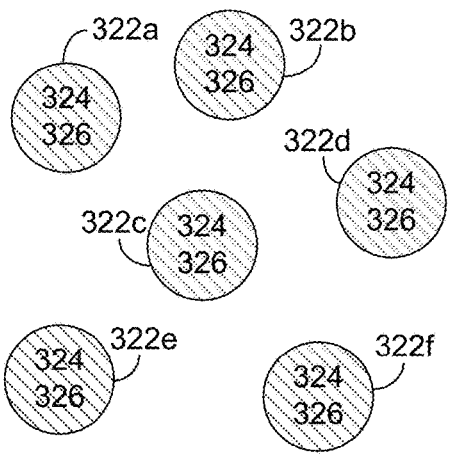
330 At least One Optically Detectable Reporter Probe
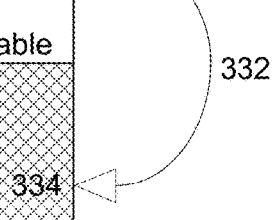

FIG. 4
400 System for Multiplexed Detection of Two or More Bacterial Nucleic Acid Sequences in a Test Sample
405 Two or More Sets of Particles
410 First Set of Particles
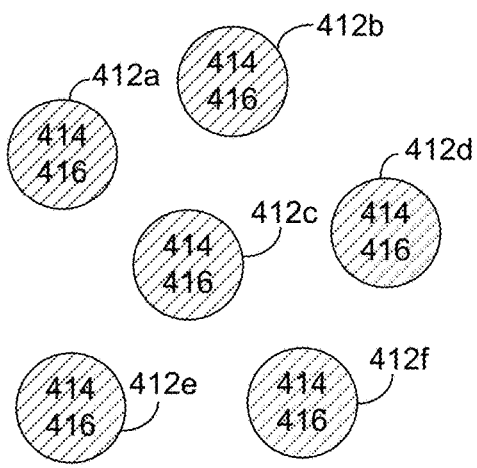
412a, 412b, 412c, 412d, 412e, 412f
414 416
420 At least One Second Set of Particles
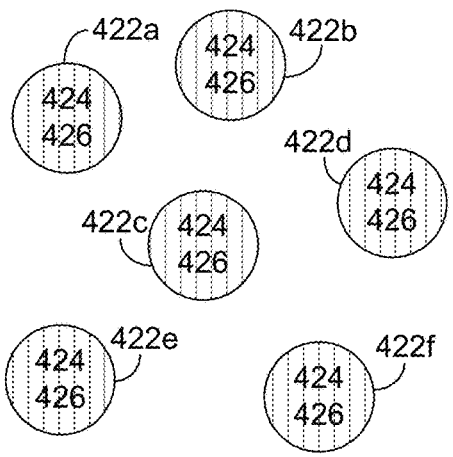
422a, 422b, 422c, 422d, 422e, 422f
424 426
430 At Least One Fluorescent Intercalating Agent
432
434

FIG. 5
500  System for Multiplexed Analysis of Antibiotic Resistance in a Bacterial Sample
505  Two or More Sets of Particles
510  First Set of Particles
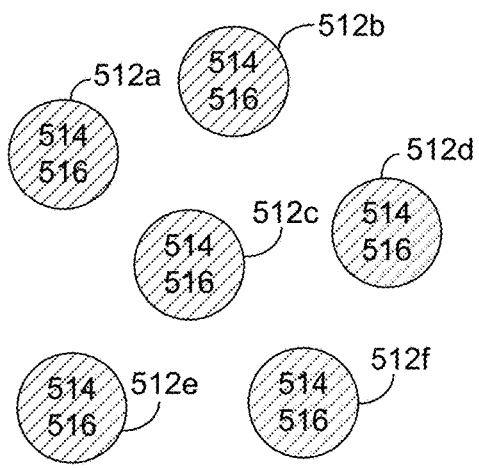
520  At least One Second Set of Particles
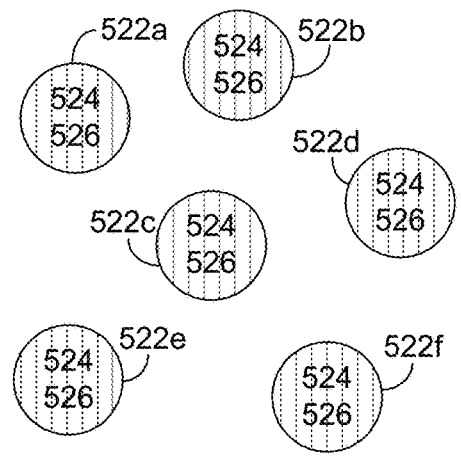
530  At least One Optically Detectable Reporter Probe

FIG. 6
600 System for Multiplexed Analysis of Two or More Antigens in a Test Sample
605 Two or More Sets of Particles
610 First Set of Particles
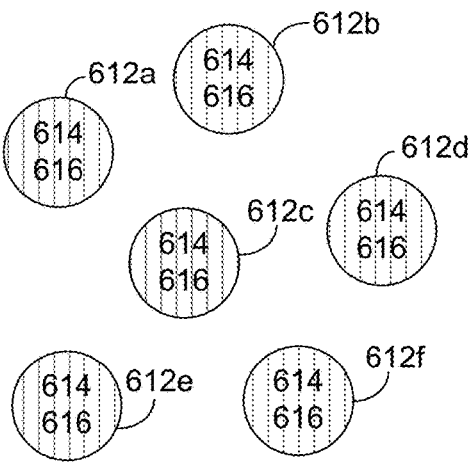
620 At least One Second Set of Particles
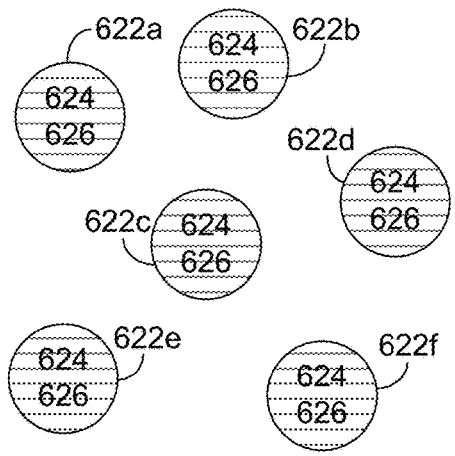
630 At least One Optically Detectable Reporter Probe
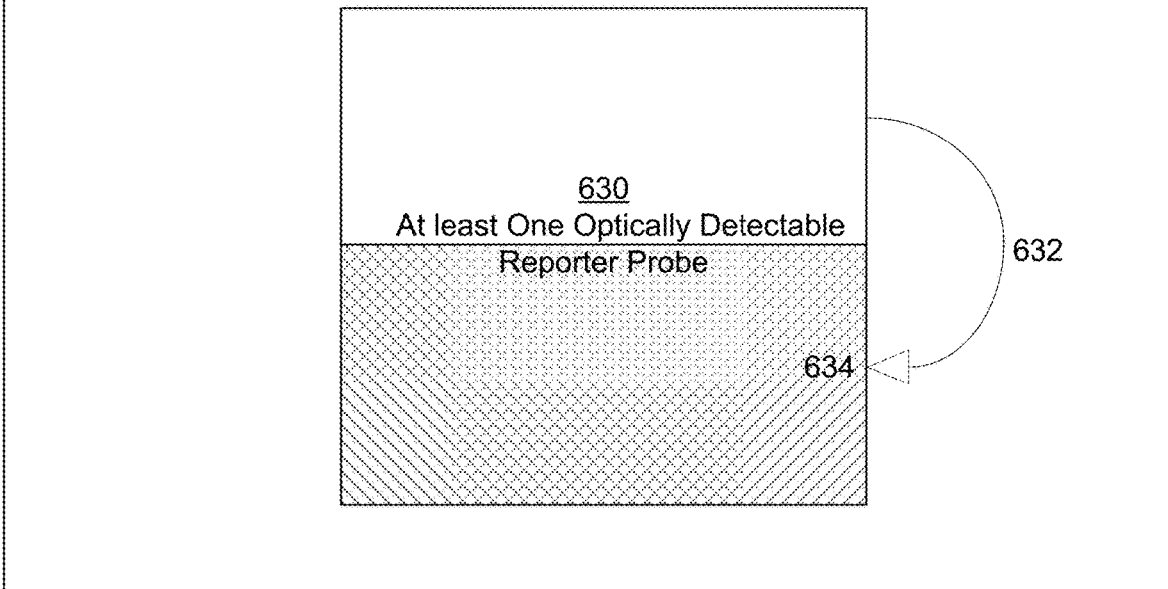

FIG. 7

700    A method for multiplexed analysis of two or more targets in a test sample 710    Combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first set of one or more target-specific reagents specific for a first target and a first optically detectable identifier capable of emitting a first wavelength indicative of the first set of one or more target-specific reagents, wherein each particle of the at least one second set of particles is degradable in response to a second environmental condition and has associated therewith a second set of one or more target-specific reagents specific for a second target and a second optically detectable identifier emitting a second wavelength indicative of the second set of one or more target-specific reagents, and wherein the at least one optically detectable reporter probe constitutively emits a third wavelength in response to reaction of the first set of one or more target-specific reagents with the first target in the test sample and/or to reaction of the second set of one or more target-specific reagents with the second target in the test sample 720    Forming a plurality of reaction droplets by adding an immiscible carrier fluid to the aqueous medium 730    Performing a reaction with the plurality of formed reaction droplets 740    Interrogating at least a portion of the plurality of formed reaction droplets for emission of the first wavelength indicative of the first set of one or more target-specific reagents, the second wavelength indicative of the second set of one or more target-specific reagents, and the third wavelength indicative of constitutive emission from the at least one optically detectable reporter probe 750    Reporting a number of the formed reaction droplets emitting both the first wavelength and the third wavelength 760    Reporting a number of the formed reaction droplets emitting both the second wavelength and the third wavelength

FIG. 8

800 A method for multiplexed analysis of two or more nucleic acid sequences in a test sample 810 Combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first amplification primer set selected to interact with a first nucleic acid sequence and a first optically detectable identifier capable of emitting a first wavelength indicative of the first amplification primer set, wherein each particle of the at least one second set of particles is degradable in response to a second environmental condition and has associated therewith a second amplification primer set selected to interact with a second nucleic acid sequence and a second optically detectable identifier emitting a second wavelength indicative of the second amplification primer set, and wherein the at least one optically detectable reporter probe is capable of constitutively emitting a third wavelength in response to amplification of the first nucleic acid sequence and/or the second nucleic acid sequence 820 Forming a plurality of reaction droplets by adding an immiscible carrier fluid to the aqueous medium 830 Performing an amplifcation reaction with the plurality of formed reaction droplets 840 Interrogating at least a portion of the plurality of formed reaction droplets for emission of the first wavelength indicative of the first amplification primer set, the second wavelength indicative of the second amplification primer set, and the third wavelength indicative of constitutive emission from the at least one optically detectable reporter probe in response to amplification of the first and/or the second nucleic acid sequence in the formed reaction droplets 850 Reporting a number of the formed reaction droplets emitting both the first wavelength and the third wavelength 860 Reporting a number of the formed reaction droplets emitting both the second wavelength and the third wavelength

FIG. 9

900 A method for multiplexed analysis of antibiotic resistance in a bacterial sample 910 Combining in an aqueous medium the bacterial sample, one or more reaction reagents, a first set of particles, at least one second set of particles, and at least one optically detectable reporter probe, wherein each particle of the first set of particles is degradable in response to a first environmental condition and has associated therewith a first antibiotic having at least one of bactericidal or bacteriostatic activity against a first subset of bacteria and a first optically detectable identifier capable of emitting a first wavelength indicative of the first antibiotic, wherein each particle of the at least one second set of particles is degradable in response to a second environmental condition and has associated therewith a second antibiotic having at least one of bactericidal or bacteriostatic activity against a second subset of bacteria and a second optically detectable identifier capable of emitting a second wavelength indicative of the second antibiotic, and wherein the at least one optically detectable reporter probe is capable of constitutively emitting a third wavelength in response to viability of bacteria in the bacterial sample 920 Forming a plurality of reaction droplets by adding an immiscible carrier fluid to the aqueous medium 930 Performing a reaction with the plurality of formed reaction droplets 940 Interrogating at least a portion of the plurality of formed reaction droplets for emission of the first wavelength indicative of the first antibiotic, the second wavelength indicative of the second antibiotic, and the third wavelength indicative of constitutive emission from the at least one optically detectable reporter probe in response to viability of bacteria in the bacterial sample 950 Reporting a number of the formed reaction droplets emitting both the first wavelength and the third wavelength 960 Reporting a number of the formed reaction droplets emitting both the second wavelength and the third wavelength

FIG. 10

1000 A method for multiplexed analysis of two or more antigens in a test sample

1010 Combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first antibody set and a first optically detectable identifier capable of emitting a first wavelength, the first antibody set including two or more antibodies specific for proximal targets on a first antigen, the two or more antibodies of the first antibody set including modifications capable of interacting in an antibody-based proximity assay, and the first optically detectable identifier indicative of the first antibody set, wherein each particle of the second set of particles is degradable in response to a second environmental condition and has associated therewith a second antibody set and a second optically detectable identifier capable of emitting a second wavelength, the second antibody set including two or more antibodies specific for proximal targets on a second antigen, the two or more antibodies of the second antibody set including modifications capable of interacting in an antibody-based proximity assay, and the second optically detectable identifier indicative of the second antibody set, and wherein the at least one optically detectable reporter probe is capable of constitutively emitting a third wavelength in response to the two or more antibodies of the first antibody set binding to their proximal targets on the first antigen and/or the two or more antibodies of the second antibody set binding to their proximal targets on the second antigen

1020 Forming a plurality of reaction droplets by adding an immiscible carrier fluid to the aqueous medium

1030 Performing a reaction with the plurality of formed reaction droplets

1040 Interrogating at least a portion of the plurality of formed reaction droplets for emission of the first wavelength indicative of the first antibody set, the second wavelength indicative of the second antibody set, and the third wavelength indicative of constitutive emission from the at least one optically detectable reporter probe in response to the two or more antibodies of the first antibody set binding to their proximal targets on the first antigen and/or the two or more antibodies of the second antibody set binding to their proximal targets on the second antigen

1050 Reporting a number of the formed reaction droplets emitting both the first wavelength and the third wavelength

1060 Reporting a number of the formed reaction droplets emitting both the second wavelength and the third wavelength

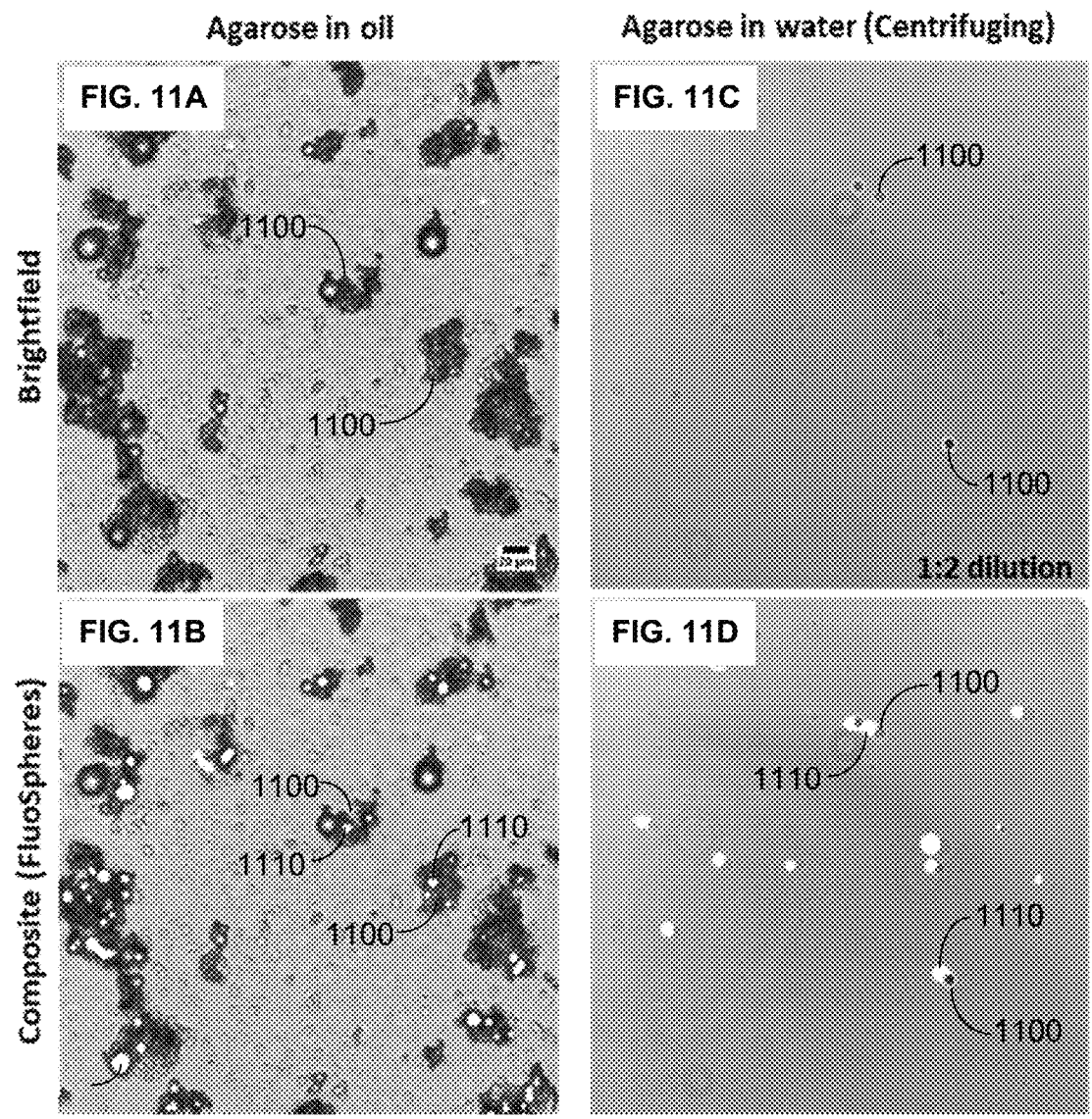

SYSTEMS AND METHODS FOR PARTICLE MULTIPLEXING IN DROPLETS

If an Application Data Sheet (ADS) has been filed on the filing date of this application, it is incorporated by reference herein. Any applications claimed on the ADS for priority under 35 U.S.C. §§ 119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC § 119(e) for provisional patent applications, for any and all parent, grandparent, great-grandparent, etc. applications of the Priority Application(s)).

PRIORITY APPLICATIONS

None

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a system for multiplexed detection of two or more nucleic acid sequences in a test sample includes, but is not limited to, two or more sets of particles including a first set of particles, each particle of the first set of particles degradable in response to a first environmental condition and having associated therewith a first amplification primer set and a first optically detectable identifier capable of emitting a first wavelength, the first amplification primer set selected to specifically interact with a first nucleic acid sequence, and the first optically detectable identifier indicative of the first amplification primer set; and at least one second set of particles, each particle of the at least one second set of particles degradable in response to a second environmental condition and having associated therewith a second amplification primer set and a second optically detectable identifier capable of emitting a second wavelength, the second amplification primer set selected to specifically interact with a second nucleic acid sequence, and the second optically detectable identifier indicative of the second amplification primer set; and at least one optically detectable reporter probe capable of constitutively emitting a third wavelength in response to amplification of the first nucleic acid sequence in the test sample and/or the second nucleic acid sequence in the test sample. In addition to the foregoing, other system aspects are described in the claims, drawings, and text forming a part of the present disclosure.

In an aspect, a system for multiplexed analysis of two or more targets in a test sample includes, but is not limited to, two or more sets of particles including a first set of particles, each particle of the first set of particles degradable in response to a first environmental condition and having associated therewith a first set of one or more target-specific reagents and a first optically detectable identifier capable of emitting a first wavelength, the first set of one or more target-specific reagents selected to specifically interact with a first target, and the first optically detectable identifier indicative of the first set of one or more target-specific reagents; and at least one second set of particles, each particle of the at least one second set of particles degradable in response to a second environmental condition and having associated therewith a second set of one or more target-specific reagents and a second optically detectable identifier capable of emitting a second wavelength, the second set of one or more target-specific reagents selected to specifically interact with a second target, and the second optically detectable identifier indicative of the second set of one or more target-specific reagents; and at least one optically detectable reporter probe capable of constitutively emitting a third wavelength in response to a reaction of the first set of one or more target-specific reagents with the first target in the test sample and/or a reaction of the second set of one or more target-specific reagents with the second target in the test sample.

In an aspect, a system for multiplexed detection of two or more bacterial nucleic acid sequences in a test sample includes, but is not limited to, two or more sets of particles including a first set of particles, each particle of the first set of particles degradable in response to a first temperature condition and having associated therewith a first amplification primer set and a first fluorescent identifier capable of emitting at a first wavelength, the first amplification primer set selected to specifically interact with a first bacterial nucleic acid sequence, and the first fluorescent identifier indicative of the first amplification primer set; at least one second set of particles, each particle of the at least one second set of particles degradable in response to a second temperature condition and having associated therewith a second amplification primer set and a second fluorescent identifier capable of emitting at a second wavelength, the second amplification primer set selected to specifically interact with a second bacterial nucleic acid sequence, and the second fluorescent identifier indicative of the second amplification primer set; and at least one fluorescent intercalating agent capable of constitutively emitting at a third wavelength in response to amplification of the first bacterial nucleic acid sequence in the test sample and/or the second bacterial nucleic acid sequence in the test sample.

In an aspect, a system for multiplexed analysis of antibiotic resistance in a bacterial sample includes, but is not limited to, two or more sets of particles including a first set of particles, each particle of the first set of particles degradable in response to a first environmental condition and having associated therewith a first antibiotic and a first optically detectable identifier capable of emitting a first wavelength, the first antibiotic having at least one of bactericidal or bacteriostatic activity against a first subset of bacteria, and the first optically detectable identifier indicative of the first antibiotic; and at least one second set of particles, each particle of the at least one second set of particles degradable in response to a second environmental condition and having associated therewith a second antibiotic and a second optically detectable identifier capable of emitting a second wavelength, the second antibiotic having at least one of bactericidal or bacteriostatic activity against a second subset of bacteria, and the second optically detectable identifier indicative of the second antibiotic; and at least one optically detectable reporter probe capable of constitutively emitting a third wavelength in response to viability of bacteria in the bacterial sample. In addition to the foregoing, other system aspects are described in the claims, drawings, and text forming a part of the present disclosure.

In an aspect, a system for multiplexed analysis of two or more antigens in a test sample includes, but is not limited to, two or more sets of particles including a first set of particles, each particle of the first set of particles degradable in response to a first environmental condition and having associated therewith a first antibody set and a first optically detectable identifier capable of emitting a first wavelength, the first antibody set including two or more antibodies specific for proximal targets on a first antigen, wherein the two or more antibodies of the first antibody set include modifications capable of interacting in an antibody-based proximity assay, and the first optically detectable identifier indicative of the first antibody set; and at least one second set of particles, each particle of the at least one second set of particles degradable in response to a second environmental condition and having associated therewith a second antibody set and a second optically detectable identifier capable of emitting a second wavelength, the second antibody set including two or more antibodies specific for proximal targets on a second antigen, wherein the two or more second antibodies of the second antibody set include modifications capable of interacting in an antibody-based proximity assay, and the second optically detectable identifier indicative of the second antibody set; and at least one optically detectable reporter probe capable of constitutively emitting a third wavelength in response to the two or more antibodies of the first antibody set binding to their proximal targets on the first antigen and/or the two or more antibodies of the second antibody set binding to their proximal targets on the second antigen.

In an aspect, a method for multiplexed analysis of two or more targets in a test sample includes, but is not limited to, combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first set of one or more target-specific reagents specific for a first target and a first optically detectable identifier capable of emitting a first wavelength indicative of the first set of one or more target-specific reagents, wherein each particle of the at least one second set of particles is degradable in response to a second environmental condition and has associated therewith a second set of one or more target-specific reagents specific for a second target and a second optically detectable identifier emitting a second wavelength indicative of the second set of one or more target-specific reagents, and wherein the at least one optically detectable reporter probe constitutively emits a third wavelength in response to reaction of the first set of one or more target-specific reagents with the first target in the test sample and/or to reaction of the second set of one or more target-specific reagents with the second target in the test sample; forming a plurality of reaction droplets by adding an immiscible carrier fluid to the aqueous medium; performing a reaction with the plurality of formed reaction droplets; interrogating at least a portion of the plurality of formed reaction droplets for emission of the first wavelength indicative of the first set of one or more target-specific reagents, the second wavelength indicative of the second set of one or more target-specific reagents, and the third wavelength indicative of constitutive emission from the at least one optically detectable reporter probe; reporting a number of the formed reaction droplets emitting both the first wavelength and the third wavelength; and reporting a number of the formed reaction droplets emitting both the second wavelength and the third wavelength. In addition to the foregoing, other method aspects are described in the claims, drawings, and text forming a part of the present disclosure.

In an aspect, a method for multiplexed analysis of two or more nucleic acid sequence targets in a test sample includes, but is not limited to, combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first amplification primer set selected to react with a first nucleic acid sequence and a first optically detectable identifier capable of emitting a first wavelength indicative of the first amplification primer set, wherein each particle of the at least one second set of particles is degradable in response to a second environmental condition and has associated therewith a second amplification primer set selected to react with a second nucleic acid sequence and a second optically detectable identifier emitting a second wavelength indicative of the second amplification primer set, and wherein the at least one optically detectable reporter probe is capable of constitutively emitting a third wavelength in response to amplification of the first nucleic acid sequence and/or the second nucleic acid sequence; forming a plurality of reaction droplets by adding an immiscible carrier fluid to the aqueous medium; performing an amplification reaction with the plurality of formed reaction droplets; interrogating at least a portion of the plurality of formed reaction droplets for emission of the first wavelength indicative of the first amplification primer set, the second wavelength indicative of the second amplification primer set, and the third wavelength indicative of constitutive emission from the at least one optically detectable reporter probe in response to amplification of the first and/or the second nucleic acid sequence in the formed reaction droplets; reporting a number of the formed reaction droplets emitting both the first wavelength and the third wavelength; reporting a number of the formed reaction droplets emitting both the second wavelength and the third wavelength. In addition to the foregoing, other method aspects are described in the claims, drawings, and text forming a part of the present disclosure.

In an aspect, a method for multiplexed analysis of antibiotic resistance in a bacterial sample includes, but is not limited to, combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first antibiotic having at least one of bactericidal or bacteriostatic activity against a first subset of bacteria and a first optically detectable identifier capable of emitting a first wavelength indicative of the first antibiotic, wherein each particle of the at least one second set of particles is degradable in response to a second environmental condition and has associated therewith a second antibiotic having at least one of bactericidal or bacteriostatic activity against a second subset of bacteria and a second optically detectable identifier capable of emitting a second wavelength indicative of the second antibiotic, and wherein the at least one optically detectable reporter probe is capable of constitutively emitting a third wavelength in response to viability of bacteria in the bacterial sample; forming a plurality of reaction droplets by adding an immiscible carrier fluid to the aqueous medium; performing a reaction with the plurality of formed reaction droplets; interrogating at least a portion of the plurality of formed reaction droplets for emission of the first wavelength indicative of the first antibiotic, the second wavelength indicative of the second antibiotic, and the third wavelength indicative of constitutive emission from the at least one optically detectable reporter probe in response to viability of bacteria in the bacterial sample; reporting a number of the formed reaction droplets emitting both the first wavelength and the third wavelength; and reporting a number of the formed reaction droplets emitting both the second wavelength and the third wavelength. In addition to the foregoing, other method aspects are described in the claims, drawings, and text forming a part of the present disclosure.

In an aspect, a method for multiplexed analysis of two or more antigens in a test sample includes, but is not limited to combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first antibody set and a first optically detectable identifier capable of emitting a first wavelength, the first antibody set including two or more antibodies specific for proximal targets on a first antigen, the two or more antibodies of the first antibody set including modifications capable of interacting in an antibody-based proximity assay, and the first optically detectable identifier indicative of the first antibody set, wherein each particle of the second set of particles is degradable in response to a second environmental condition and has associated therewith a second antibody set and a second optically detectable identifier capable of emitting a second wavelength, the second antibody set including two or more antibodies specific for proximal targets on a second antigen, the two or more antibodies of the second antibody set including modifications capable of interacting in an antibody-based proximity assay, and the second optically detectable identifier indicative of the second antibody set, and wherein the at least one optically detectable reporter probe is capable of constitutively emitting a third wavelength in response to the two or more antibodies of the first antibody set binding to their proximal targets on the first antigen and/or the two or more antibodies of the second antibody set binding to their proximal targets on the second antigen; forming a plurality of reaction droplets by adding an immiscible carrier fluid to the aqueous medium; performing a reaction with the plurality of formed reaction droplets; interrogating at least a portion of the plurality of formed reaction droplets for emission of the first wavelength indicative of the first antibody set, the second wavelength indicative of the second antibody set, and the third wavelength indicative of constitutive emission from the at least one optically detectable reporter probe in response to the two or more antibodies of the first antibody set binding to the first antigen and/or the two or more antibodies of the second antibody set binding to the second antigen; reporting a number of the formed reaction droplets emitting both the first wavelength and the third wavelength; and reporting a number of the formed reaction droplets emitting both the second wavelength and the third wavelength.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1 is a schematic of a system for multiplexed analysis of two or more targets in a test sample including two or more sets of particles and at least one optically detectable reporter probe.

FIG. 3 is a schematic of a system for multiplexed analysis of two or more nucleic acid sequences in a test sample including two or more sets of particles and at least one optically detectable reporter probe.

FIG. 4 is a schematic of a system for multiplexed analysis of two or more bacterial nucleic acid sequences in a test sample including two or more sets of particles and at least one fluorescent intercalating agent.

FIG. 5 is a schematic of a system for multiplexed analysis of antibiotic resistance in a bacterial sample including two or more sets of particles and at least one optically detectable reporter probe.

FIG. 6 is a schematic of a system for multiplexed analysis of two or more antigens in a test sample including two or more sets of particles and at least one optically detectable reporter probe.

FIG. 7 is a block diagram of a method for multiplexed analysis of two or more targets in a test sample using a system such as shown in FIG. 1.

FIG. 8 is a block diagram of a method for multiplexed analysis of two or more nucleic acid sequences in a test sample using a system such as shown in FIG. 3.

FIG. 9 is a block diagram of a method for multiplexed analysis of antibiotic resistance in a bacterial sample using a system such as shown in FIG. 5.

FIG. 10 is a block diagram of a method for multiplexed analysis of two or more antigens in a test sample using a system such as shown in FIG. 6.

FIG. 11A shows a brightfield microscope image of formed agarose particles.

FIG. 11B shows a composite of a brightfield microscope image of FIG. 11A overlaid with a fluorescent image of the same field.

FIG. 11C shows a brightfield microscope image of formed agarose particles washed in water.

FIG. 11D shows a composite of the brightfield microscope image of FIG. 11C overlaid with a fluorescent image of the same field.

DETAILED DESCRIPTION

Figure 2:
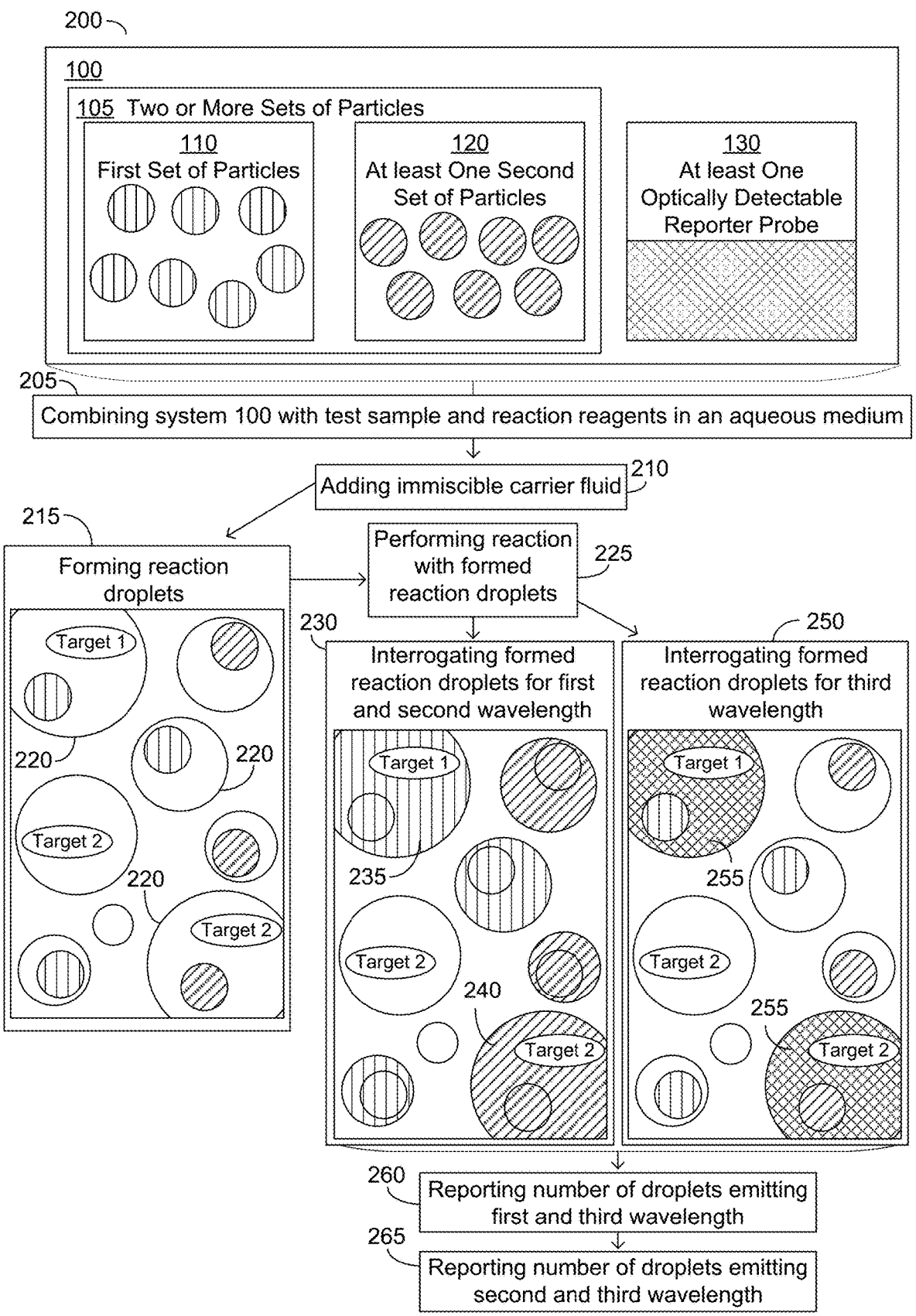
FIG. 2 illustrates a method for multiplexed analysis using a system such as shown in FIG. 1.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Described herein are systems and methods for multiplexed analysis of two or more targets in a sample using two or more sets of particles and a reporter probe. The two or more sets of particles and the reporter probe are designed for use in multiplexed reactions of a test sample in aqueous-in-oil reaction droplets. The particles include target-specific reagents (e.g., target-specific amplification primers) and an identifier matched to the target-specific reagents and hence a specific target (e.g., a specific target nucleic acid sequence) while the reporter probe is a constitutive reporter of a reaction type (e.g., amplification). The particles, reporter probe, test sample and other reaction reagents can be stochastically distributed into aqueous-in-oil reaction droplets and a reaction(s) performed. Each reaction droplet is assessed for a signal from the identifier (e.g., a first fluorescent color) matched to the target-specific reagents (and to the specific target) and a signal from the constitutive reporter of the reaction type (e.g., a second fluorescent color) indicating that a reaction has occurred (e.g., amplification). A reaction droplet emitting signals from both the identifier (e.g., a first fluorescent color) and the reporter probe (e.g., a second fluorescent color) indicates that the reaction with the specific target (e.g., amplification of a specific target nucleic acid sequence) has occurred. In this way, multiple targets can be assessed in a single multiplexed analysis.

With reference to FIG. 1, shown is a non-limiting example of a system for multiplexed analysis of two or more targets in a test sample which can serve as a context for one or more systems and/or methods described herein. System 100 includes two or more sets of particles 105 and at least one optically detectable reporter probe 130. The two or more sets of particles 105 include a first set of particles 110 and at least one second set of particles 120. Particles 112a, 112b, 112c, 112d, 112e, and 112f are representative of particles in the first set of particles 110 and are degradable in response to a first environmental condition. Each of the particles 112a-112f include a first set of one or more target-specific reagents 114 and a first optically detectable identifier 116. The first set of one or more target-specific reagents 114 are selected to specifically interact with a first target in the sample. The first optically detectable identifier 116 is capable of emitting a first wavelength (represented by the vertical lines) indicative of the first set of one or more target-specific reagents 114. The first optically detectable identifier 116 is further indicative of the first target to which the first set of one or more target-specific reagents 114 is capable of reacting with in a test sample. In general, the optically detectable identifier indicates that a particular set of one or more target-specific reagents are present in a given set of particles. In an aspect, the optically detectable identifier acts as a barcode for the set of one or more target-specific reagents and the specific target.

Particles 122a, 122b, 122c, 122d, 122e, and 122f are representative of particles in the second set of particles 120 and are degradable in response to a second environmental condition. In some embodiments, the second environmental condition is the same as the first environmental condition (e.g., the same temperature or pH condition). In some embodiments, the second environmental condition differs from the first environmental condition (e.g., differing temperature or pH conditions). Each of the particles 122a-122f include a second set of one or more target-specific reagents 124 and a second optically detectable identifier 126. The second set of one or more target-specific reagents 124 are selected to specifically interact with a second target in the sample. The second optically detectable identifier 126 is capable of emitting a second wavelength (represented by diagonal lines) indicative of the second set of one or more target-specific reagents 124. The second optically detectable identifier 126 is further indicative of the second target to which the second set of one or more target-specific reagents 124 is capable of reacting with in a test sample.

System 100 further includes at least one optically detectable reporter probe 130 capable of constitutively (as shown by arrow 132) emitting a third wavelength 134 (represented by the cross-hatched lines) in response to reaction of the first set of one or more target-specific reagents 114 with the first target in the sample and/or reaction of the second set of one or more target-specific reagents 124 with the second target in the sample. The optically detectable reporter probe constitutively emits that third wavelength in response to detecting a reaction. In some embodiments, the reaction detected by the optically detectable reporter probe only occurs if both the set of target-specific reagents and the relevant specific target are present in a given reaction droplet.

With reference to FIG. 2, shown is a non-limiting example of a method for multiplexed analysis of two or more targets in a test sample using two or more sets of particles and an optically detectable reporter probe such as described in the system of FIG. 1. Method 200 includes at step 205 combining the components of system 100 with a test sample and reaction reagents in an aqueous medium. System 100 includes two or more sets of particles 105 including a first set of particles 110 (represented by the circles with vertical lines) and at least one second set of particles 120 (represented by the circles with diagonal lines). System 100 further includes at least one optically detectable reporter probe 130. Method 200 includes at step 210 adding an immiscible carrier fluid (e.g., oil with surfactant) to the aqueous medium and at step 215 forming reaction droplets 220. Reaction droplets 220 are aqueous-in-oil droplets that can be formed by bulk emulsion (e.g., shaking or vortexing) or with a microfluidic device. The particles of the first set of particles 110, the particles of the at least one second set of particles 120, the optically detectable reporter probe 130, and any targets (shown as Target 1 and Target 2) within the test sample added at step 205 are stochastically distributed into the formed reaction droplets 220 at step 215. The reaction droplets 220 can be of mono-disperse or poly-disperse sizes. At step 225, method 200 includes performing a reaction with the formed reaction droplets 220 (e.g., an amplification reaction). Following completion of the reaction with the formed reaction droplets 220, method 200 includes at step 230 interrogating the formed reaction droplets 220 for a first wavelength 235 (depicted as vertical lines) indicative of the first set of one or more target-specific reagents associated with the first set of particles 110, a second wavelength 240 (depicted as diagonal lines) indicative of the second set of one or more target-specific reagents associated with the at least one second set of particles 120, and at step 250 interrogating the formed reaction droplets 220 for a third wavelength 255 (depicted as cross-hatching) constitutively emitted from the optically detectable reporter probe in response to at least one of the first set of target-specific reagents reacting with a first target (Target 1) in the test sample and/or the second set of target-specific reagents reactive with a second target (Target 2) in the test sample. Method 200 further includes at step 260 reporting a number of reaction droplets 220 emitting the first wavelength 235 and the third wavelength 255 and at step 265 reporting a number of reaction droplets 220 emitting the second wavelength 240 and the third wavelength 255. Reaction droplets emitting both the third wavelength and the first or second wavelength are indicative of the presence of the desired target (e.g., a specific nucleic acid sequence) and a generic reaction having been performed on/with the desired target (e.g., amplification).

Systems and methods are described herein for multiplexed analysis of two or more targets in a test sample. The two or more targets can include two or more specific targets in the test sample. The two or more targets can include two or more specific analytes in the test sample. In some embodiments, the two or more targets in the test sample include two or more nucleic acid sequences. For example, the two or more targets can include two or more specific DNA, RNA, or oligonucleotide sequences in a test sample. The two or more targets can include two or more specific cell types. For example, the two or more targets can include two or more types of bacteria or immune cells. The two or more targets can include two or more specific antigens.

The first set of one or more target-specific reagents is selected to specifically interact with a first target while the second set of one or more target-specific reagents is selected to specifically interact with a second target. For example, the one or more target specific reagents can include a sequence (e.g., a nuclei acid or amino acid sequence), a three dimensional structure, or an affinity that enables them to specifically interact with a target in a sample. In an aspect, the first set of one or more target-specific reagents is selected to specifically interact with a first nucleic acid sequence and the second set of one or more target-specific reagents selected to specifically interact with a second nucleic acid sequence. In some embodiments, the two or more targets in the test sample comprise two or more types of bacteria in a bacterial sample. For example, the two or more targets in the test sample can include two or more types of bacteria associated with sepsis or tuberculosis. In an aspect, the first set of one or more target-specific reagents is selected to specifically interact with a first subset of bacteria and the second set of one or more target-specific reagents is selected to specifically interact with a second subset of bacteria. In some embodiments, the two or more targets in the test sample include two or more binding targets. In some embodiments, the two or more targets in the test sample include two or more antigens in the test sample. For example, the two or more targets can include two or more antigens free in solution. For example, the two or more targets can include two or more antigens associated with one or more cell types, e.g., one or more types of immune or inflammatory cells. In an aspect, the first set of one or more target-specific reagents is selected to specifically interact with a first antigen and the second set of one or more target-specific reagents selected to specifically interact with a second antigen. In an aspect, each set of one or more target-specific reagents is selected to specifically interact with at least one protein, peptide, carbohydrate, lipid, or nucleic acid sequence. Other non-limiting examples of targets include antigens, receptors, cell surface markers, small molecule compounds, organic compounds, or inorganic compounds. In some embodiments, the two or more targets can include two or more targets (e.g., DNA, RNA, protein, carbohydrate, lipid, and the like) associated with a specific cell type(s) (e.g., blood, body fluid, or tissue cells, bacteria, fungi, parasites, plant cells, and the like).

Systems and methods are described herein for multiplexed analysis of two or more targets in a test sample. In an aspect, the test sample is a complicated or complex test sample, including many components (e.g., a biological sample such as blood or urine; or an environmental sample such as water from a well or other drinking water source). In an aspect, the test sample is a simple or defined test sample, including just two or more components. In an aspect, the test sample includes a bodily fluid (e.g., blood, urine, lymph, sputum, cerebrospinal fluid, semen, saliva, synovial fluid, mucus, amniotic fluid, vaginal secretions, breast milk, bile, aqueous humor, gastric acid, pus, phlegm, feces, or other bodily fluid or secretion), a tissue sample (e.g., a biopsy sample), or a swab sample (e.g., a swab sample taken from a surface of a body or body part). In some embodiments, the test sample includes an environmental sample (e.g., a sample of water, air, soil, plant, a surface, food, beverage, medicine, and the like). In an aspect, the test sample is a defined sample including a defined population of targets. For example, the test sample can be formulated to contain a defined number and set of targets for use in the multiplexed analysis.

System 100 includes two or more sets of particles 105 including a first set of particles 110 and at least one second set of particles 120, wherein each particle of the first set of particles 110 is degradable in response to a first environmental condition and each particle of the at least one second set of particles 120 is degradable in response to a second environmental condition. In an aspect, degradable in response to the first environmental condition and/or the second environmental condition comprises at least one of melt, liquefy, disperse, dissolve, decompose, disintegrate, break apart, deform, or change phase in response to the first environmental condition and/or the second environmental condition. In an aspect, degradable in response to the first environmental condition and/or the second environmental condition comprises at least partially melting, liquefying, dispersing, dissolving, decomposing, disintegrating, breaking apart, deforming, or changing phase in response to the first environmental condition and/or the second environmental condition. In some embodiments, each particle is capable of releasing or dispersing the set of one or more target-specific reagents and/or the optically detectable identifier in response to the environmental condition. In some embodiments, each particle degrades sufficiently to release or disperse the set of one or more target-specific reagents and/or the optically detectable identifier, but does not completely disintegrate. For example, the porosity of each particle may be altered in response to the environmental condition, allowing for release or dispersal of the target-specific reagents and/or the optically detectable identifier from the particle. For example, each particle can at least one of shrink or swell in response to an environmental condition.

In an aspect, the first environmental condition and the second environmental condition are identical environmental conditions. For example, the first environmental condition can be equivalent to or the same as the second environmental condition. For example, the particles in the first set of particles 110 and the particles in the at least one second set of particles 120 can degrade (e.g., melt, liquefy, disperse, dissolve, decompose, disintegrate, break apart, deform, or change phase) at the same temperature. In an aspect, the first environmental condition and the second environmental condition are different environmental conditions. For example, the particles in the first set of particles 110 can degrade at a first temperature and the particles in the at least one second set of particles 120 can degrade at a second temperature, wherein the first and second temperatures are different. In an aspect, the first environmental condition and the second environmental condition comprise at least one of temperature, pH, chemical reaction, electric field, or electromagnetic energy.

In an aspect, the particles of the first set of particles 110 and of the at least one second set of particles 120 include a structure formed from a degradable material that is degradable in response to at least the first environmental condition or the second environmental condition. In an aspect, each particle of the first set of particles 110 is formed from a first material that degrades in response to a first environmental condition and each particle of the at least one second set of particles 120 is formed from a second material that degrades in response to a second environmental condition. In an aspect, the particles of the first set of particles 110 and of the at least one second set of particles 120 are formed from the same material that degrades in response to the first environmental condition and/or the second environmental condition. In an aspect, each particle of the first set of particles 110 and the at least one second set of particles 120 is formed from a material that at least one of melts, liquefies, disperses, dissolves, decomposes, disintegrates, breaks apart, deforms, or changes phase in response to a first environmental condition and/or a second environmental condition. In some embodiments, each particle of the first set of particles 110 and the at least one second set of particles 120 is formed from a material that releases or disperses the set of one or more target-specific reagents and/or the optically detectable identifier in response to the environmental condition. In some embodiments, each particle of the first set of particles 110 and the at least one second set of particles 120 is formed from a material that degrades sufficiently to release or disperse the set of one or more target-specific reagents and/or the optically detectable identifier, but does not completely disintegrate. For example, the particles may be formed from a material (e.g., a hydrogel) which has increased porosity in response to an environmental condition, allowing for release or dispersal of the target-specific reagents and/or the optically detectable identifier from the particles. For example, the particles can be formed from a material that at least one of shrinks or swells in response to an environmental condition, allowing for release or dispersal of the target-specific reagents and/or the optically detectable identifier from the particles.

In some embodiments, system 100 can include more than two sets of particles, wherein each set of particles includes a unique set of target-specific reagents selected to interact with one of many potential targets in a test sample and a unique optically detectable identifier indicative of the one of many potential targets in the sample. In an aspect, the number of unique sets of particles range from three sets of particles to twenty sets of particles. In an aspect, system 100 includes three, four, five, six, seven, eight, nine, ten, eleven, twelve, thirteen, fourteen, fifteen, sixteen, seventeen, eighteen, nineteen, or twenty sets of particles, each set of particles including a set of one or more target-specific reagents and an optically detectable identifier.

In an aspect, system 100 includes at least one third set of particles, each particle of the at least one third set of particles degradable in response to at least one of the first, the second, or a third environmental condition and having associated therewith a third set of one or more target-specific reagents and a third optically detectable identifier capable of emitting a fourth wavelength, the third set of one or more target-specific reagents selected to specifically interact with a third target in the sample, and the third optically detectable identifier indicative of the third set of one or more target-specific reagents; and wherein the at least one optically detectable reporter probe is capable of constitutively emitting the third wavelength in response to at least the first set of one or more target-specific reagents reacting with the first target in the sample, the second set of one or more target-specific reagents reacting with the second target in the sample, and/or the third set of one or more target-specific reagents reacting with the third target, and wherein the first wavelength, the second wavelength, the third wavelength, and the fourth wavelength are optically discernable from one another.

In an aspect, the particles of the first set of particles 110 and of the at least one second set of particles 120 include a structure. For example, the particles of the first set of particles and of the at least one second set of particles can include a structure formed from a degradable material that is degradable in response to at least the first environmental condition or the second environmental condition. For example, the structure can include a micro- or nano-bead or particle formed from a solid or semi-solid degradable material. In an aspect, the structure is a bead or particle formed from a solid or semi-solid at least partially degradable material. In an aspect, the structure is spherical in shape, e.g., a microsphere. However, other non-spherical shapes are contemplated, e.g., irregular shape, cuboid, and the like. In an aspect, the particles range in size from about 0.1 micron to about 20 microns in diameter. For example, each particle can be about 0.1 micron, 0.2 micron, 0.5 micron, 0.75 micron, 1 micron, 2 micron, 3 micron, 4 micron, 5 micron, 6 micron, 7 micron, 8 micron, 9 micron, 10 micron, 11 micron, 12 micron, 13 micron, 14 micron, 15 micron, 16 micron, 17 micron, 18 micron, 19 micron, or 20 micron in diameter. In an aspect, each of the particles has a structure that is smaller than aqueous-in-oil reaction droplets formed with an immiscible carrier fluid and an aqueous medium containing the two or more sets of particles and the at least one optically detectable reporter probe.

In an aspect, the particles of the first set of particles 110 and of the at least one second set of particles 120 include a structure formed from a material that is stable in an aqueous environment. For example, each particle can be formed from a material that is stable in an aqueous medium including one or more reaction reagents (e.g., enzymes, ions, buffers, culture medium, and the like) for use in performing the multiplexed analysis. For example, each particle can be formed from a material that is stable in an aqueous environment until the contents of the particle, i.e., the set of one or more target-specific reagents and the at least one optically detectable identifier, are released in response to an environmental condition into a reaction droplet for performing the multiplex analysis.

In an aspect, the particles of the first set of particles 110 and of the at least one second set of particles 120 include a structure formed from a degradable gel. The degradable gel can include a colloidal network, polymer network, or solid jelly-like material with a three-dimensional cross-linked network capable of trapping and containing fluids. The network structure may result from physical bonds (e.g., ionic interactions, hydrogen bonds, or hydrophobic interactions) or chemical bonds (e.g., chemical cross-linking agents).

In an aspect, the particles of the first set of particles 110 and of the at least one second set of particles 120 include a structure formed from a degradable gel that is a hydrogel. The hydrogel can be a three-dimensional cross-linked network of natural and/or synthetic hydrophilic polymers with relatively high water content, e.g, up to or over 90% water. In an aspect, the particles are formed from an amorphous hydrogel, a semi-crystalline hydrogel, or a crystalline hydrogel. In an aspect, the particles are formed from a hydrogel formed by linking polymer chains via a chemical reaction, ionizing radiation, and/or physical interactions such as entanglements, electrostatics, or crystalline formation.

In an aspect, the particles of the first set of particles 110 and of the at least one second set of particles 120 include a structure formed from a neutral or nonionic hydrogel. In an aspect, the particles of the first set of particles 110 and of the at least one second set of particles 120 are formed from an ionic (anionic or cationic) hydrogel. In an aspect, the particles of the first set of particles 110 and of the at least one second set of particles 120 are formed from an amphoteric hydrogel containing both acidic and basic groups. In an aspect, the particles of the first set of particles 110 and of the at least one second set of particles 120 are formed from a zwitterionic hydrogel containing both anionic and cationic groups in repeating units.

In an aspect, the particles of the first set of particles 110 and of the at least one second set of particles 120 include a structure formed from a homopolymeric hydrogel having a polymeric network derived from a single species of monomer. In an aspect, each particle of the first set of particles 110 and of the at least one second set of particles 120 is formed from a copolymeric hydrogel having two or more different monomer species with at least one hydrophilic component and organized in random, block, or alternating configurations along the chain of the polymer network. In an aspect the hydrogel includes an interpenetrating polymer network formed from two independent cross-linked synthetic or natural polymer components. In an aspect, the hydrogel includes a semi-interpenetrating polymer network formed from one component that is a cross-linked polymer and another component that is a non-cross-linked polymer. In an aspect, the hydrogel includes a sequential interpenetrating or semi-interpenetrating polymer network. In an aspect, the superstructure of the particles is a hydrogel formed by bulk, solution, or suspension polymerization.

In an aspect, the particles of the first set of particles 110 and of the at least one second set of particles 120 include a structure formed from a natural hydrogel material. For example, the particles can be formed from natural polymers including proteins, non-limiting examples of which include collagen, gelatin, fibrin, or elastin. For example, the particles can be formed from natural polymers including polysaccharides such as chitosan, starch, alginate, and agarose. For example, the particles can include methylcellulose, hyaluronic acid, and other naturally derived polymers.

In an aspect, the particles of the first set of particles 110 and of the at least one second set of particles 120 include a structure formed from synthetic polymers. For example, the particles can be formed through chemical polymerization methods from one or more of polyethylene glycol (PEG), polyvinyl alcohol, sodium polyacrylate, acrylate polymers, acrylamide polymers, methacrylate, acrylonitrile, and derivatives, combinations, and/or salts thereof, and copolymers with an abundance of hydrophilic groups. Other non-limiting examples include PEG-diacylate (PED-DA), thiol and/or acrylate modified PEG, and azide and/or alkyne modified PEG.

In an aspect, the particles of the first set of particles 110 and of the at least one second set of particles 120 include a structure formed from a form of acrylamide. For example, the particles can be formed from polyacrylamide. For example, the particles can be formed from a polymer of N-isopropylacrylamide, non-limiting examples of which include poly(N-isopropylacrylamide) (pNIPA, pNIPAAm, pNIPAA or pNIPAm) thermosensitive polymer or copolymer-based hydrogels. Other non-limiting examples include poly(N-octyl acrylamide), poly(N-tert-butyl acrylamide), poly(N-phenyl acrylamide), and poly(N-sec-butyl acrylamide).

In an aspect, the particles of the first set of particles 110 and of the at least one second set of particles 120 include a structure formed from agarose. For example, the particles can be formed from repeating agarobiose units extracted from red seaweed. For example, particles can be formed from a linear polymer composed of a disaccharide of D-galactose and 3,6-anhydro-L-galactopyranose. For example, the particles can be formed from a linear galactan hydrocolloid isolated from agar or agar-bearing marine algae.

In an aspect, the particles of the first set of particles 110 and of the at least one second set of particles 120 include a structure formed from low melt agarose. In an aspect, each particle of the first set of particles and the at least one second set of particles is formed from a low melt agarose with a melting temperature of less than or equal to about 95° C. to less than or equal to about 45° C. For example, the low melt agarose can have a melting temperature of less than or equal to about 95° C., 90° C., 85° C., 80° C., 75° C., 70° C., 65° C., 60° C., 55° C., 50° C., or 45° C. In an aspect, each particle of the first set of particles and the at least one second set of particles is formed from a low melt agarose with a melting temperature less than or equal to about 65° C. (e.g., product number A9414 from Sigma-Aldrich Corp., St. Louis, Mo.). In an aspect, each particle of the first set of particles and the at least one second set of particles is formed from an ultralow melt agarose with a melting temperature less than or equal to about 50° C. (e.g., product number A5030 from Sigma-Aldrich Corp., St. Louis, Mo.).

In an aspect, the particles of the first set of particles 110 and of the at least one second set of particles 120 include a structure formed from a degradable alginate. In an aspect, the alginate is used in the form of a hydrogel. In an aspect, the alginate is formed from some combination of (1,4)-linked β-D-mannuronate (M) and α-L-guluronate (G) residues. The alginate can include linear copolymers containing blocks of M and G residues, for example blocks of consecutive G residues, blocks of consecutive M residues, and blocks of alternating M and G residues. In an aspect, percentage of G blocks dictates the physical properties of the resultant hydrogel. For example, alginate with a higher percentage of G blocks may have a relatively high stiffness. In an aspect, the M/G ratio dictates the physical properties of the resultant hydrogel. In an aspect, sequence, G-block length, and/or molecular weight dictate physical properties of the resultant hydrogel. In an aspect, the alginate includes a mixture of high and low molecular weight alginate polymers. In an aspect, the alginate is sourced from brown algae Phaeophyceae including, but not limited to *Laminaria hyperborea, Laminaria digitate, Laminaria japonica, Ascophyllum nodosum*, and *Macrocystis pyrifera*. In an aspect, the alginate is sourced from bacterial biosynthesis. For example, bacterial alginate can be produced via biosynthesis from *Azotobacter* or *Pseudomonas* bacteria. In an aspect, each particle of the first set of particles and the at least one second set of particles is formed from an alginate salt. For example, the alginate salt can include sodium alginate, potassium alginate, calcium alginate, or a combination thereof.

In an aspect, the particles of the first set of particles 110 and of the at least one second set of particles 120 include a structure formed from a derivative of alginate. For example, particles can be formed from an alginate material to which other elements have been added. In some embodiments, each particle of the first set of particles and the at least one second set of particles is formed by adding hydrophobic moieties to the alginate backbone. For example, amphiphilic alginate derivatives can be formed by adding long alkyl chains (e.g., dodecyl, octadecyl) to the alginate backbone. Other elements that could be added to the alginate backbone to generate amphiphilic alginate include, but are not limited to, dodecylamine, cholesterol, poly(ε-caprolactone), and poly(butyl) methacrylate. In some embodiments, the particles can include cell-interactive alginate to which cell-adhesive peptides have been chemically added as side-chains to the alginate backbone. For example, the alginate backbone can be modified with peptides including an arginine-glycine-aspartic acid (RGD) sequence.

In an aspect, the particles of the first set of particles 110 and of the at least one second set of particles 120 include a structure formed by ionically crosslinking an aqueous alginate solution. In some embodiments, the aqueous alginate solution is cross-linked with an ionic cross-linking agent. For example, an aqueous alginate solution can be cross-linked using a divalent or bivalent cation (e.g., $Ca^{2+}$, $Mg^{2+}$, $Fe^{2+}$, or $Ni^{2+}$). For example, an aqueous alginate solution can be cross-linked using calcium chloride ($CaCl_2$)). Other non-limiting examples of ionic cross-linking agents for crosslinking alginate include calcium sulfate and/or calcium carbonate.

In an aspect, the particles of the first set of particles 110 and of the at least one second set of particles 120 include a structure formed by covalently cross-linking the alginate. In some embodiments, the alginate is cross-linked with a covalent cross-linking agent. For example, the alginate can be cross-linked with poly(acrylamide-co-hydrazide) or adipic acid dihydrazide. In some embodiments, the alginate is photo cross-linked. For example, alginate modified with methacrylate can be cross-linked by exposure to an argon ion laser. For example, a combination of photosensitive plyallylamine and alginate can be cross-linked in response to ultra violet radiation. In an aspect, each particle of the first set of particles and the at least one second set of particles is formed with alginate using a combination of an ionic cross-linking agent and a covalent cross-linking agent.

In an aspect, the particles of the first set of particles 110 and of the at least one second set of particles 120 is formed from alginate combined with thermo-sensitive copolymers by a thermal process. For example, alginate can be cross-linked by UV irradiation in the presence of N-isopropylacrylamide and poly(ethylene glycol)-co-poly(ε-caprolactone).

In an aspect, the particles of the first set of particles 110 and of the at least one second set of particles 120 include a structure formed from a phase-change material that works by absorbing and storing/releasing thermal energy. In an aspect, the phase-change material is an organic material, e.g., paraffin, carbohydrate, or lipid derived. In an aspect, the phase-change material is an inorganic material, e.g., salt hydrates.

In an aspect, the particles of the first set of particles 110 and of the at least one second set of particles 120 include a structure formed from a degradable sugar. In an aspect, the degradable sugar is a dissolvable sugar. In an aspect, the degradable sugar is a disaccharide. For example, the degradable sugar can be a form of trehalose dihydrate (α-D-glucopyranosyl, α-D-glucopyranoside). In an aspect, the degradable sugar is a polysaccharide (e.g., starch, cellulose, glycogen, chitin, callose, laminarin, chrysolaminarin, xylan, arabinoxylan, mannan, fucoidan, pectins, or galactomannan). In an aspect, the degradable sugar is an oligosaccharide (e.g., raffinose, maltodextrins, or cellodextrins).

In an aspect, the particles of the first set of particles 110 and of the at least one second set of particles 120 include a structure that includes a degradable coating. In an aspect, the particles are formed from a solid or semi-solid material and further coated with a degradable material. In an aspect, the set of one or more target-specific reagents and the optically detectable identifier are incorporated into and releasable from a degradable coating in response to an environmental condition or change in environmental condition, wherein the environmental condition includes at least one of temperature, pH, chemical reaction, enzymatic reaction, electrical field, or electromagnetic energy.

In an aspect, the particles of the first set of particles 110 and of the at least one second set of particles 120 include a structure formed from a solid matrix. For example, particles can be formed from a solid matrix, e.g., polystyrene, to which the set of one or more target-specific reagents and the optically detectable identifier are associated with. For example, the set of one or more target-specific reagents and the optically detectable identifier can be attached to the solid matrix. For example, the set of one or more target-specific reagents and the optically detectable identifier can be included in a coating formed around the surface of the solid matrix. In some aspects, the coating including the set of one or more target-specific reagents and the optically detectable identifier is degradable allowing release of the set of one or more target-specific reagents and the optically detectable identifier. In an aspect, each particle is formed from latex and includes a coating degradable in response to an environmental condition.

In an aspect, the set of one or more target-specific reagents and the optically detectable identifier are incorporated into the particles during the formation of the particles. For example, the set of one or more target-specific reagents and the optically detectable identifier can be incorporated into liquefied low melt agarose prior to gelling. In an aspect, the set of one or more target-specific reagents and the optically detectable identifier are incorporated into the particles after formation of the particles. For example, the set of one or more target-specific reagents and the optically detectable identifier can be soaked, infused, absorbed, adsorbed, diffused, or otherwise integrated into or onto previously formed particles. In an aspect, the set of one or more target-specific reagents and the optically detectable identifier are attached to the exterior of the particles. In an aspect, the set of one or more target-specific reagents and the optically detectable identifier are incorporated into a coating associated with the exterior of the particles.

In an aspect, the particles of the first set of particles 110 and the at least one second set of particles 120 are formed from a porous material. For example, particles can be formed from a porous material through which the set of one or more target-specific reagents, the optically detectable identifier, or a combination thereof can freely diffuse from an internal reservoir of the particle. In an aspect, the particles of the first set of particles and of the at least one second set of particles are hollow microspheres, the center of which forms a reservoir for the set of one or more target-specific reagents and the optically detectable identifier.

In an aspect, the particles of the first set of particles 110 and of the at least one second set of particles 120 include a structure formed from a degradable material that is degradable in response to at least the first environmental condition or the second environmental condition. In an aspect, each of the particles in each of the first set of particles and the at least one second set of particles is formed from the same degradable material degradable in response to the same environmental condition, e.g., a specific temperature. In an aspect, each of the particles in the first set of particles is formed from a first degradable material degradable in response to a first environmental condition and each of the particles in the at least one second set of particles is formed from a second degradable material degradable in response to a second environmental condition, wherein the first degradable material differs from the second degradable material. In an aspect, the first degradable material and the second degradable material are degradable in response to at least one of temperature, pH, chemical reaction, electric field or electromagnetic energy.

In an aspect, the particles of the first set of particles 110 and of the at least one second set of particles 120 have a structure formed from a material capable of changing from a first phase or state to a second phase or state in response to a change in environmental condition or a stimulus. For example, the particles forming each of the two or more sets of particles can be formed from a material that changes from a solid or semi-solid state to a fluid state in response to a change in environmental condition or a stimulus. For example, the particles forming each of the two or more sets of particles can be formed from a material that changes from a fluid state to a solid or semi-solid state in response to a change in environmental condition or a stimulus. For example, the particles forming each of the two or more sets of particles can be formed from a material that changes phase or state in response to a change in temperature, a change in pH, a change in electric field, exposure to electromagnetic energy (e.g., light of a specific wavelength), a chemical (e.g., a chemical that cleaves a cross-linker of a polymer), an enzyme, and the like.

In an aspect, the particles of the first set of particles 110 and of the at least one second set of particles 120 include a structure formed from a temperature-responsive degradable material. For example, the particles forming each of the two or more sets of particles 105 can include a structure that at least one of degrades, melts, liquefies, disperses, dissolves, decomposes, disintegrates, breaks apart, deforms, or changes phase in response to increasing or decreasing temperature from a first temperature to a second temperature. In an aspect, the particles of the first set of particles 110 and of the at least one second set of particles 120 are degradable in response to increasing or decreasing a temperature from a first temperature to a second temperature by about 5° C. to about 100° C. In an aspect, the particles forming each of the two or more sets of particles 105 are formed from a material or materials that degrades in response to increasing or decreasing a temperature from a first temperature to a second temperature by about 5° C. to about 100° C. For example, each particle of the first set of particles and the at least one second set of particles is degradable in response to an increase or a decrease in temperature of at least about 5° C., at least about 10° C., at least about 15° C., at least about 20° C., at least about 25° C., at least about 30° C., at least about 35° C., at least about 40° C., at least about 45° C., at least about 50° C., at least about 55° C., at least about 60° C., at least about 65° C., at least about 70° C., at least about 75° C., at least about 80° C., at least about 85° C., at least about 90° C., at least about 95° C., or at least about 100° C., or any other temperature differential that allows the particles to degrade. As an example, the first set of particles and the second set of particles can be formed from heated agarose that forms a semi-solid gel upon cooling but can be re-liquefied in response to warming. Other non-limiting examples of temperature sensitive or responsive polymers include poly(N-isopropylacrylamide), poly(N-vinylcaprolactam), poly(lactic acid), poly(N-ethylacrylamide), poly(N-cyclopropymethacrylamide), poly(N-methyl-N-ethylacrylamide), poly(N-acryloylpyrrolidine), poly(N-ethylmethacrylamide), poly(N-cyclopropylacrylamide), poly(N-isopropylmethacrylamide), poly(N,N-diethylacrylamide), poly(N-n-propylmethacrylamide), poly(N-methyl-N-isopropylacrylamide), poly(N-methyl-N-isopropylacrylamide), poly(N-n-propylacrylamide), poly(N-methyl-N-n-propylacrylamide), poly(N-acryloylpiperidine), and the like.

In an aspect, the particles of the first set of particles 110 and of the at least one second set of particles 120 include a structure formed from a pH-responsive degradable material. For example, the particles forming each of the two or more sets of particles 105 can include a structure that at least one of degrades, melts, liquefies, disperses, dissolves, decomposes, disintegrates, breaks apart, deforms, or changes phase in response to increasing or decreasing the pH from a first pH to a second pH. In an aspect, particles of the first set of particles and the at least one second set of particles is degradable in response to increasing or decreasing the pH of the environment by about 0.5 pH units to about 14 pH units. In an aspect, particles forming each of the two or more sets of particles 105 are formed from a material or materials that degrades in response to increasing or decreasing the pH of the environment by about 0.5 pH units to about 14 pH units. For example, the particles of the first set of particles and of the at least one second set of particles are degradable in response to an increase or a decrease in pH units of at least about 0.5 pH units, of at least about 1 pH units, of at least about 3 pH units, of at least about 4 pH units, of at least about 5 pH units, of at least about 6 pH units, of at least about 8 pH units, of at least about 10 pH units, of at least about 12 pH units, or of at least about 14 pH units, or any other change in pH units that allows the particles to degrade. Non-limiting examples of gels or polymers that at least partially degrade in response to a change in pH include aminoalkyl methacrylate, poly(methacrylic acid-co-methyl methacrylate), hydroxypropyl-methylcellulose phthalate, hydroxypropyl-methylcellulose acetate succinate, poly(acrylate), poly(acetoacetoxyethyl methacrylate), poly[2-(diisopropylamino)ethyl methacrylate], poly(hexyl methacrylate), and poly[2-(dimethylamine)ethyl methacrylate).

In an aspect, the particles of the first set of particles 110 and of the at least one second set of particles 120 include a structure formed from a chemically-responsive degradable material. For example, the particles forming each of the two or more sets of particles 105 can include a structure that at least one of degrades, degrades, melts, liquefies, disperses, dissolves, decomposes, disintegrates, breaks apart, deforms, or changes phase in response to a chemical reaction. In an aspect, the chemical reaction includes a change in pH or ionic strength. For example, the particles can be formed from a pH-responsive material, examples of which have been described above. In an aspect, the chemical reaction includes cleaving a cross-linker. For example, the particles can be formed from a material with cleavable cross-linking. For example, the particles can include disulfide cross-linking degradable in response to reducing agents such as, for example, dithiothreitol. Other degradable links include anhydrides, imines, oximes, acetals, hydrazides, hydrazines, hydrazones. For example, the particles can include or be formed from degradable oligo/polymer segments such as, for example, chitin, chitosan, a polysaccharide, a peptide or protein, or polyesters. In an aspect, the particles are formed from a material degradable in response to an enzymatic reaction, e.g., in response to a protease or peptidase, a chitinase, or an amylase.

In an aspect, the particles of the first set of particles 110 and of the at least one second set of particles 120 include a structure formed from an electric field-responsive degradable material. For example, the particles forming each of the two or more sets of particles 105 can include a structure that at least one of degrades, degrades, melts, liquefies, disperses, dissolves, decomposes, disintegrates, breaks apart, deforms, or changes phase in response to application of an electric field. For example, the particles can be formed from a material that changes form, e.g., shrinks or swells, in response to application of an electric field. Non-limiting examples of electro-responsive polymers include poly(dimethylsiloxane), poly[2-(methacryloyloxy)ethyl phosphorylcholine], and poly(ethylenediamine-co-1, 10-bis(chloro-carbonyl)decane).

In an aspect, the particles of the first set of particles 110 and of the at least one second set of particles 120 include a structure formed from an electromagnetic energy-responsive degradable material. For example, the particles forming each of the two or more sets of particles 105 can include a structure that at least one of degrades, melts, liquefies, disperses, dissolves, decomposes, disintegrates, breaks apart, deforms, or changes phase in response to electromagnetic energy. For example, the particles can be formed from a photo-responsive material that changes properties when irradiated with ultraviolet or visible light of an appropriate wavelength. For example, the particles can be formed from polymers including photoactive groups, such as, for example, azobenzene, spirobenzopyran, triphenylmethane or cinnamonyl groups. Non-limiting examples of photo-responsive polymers include poly(N,N-dimethylacrylamide-co-4-phenyl-azophenyl acrylate) and poly(N,N-dimethylacrylamide-co-4-phenyl-azophenyl acrylamide).

In an aspect, the particles of the first set of particles 110 and of the at least one second set of particles 120 are hydrophilic. In an aspect, the particles of the first set of particles 110 and of the at least one second set of particles 120 include a structure at least partially formed from a hydrophilic material. In an aspect, the entirety of each particle is formed from a hydrophilic degradable material. In an aspect, the outer surface of each particle is formed from a hydrophilic degradable material. For example, the particles can be formed from hydrophilic polymer chains, e.g., a hydrogel, non-limiting examples of which have been described above herein. For example, the particles can be formed from a neutral hydrophilic polymer, a non-limiting example of which includes agarose. In an aspect, at least a portion of the particles of the first set of particles 110 and of the at least one second set of particles 120 are distributable into an aqueous portion of aqueous-in-oil droplets. For example at least a portion of the particles in the two or more sets of particles partition into the aqueous portion of aqueous-in-oil droplets.

Returning to FIG. 1, the first set of particles 110 includes a first set of one or more target-specific reagents 114 selected to specifically interact with a first target and the at least one second set of particles 120 includes a second set of one or more target-specific reagents 124 selected to specifically interact with a second target. For example, the one or more target-specific reagents are configured to, designed to, or capable of interaction with a target. For example, the one or more target specific reagents can include a sequence (e.g., a nuclei acid or amino acid sequence), a three dimensional structure, or an affinity that enables them to specifically interact with a target. In an aspect, the one or more target-specific reagents react with a target by binding to the target. For example, the one or more target-specific reagents can have a nucleic acid sequence or sequences selected to, capable of, or designed to bind or hybridize to a specific target, e.g., a nuclei acid sequence. For example, the one or more target-specific reagents can include complimentary nuclei acid sequences that at least partially hybridize to a corresponding target nucleic acid sequence. For example, the first set of one or more target-specific reagents can be selected to specifically interact with (e.g., bind to) or hybridize to a first nucleic acid sequence and the second set of one or more target-specific reagents can be selected to specifically interact with (e.g., bind to) or hybridize to a second nucleic acid sequence. For example, the one or more target-specific reagents can be configured, selected, or designed to bind to an epitope or similar structure on a specific target. For example, the one or more target-specific reagents can have an amino acid sequence or sequences and a corresponding configuration or three-dimensional structure capable of binding to an epitope or similar structure on a specific target. For example, the first set of one or more target-specific reagents can be configured, selected, or designed to specifically bind to a first antigen and the second set of one or more target-specific reagents can be configured, selected, or designed to specifically bind to a second antigen. For example, the one or more target-specific reagents can be configured, selected, or designed to bind into an active site of a specific target. For example, the one or more target-specific reagents can have a chemical composition and/or physical structure that confers a binding affinity for a specific target. For example, the one or more target-specific reagents can be configured, selected, or designed to bind to a receptor, e.g., a receptor on the surface of a cell. For example, the one or more target-specific reagents can serve as a catalyst or substrate or primer for a reaction. For example, the one or more target-specific reagents can include an agonist or antagonist of a cellular or biochemical reaction. For example, the one or more target-specific reagents can include an inhibitor of bacterial proliferation and/or growth.

In an aspect, the one or more target-specific reagents in the first set of one or more target-specific reagents 114 and in the second set of one or more target-specific reagents 124 are selected to interact with the surface of a specific cell type or types. For example, the one or more target-specific reagents are configured, selected, or designed to interact with (e.g., bind to) the surface of a specific cell type or types. For example, the one or more target-specific reagents are configured, selected, or designed to interact with (e.g., bind to) the surface of a specific cell type or types. In an aspect, the one or more target-specific reagents are selected to interact with (e.g., bind to) a specific biomolecule(s) associated with the surface of a microbe. For example, the target-specific reagents can be selected to specifically interact with biomolecules (e.g., proteins, lipids, carbohydrates, nucleic acids) on the surface of bacteria, a virus, a fungus, and/or a parasite. In an aspect, the one or more target-specific reagents are selected to specifically interact with biomolecules (e.g., proteins, lipids, carbohydrates, nucleic acids) associated with the surface of mammalian cells. The mammalian cells can be derived from a body fluid, swab, or excised tissue and can include, but not limited to, red blood cells, platelets, white blood cells, inflammatory cells, cancerous cells, normal tissue cells, tumor cells, and the like. In some embodiments, the multiplexed analysis includes one or more steps of lysing a cell or cells to allow interaction of the one or more target-specific reagents with biomolecules internal to the surface of the cell.

In an aspect, the one or more target-specific reagents in the first set of one or more target-specific reagents 114 and in the second set of one or more target-specific reagents 124 include oligonucleotides, antibodies, aptamers, or combinations thereof Other non-limiting examples of target-specific reagents includes antibody fragments, peptides, peptide nucleic acids, proteins, viruses, bacteriophage, phospholipids, carbohydrates, enzymes, substrates, receptors, lectins, peptide aptamers, inorganic molecules, organic molecules, small molecule agonists or antagonists, or combinations thereof.

In an aspect, the one or more target-specific reagents in the first set of one or more target-specific reagents 114 and in the second set of one or more target-specific reagents 124 include one or more oligonucleotides. The oligonucleotides can include DNA or RNA oligomers. For example, the one or more target-specific reagents can include one or more oligonucleotides having a sequence compatible with or capable of binding to and/or detecting a specific nucleic acid sequence. In an aspect, the one or more target-specific oligonucleotides include one or more oligonucleotide primers. The oligonucleotide primers can be RNA or DNA nucleotide sequences of 10 to 40 bases, wherein at least a portion of the nucleotide sequence is complimentary to a target nucleic acid sequence. In an aspect, the one or more target-specific reagents in the first set of target-specific reagents 114 and in the second set of target-specific reagents 124 comprise amplification primer sets. For example, the one or more target-specific oligonucleotides can include one or more primer sets for priming amplification of a specific nucleic acid sequence in a sample. For example, the first set of one or more target-specific reagents can include a first amplification primer set configured, selected, or designed to prime amplification of a first nucleic acid sequence and the second set of one or more target-specific reagents can include a second amplification primer set configured, selected, or designed to prime amplification of a second nucleic acid sequence.

In some embodiments, system 100 includes components capable of or designed for multiplexed detection of two or more nucleic acid sequences in a test sample. In some embodiments, system 100 includes the two or more sets of particles 105, wherein each particle 112a-112f of the first set of particles 110 includes a first set of one or more target-specific reagents 114 that is a first amplification primer set selected to specifically interact with a first nucleic acid sequence and each particle 122a-122f of the at least one second set of particles 120 includes a second set of one or more target-specific reagents 124 that is a second amplification primer set selected to specifically interact a second nucleic acid sequence. Each particle 112a-112f of the first set of particles 110 further includes a first optically detectable identifier 116 capable of emitting a first wavelength that is indicative of the first amplification primer set and each particle 122a-122f of the at least one second set of particles 120 further includes a second optically detectable identifier 126 capable of emitting a second wavelength that is indicative of the second amplification primer set. System 100 can further include at least one optically detectable reporter probe 130 capable of constitutively emitting a third wavelength in response to amplification of the first nucleic acid sequence in the test sample and/or the second nucleic acid sequence in the test sample.

In an aspect, the one or more target-specific reagents in the first set of one or more target-specific reagents 114 and in the second set of one or more target-specific reagents 124 comprise antibiotics. For example, the particles of the two or more sets of particles 105 can include one or more antibiotics or similar agents having at least one of bactericidal or bacteriostatic activity against bacteria or subsets of bacteria. For example, each set of particles can include an antibiotic or antibiotics with specificity for a particular bacteria or class of bacteria for assessing the types of bacteria in a test sample. Alternatively, antibiotics in the two or more sets of particles can be used for multiplexed analysis of antibiotic resistance against one or more subsets of bacteria. Non-limiting examples of antibiotics include aminoglycosides, ansamycins, carbapenems, cephalosporins, glycopeptides, lincosamides, macrolides, beta-lactams, monobactams, tetracyclines, sulfonamides, quinolones, penicillins, nitrofurans, and oxazolidinones.

In some embodiments, system 100 includes components capable of or designed for multiplexed analysis of antibiotic resistance in a bacterial sample. In an embodiment, system 100 includes two or more sets of particles 105, wherein each particle 112a-112f of the first set of particles 110 includes a first set of target-specific reagents 114 that includes a first antibiotic having bactericidal or bacteriostatic activity against a first subset of bacteria and each particle 122a-122f of the at least one second set of particles 120 includes a second set of target-specific reagents 124 that includes a second antibiotic having bactericidal or bacteriostatic activity against a second subset of bacteria. Each particle 112a-112f of the first set of particles 110 further includes a first optically detectable identifier 116 capable of emitting a first wavelength that is indicative of the first antibiotic and each particle 122a-112f of the at least one second set of particles 120 further includes a second optically detectable identifier 126 capable of emitting a second wavelength that is indicative of the second antibiotic. System 100 can further include at least one optically detectable reporter probe 130 capable of constitutively emitting a third wavelength in response to viability in the bacterial sample.

In an aspect, the one or more target-specific reagents in the first set of one or more target-specific reagents 114 and in the second set of one or more target-specific reagents 124 comprise one or more agonists or antagonists. For example, the one or more target-specific reagents can include one or more agonists or antagonists of a cellular function (e.g., proliferation, inflammatory response, enzymatic activity, ion flux). In some embodiments, each set of the two or more sets of particles includes one or more target-specific reagents that interact with the same target, e.g., a receptor or enzyme, but with varied affinity and activity, allowing for multiplexed analysis of the varied target-specific reagents against a particular biochemical reaction. For example, each set of particles can include a specific agonist or antagonist for use in multiplexed analysis of an array of agonists or antagonists against a particular biochemical reaction. In an aspect, the two or more sets of particles are designed for high-throughput/multiplexed analysis of antagonists and/or agonists against one or more targets.

In an aspect, the one or more target-specific reagents in the first set of one or more target-specific reagents 114 and in the second set of one or more target-specific reagents 124 comprise antibodies. An antibody that "specifically binds to" or is "specific for" a particular target or epitope on a particular target is one that binds to a particular target or epitope on a particular target without substantially binding to any other target or epitope. The term "antibody" is used here in its broadest sense and includes, but is not limited to, polyclonal antibodies, single monoclonal antibodies, antibody compositions with polyepitopic specificity, humanized antibodies, bispecific antibodies, heteroconjugate antibodies, single chain antibodies, and fragments of antibodies, among others. Fragments of antibodies comprising a portion of an intact antibody can include, but are not limited to, the antigen binding and/or variable region of the intact antibody. Non-limiting examples of antibody fragments include Fab, Fab', Fab$_2$, F(ab Fv, single-chain variable fragments (scFvs), diabody fragments (dimers of scFvs fragments), minibody fragments, (dimers of scFvs-C$_H$3 with linker amino acid), or the like. Methods for generating antibodies and fragments thereof are well known to the skilled artisan. Antibody fragments can be produced by modification of whole antibodies or synthesized do novo using recombinant DNA technologies.

In an aspect, the one or more target-specific reagent in the first set of one or more target-specific reagent 114 and in the second set of one or more target-specific reagents 124 comprises enzymes or enzyme substrates. Target-specific reagents that include an enzyme or enzymes can be configured, selected, or designed to interact with a substrate or substrates in the test sample. Target-specific reagents that include an enzyme or enzymes can be configured, selected, or designed to interact with agonists or antagonists in the test sample. For example, the system including the two or more sets of particles can be used for drug screening, e.g., screening for agonists or antagonists that modify an activity of an enzyme or enzymes. Target-specific reagents that include an enzyme substrate or substrates can be configured, selected, or designed to interact with enzymes in the test sample.

In an aspect, the one or more target-specific reagents in the first set of one or more target-specific reagents 114 and in the second set of one or more target-specific reagents 124 comprise aptamers. The aptamers can be oligonucleotide RNA- or DNA-based aptamers selected or designed with a sequence capable of recognizing and binding to one or more targets in the test sample. In an aspect, the one or more target-specific reagents in the first set of one or more target-specific reagents 114 and in the second set of one or more target-specific reagents 124 comprise peptide-based aptamers, an artificial protein in which inserted peptides are expressed as part of the primary sequence of a structurally stable protein and having binding affinities comparable to antibodies. See, e.g., Crawford, et al., *Brief Funct. Genomic Proteomic* 2:72-79, 2003, which is incorporated herein by reference. In an aspect, the one or more target-specific reagents in the first set of one or more target-specific reagents 114 and in the second set of one or more target-specific reagents 124 include novel peptides generated by a combinatorial approach and selected or designed to specifically recognize and bind a target.

In an aspect, the one or more target-specific reagents in the first set of one or more target-specific reagents 114 and in the second set of one or more target-specific reagents 124 include a ligand that specifically recognizes one or more microbes, e.g., bacteria. In an aspect, the target-specific reagent includes all or part of a pattern recognition receptor that recognizes microbe-specific molecules (e.g., bacterial carbohydrates, bacterial or viral DNA or RNA, bacterial peptides, peptidoglycans, lipoteichoic acids, N-formylmethionine, lipoproteins, and fungal glucans). Non-limiting examples of pattern recognition receptors with microbe-binding properties include toll-like receptors, C-type lectin receptors, NOD-like receptors, RIG-I-like receptors, RNA helicases, complement receptors, collectins, ficolins, pentraxins, C-reactive proteins, lipid transferases, and the like.

In an aspect, the one or more target-specific reagents in the first set of one or more target-specific reagents 114 and in the second set of one or more target-specific reagents 124 include a lectin. Lectins include carbohydrate-binding proteins that bind cell surface glycoproteins and/or glycolipids and can be derived from plant, animal, bacterial, fungal, or viral sources.

In an aspect, each of the first set of one or more target-specific reagents 114 and of the second set of one or more target-specific reagents 124 includes a set of binding elements modified for proximity signaling. For example, a set of target-specific reagents can include a first binding element configured, selected, or designed to bind a first target and a second binding element configured, selected, or designed to bind a second target, wherein the first target and the second target are proximal to one another and binding of the first binding element and the second binding element to their respective targets directly or indirectly results in an optically detectable signal. In some embodiments, the first target and the second target are on the same molecule, e.g., different epitopes on the same antigen. In some embodiments, the first target and the second target are on different molecules, e.g., epitopes on different antigens. Non-limiting examples of binding elements include oligonucleotides, antibodies, aptamers, peptides, proteins, ligands, and lectins. The binding elements can be further modified to provide proximity signaling. For example, the binding elements can be modified with oligonucleotides capable of priming amplification when in close proximity. For example, the binding elements can be modified with a donor-acceptor pair selected or designed to generate or shift a fluorescent signal when in close proximity.

In an aspect, each of the first set of one or more target-specific reagents 114 and of the second set of one or more target-specific reagents 124 includes a set of antibodies for antibody-based proximity signaling. For example, each set of one or more target specific reagents can include a set of antibodies which bind different epitopes on a target, e.g., a target protein. For example, each set of one or more target-specific reagents can include a set of antibodies which bind different targets (e.g., different receptors) on a cell surface (e.g., on the surface of an immune cell), wherein the targets are proximal to one another. In some embodiments, a first antibody of the set of antibodies is modified with a first molecule and a second antibody of the set of antibodies is modified with a second molecule, wherein when the first antibody and the second antibody bind to their respective proximal targets, the first molecule and the second molecule are able to interact. In some embodiments, the interaction of the first molecule and the second molecule directly or indirectly results in an optically detectable signal, e.g., fluorescence.

In some embodiments, system 100 includes components capable of or designed for multiplexed analysis of two or more antigens in a test sample. In an aspect, system 100 includes two or more sets of particles 105, wherein each particle 112a-112f of the first set of particles 110 includes a first set of target-specific reagents 114 that includes a first antibody set including two or more antibodies specific for proximal targets on a first antigen, the two or more antibodies of the first antibody set including modifications capable of interacting in an antibody-based proximity assay and each particle 122a-122f of the at least one second set of particles 120 includes a second set of target-specific reagents 124 that includes a second antibody set including two or more antibodies specific for proximal targets on a second antigen, the two or more antibodies of the second antibody set including modifications capable of interacting in an antibody-based proximity assay. Each particle 112a-112f of the first set of particles 110 further includes a first optically detectable identifier 116 capable of emitting a first wavelength that is indicative of the first antibody set and each particle 122a-112f of the at least one second set of particles 120 further includes a second optically detectable identifier 126 capable of emitting a second wavelength that is indicative of the second antibody set. System 100 can further include at least one optically detectable reporter probe 130 that is capable of constitutively emitting a third wavelength in response to the two or more antibodies of the first antibody set binding to their proximal targets on the first antigen and/or the two or more antibodies of the second antibody set binding to their proximal targets on the second antigen.

In an aspect, each of the first set of one or more target-specific reagents 114 and of the second set of one or more target-specific reagents 124 includes a set of antibodies modified with oligonucleotides. In some embodiments, a first antibody of the set of antibodies is modified with a first oligonucleotide and a second antibody of the set of antibodies is modified with a second oligonucleotide, wherein when the first antibody and the second antibody bind to their respective proximal targets, the first oligonucleotide and the second oligonucleotide are able to interact. For example, the first molecule and the second molecule associated with the antibodies can include oligonucleotides capable of at least partially hybridizing with one another when in proximity and form a template for amplification. For example, the first molecule and the second molecule associated with the antibodies can include oligonucleotides capable of being ligated to one another when in proximity and form a template for amplification.

In an aspect, each of the first set of one or more target-specific reagents 114 and of the second set of one or more target-specific reagents 124 includes a set of antibodies modified with a reporter-quencher pair. In some embodiments, a first antibody of the set of antibodies is modified with a reporter and a second antibody of the set of antibodies is modified with a quencher, wherein when the first antibody and the second antibody bind to their respective proximal targets, the reporter and the quencher interact. For example, a first antibody can include a fluorescent reporter and the second antibody can include a quencher and when the two antibodies bind to their respective proximal targets, the fluorescence associated with the fluorescent reporter is quenched. Non-limiting examples of reporter-quencher pairs are described below.

In an aspect, each of the first set of one or more target-specific reagents 114 and of the second set of one or more target-specific reagents 124 includes a set of antibodies modified with a donor-acceptor pair. In some embodiments, a first antibody of the set of antibodies is modified with a donor and a second antibody of the set of antibodies is modified with an acceptor, wherein when the first antibody and the second antibody bind to their respective proximal target, the donor and acceptor interact. For example, a first antibody can include a donor molecule that fluoresces at a first wavelength and the second antibody can include an acceptor that fluoresces at a second wavelength in response to the first wavelength emitted by the donor.

In an aspect, the one or more target-specific reagents in the first set of one or more target-specific reagents 114 and in the second set of one or more target-specific reagents 124 comprise bacteriophage. In an aspect, the target-specific reagent comprises a bacteriophage with a broad spectrum of bacterial infection. In an aspect, the target-specific reagent comprises a bacteriophage with a narrow spectrum of bacterial infection. Additional information regarding the breadth of bacteriophage can be found on various database websites, non-limiting examples of which include the Actinobacteriophage Database (Russell & Hatfull (2017) *Bioinformatics* 33:784-786) and the MVP database (Gao, et al. (2018) *Nucleic Acids Res.* 46:D700-D707), the references to which are incorporated herein.

System 100 further includes a first optically detectable identifier 116 associated with each of the first set of particles 110 and a second optically detectable identifier 126 associated with each of the at least one second set of particles 120. Each of the optically detectable identifiers is capable of emitting a wavelength (e.g., fluorescence of a specific wavelength and color) and is indicative of the set of one or more target-specific reagents associated with a given set of particles. Each of the optically detectable identifiers is further indicative of the specific target to which the set of one or more target-specific reagents is capable of reacting with. For example, a first optically detectable identifier capable of emitting a red wavelength of light may be indicative of a first set of one or more target-specific reagents and a first target in a test sample, while a second optically detectable identifier capable of emitting a green wavelength of light may be indicative of a second set of one or more target-specific reagents and a second target in the test sample. The optically detectable identifier acts as an optical indicator of which target-specific reagents is present in a given particle type. The optically detectable identifier is an optical bar code for a given set of one or more target-specific reagents specific for a given target. The optically detectable identifier can be at least one of a tag, a code, a label, an ID, or a marker indicative of the one or more target-specific reagents in a given particle type.

System 100 further includes at least one optically detectable reporter probe 130 capable of constitutively emitting a third wavelength. In an aspect, the first wavelength emitted by the first optically detectable identifier 116 is a first detectable color, the second wavelength emitted by the second optically detectable identifier 126 is a second detectable color, and the third wavelength constitutively emitted by the at least one optically detectable reporter probe 130 is a third detectable color. In an aspect, the first wavelength, the second wavelength, and the third wavelength are optically discernable from one another. In an aspect, the first wavelength, the second wavelength, and the third wavelength are optically distinguishable, distinct, or different from one another. As a non-limiting example, the first optically detectable identifier can emit a red color, the second optically detectable identifier can emit a green color, and the at least one optically detectable reporter probe can constitutively emit a blue color.

System 100 includes two or more sets of particles 105 including optically detectable identifiers capable of emitting a wavelength and at least one optically detectable reporter probe capable of constitutively emitting a wavelength. In an aspect, emitting a wavelength includes emitting a wavelength in response to temperature (incandescence), chemical reactions (chemiluminescence), biochemical reactions (bioluminescence), electrochemical reactions (electrochemiluminescence) or in response to absorbing light of other frequencies, e.g., fluorescence, phosphorescence, and Raman emission. In an aspect, emitting a wavelength includes a color of light leaving a surface, i.e., a wavelength or wavelengths reflected from a surface that is perceived as color of said surface.

In an aspect, the optically detectable identifiers 116 and 126 and the at least one optically detectable reporter probe 130 are capable of emitting a wavelength or wavelength band of electromagnetic radiation. In an aspect, the first wavelength, the second wavelength, or the third wavelength is an ultraviolet wavelength or wavelength band of electromagnetic energy. For example, the optically detectable identifiers and/or the at least one optically detectable reporter probe can be capable of emitting a wavelength or wavelength band in the range of about 100 nm to about 400 nm. In an aspect, at least one of the first wavelength, the second wavelength, or the third wavelength is a visible wavelength or wavelength band of electromagnetic energy. For example, the optically detectable identifiers and/or the at least one optically detectable reporter probe can be capable of emitting a wavelength or wavelength band in the range of about 390 nm to about 750 nm. In an aspect, the first wavelength, the second wavelength, or the third wavelength is a near infrared wavelength or wavelength band of electromagnetic energy. For example, the optically detectable identifiers and/or the at least one optically detectable reporter probe can be capable of emitting a wavelength or a wavelength band in the range of about 700 nm to about 2,500 nm). In an aspect, the emitted wavelength or wavelength band of electromagnetic radiation emitted from the optically detectable identifiers and/or the at least one optically detectable reporter probe includes radio waves, microwaves, X-rays, and gamma rays.

In an aspect, the first optically detectable identifier 116 is a first colored dye or pigment and the second optically detectable identifier 126 is a second colored dye or pigment. Non-limiting examples of dyes include alcian yellow, alizarin, alizarin yellow, Bismarck brown, brilliant cresyl blue, congo red, crystal violet, fuchsin acid, gentian violet, j anus green, lassamine fast yellow, marius yellow, meldola blue, metanil yellow, methyl orange, methyl red, naphthol green, orange G, purpurin, rose bengal, titan yellow, Victoria blue, alizarine cyanine green, alizarine brilliant blue, and the like. Non-limiting examples of pigments include metal-based pigment, an inorganic pigment, an organic pigment, or a biological pigment. In some embodiments, the pigment itself is insoluble but dispersible as fine particles in an aqueous medium. In an aspect, the pigment includes binders to facilitate dispersion.

In an aspect, the first optically detectable identifier 116 is a first colored particle and the second optically detectable identifier 126 is a second colored particle. For example, the optically detectable identifiers can include color-rich dyed particles (from, e.g., Thermo Fisher Scientific (Waltham, Mass.)).

In an aspect, the first optically detectable identifier 116 includes a first fluorophore capable of emitting fluorescence at the first wavelength and the second optically detectable identifier 126 includes a second fluorophore capable of emitting fluorescence at the second wavelength. In an aspect, the optically detectable identifiers include fluorescent dyes or fluorophores such as, for example, fluorescein (FITC), indocyanine green (ICG) and rhodamine B. Examples of other fluorescent dyes or fluorophores include but are not limited to a number of red and near infrared emitting fluorophores (600-1200 nm) including cyanine dyes such as Cy5, Cy5.5, and Cy7 (Amersham Biosciences, Piscataway, N.J., USA) and/or a variety of Alexa Fluor dyes such as Alexa Fluor 633, Alexa Fluor 635, Alexa Fluor 647, Alexa Fluor 660, Alexa Fluor 680, Alexa Fluor 700 and Alexa Fluor 750 (Molecular Probes-Invitrogen, Carlsbad, Calif., USA; see, e.g., U.S. Pat. App. No. 2005/0171434 A1). Additional fluorophores include IRDye800, IRDye700, and IRDye680 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS and ADS 821-NS (American Dye Source, Montreal, Calif.), NIAD-4 (ICx Technologies, Arlington, Va.). Other fluorescing agents include BODIPY-FL, europium, green, yellow and red fluorescent proteins.

In an aspect, the first optically detectable identifier 116 is a first fluorescing microsphere capable of emitting fluorescence at the first wavelength and the second optically detectable identifier 126 is a second fluorescing microsphere capable of emitting fluorescence at the second wavelength. For example, the optically detectable identifiers can include FluoSpheres® fluorescing at blue, blue-green, yellow-green, Nile red, orange, red-orange, red, crimson, dark red, or near infrared (from, Thermo Fisher Scientific, Waltham, Mass.). Other examples include fluorescing microspheres from Ocean NanoTech (San Diego, Calif., USA).

In an aspect, the first optically detectable identifier 116 is a first quantum dot capable of emitting at the first wavelength and the second optically detectable identifier 126 is a second quantum dot of emitting fluorescence at the second wavelength. For example, the first optically detectable identifier can include a first quantum dot type capable of emitting fluorescence at the first wavelength and the second optically detectable identifier can include a second quantum dot type capable of emitting fluorescence at the second wavelength. For example, the optically detectable identifiers can include very small (nanoscale) semiconductor nanocrystal particles or fluorescing quantum dots. In an aspect, the quantum dots can be formed from one or more of lead sulfide (PbS), lead selenide (Pb Se), cadmium selenide (CdSe), cadmium sulfide (CdS), cadmium telluride (CdTe), indium arsenide (CdAs), indium phosphide (InP), copper indium sulfide (CuInS), silver sulfide (Ag2S), and zinc sulfide (ZnS). For example, the optically detectable identifiers can include CdS/ZnS (emitting at 403-450 nm), CdSe/ZnS (emitting at 520-630 nm), CdSSe/ZnS (emitting at 450-665 nm), and InP/ZnS and PbS/Ag2S (emitting at 780-1600 nm). In an aspect, the quantum dots are coated or otherwise modified to improve aqueous solubility. For example, the quantum dots can be modified with polyethylene glycol (PEG), glutathione, dihydrolipoic acid, cysteine, or 3-mercaptopropionic acid to improve solubility. In an aspect, the quantum dots are associated with a micro- or nano-particle.

System 100 further includes at least one optically detectable reporter probe 130 capable of constitutively emitting a third wavelength in response to a reaction of the first set of one or more target-specific reagents 114 with the first target in a test sample and/or a reaction of the second set of one or more target-specific reagents 124 with the second target in the test sample. In an aspect, the at least one optically detectable reporter probe is capable of constitutively emitting a third wavelength in response to a reaction of the first set of one or more target-specific reagents with the first target or in response to a reaction of the second set of one or more target-specific reagents with the second target; or the at least one optically detectable reporter probe is capable of constitutively emitting a third wavelength in response to a reaction of the first set of one or more target-specific reagents with the first target and in response to a reaction of the second set of one or more target-specific reagents with the second target. The optically detectable reporter probe is designed to constitutively emit the third wavelength as long as at least one target is present to interact with target-specific reagents, but will also emit the third wavelength if at least one second target is present to interact with its respective target-specific reagents. The optically detectable reporter probe constitutively emits a wavelength (e.g., a wavelength or wavelength band of ultraviolet, visible light, or near infrared electromagnetic energy) in response to interaction of the one or more target-specific reagents with their intended target. In an aspect, the at least one optically detectable reporter probe is a generic or universal probe of a particular reaction type. For example, the at least one optically detectable reporter probe can be a general, generic, or universal probe of amplification reactions, binding reactions, enzymatic reactions, proliferation or cell viability reactions, and the like. For example, the at least one optically detectable reporter probe can include an intercalating reagent that emits a wavelength, (e.g., fluoresces) in response to the formation and increased concentration of double stranded DNA as a result of amplification of any DNA or RNA in the test sample. For example, the at least one optically detectable reporter probe can include a generic or universal marker of cell viability, e.g., a vital dye.

In some embodiments, the at least one optically detectable reporter probe 130 is a separate component of system 100 relative to the first set of particles 110 and the second set of particles 120. In some embodiments, the at least one optically detectable reporter probe 130 is associated with each particle of the first set of particles 110 and with each particle of the at least one second set of particles. For example, the at least one optically detectable reporter probe can be incorporated into the first and the at least one second set of particles during formation of the particles. For example, the at least one optically detectable reporter probe can be mixed with the set of one or more target-specific reagents and the optically detectable identifier prior to forming the particles.

In an aspect, the at least one optically detectable reporter probe is specific for a given set of one or more target-specific reagents and/or the specific target. For example, the at least one optically detectable reporter probe can include a TaqMan-like probe that binds to a specific nucleic acid sequence. In an aspect, the at least one optically detectable reporter probe 130 includes a first optically detectable reporter probe specific for the first target and a second optically detectable reporter probe specific for the second target. For example, a first optically detectable reporter probe can include a first TaqMan probe specific for a first nucleic acid sequence and a second optically detectable reporter probe can include a second TaqMan probe specific for a second nucleic acid sequence.

In an aspect, the at least one optically detectable reporter probe 130 comprises a DNA intercalating agent capable of constitutively emitting the third wavelength. For example, the at least one optically detectable reporter probe can include a DNA intercalating agent that is a fluorescing DNA-binding agent. The DNA intercalating agent can include any of a number of agents that preferentially bind to or intercalate into double stranded DNA and can be used as an indicator of amplification of a nucleic acid sequence. In some embodiments, the DNA intercalating agent can be used for quantification of amplification of a nucleic acid sequence. Non-limiting examples of fluorescing DNA intercalating agents include ethidium bromide, propidium iodide, DAPI, SYTO-9, SYTO-13, SYTO-82, SYBR Green 1, SYBR Gold, EvaGreen, and acridine orange.

In an aspect, the at least one optically detectable reporter probe 130 comprises a donor-acceptor pair capable of constitutively emitting the third wavelength. For example, the optically detectable reporter probe can include a donor-acceptor pair which constitutively emits a wavelength as long as the pair are in close proximity to one another by the process of fluorescence resonance energy transfer (FRET). FRET is a distance-dependent interaction between the electronic excited states of two dye molecules in which excitation is transferred from a donor molecule to an acceptor molecule without emission of a photon. In an aspect, interaction of a donor molecule with an acceptor molecule can lead to a shift in the emission wavelength associated with excitation of the acceptor molecule. In an aspect, interaction of a donor molecule with an acceptor molecule can lead to quenching of the donor emission. In some embodiments, the donor-acceptor pair are located on the same molecule and changes in the configuration or conformation of the molecule upon interacting with a target changes the distance between the donor and acceptor. In some embodiments, the donor and the acceptor are located on separate molecules. For example, the donor can be located on a first molecule (e.g., an antibody or aptamer) and the acceptor molecule can be located on a second molecule (a second antibody or aptamer) and when the first and second molecules are in proximity to one another, the emitted signal (e.g., fluorescence) from the donor-acceptor pair is altered (e.g., shifted or quenched).

A variety of donor and acceptor fluorophore pairs can be considered for FRET including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., USA) can be paired with other AF fluorophores for use in FRET. Some examples include, but are not limited, to AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

Other non-limiting examples of fluorophores for FRET-based signaling include cyanine dyes Cy3, Cy5, Cy5.5 and Cy7, which emit in the red and far red wavelength range (>550 nm). For example, Cy3, which emits maximally at 570 nm and Cy5, which emits at 670 nm, can be used as a donor-acceptor pair. When Cy3 and Cy5 are not proximal to one another, excitation at 540 nm results only in the emission from of light from Cy3 at 590 nm. In contrast, when Cy3 and Cy5 are brought into proximity by a conformation change, e.g., by binding of a microbe to a specific microbe-binding element, excitation at 540 nm results in an emission at 680 nm.

In some embodiments, the donor-acceptor pair includes a fluorophore-quencher pair. In an aspect, the at least one optically detectable reporter probe 130 comprises a fluorophore-quencher pair capable of constitutively emitting the third wavelength. For example, the optically detectable reporter probe can include a fluorophore-quencher pair in which the quencher molecule quenches fluorescence emitted by the fluorophore as long as the pair are in close proximity to one another by the process FRET. Upon increasing the distance between the pair, the fluorescence from the fluorophore becomes detectable. In some embodiments, the fluorophore-quencher pair are located on the same molecule and changes in the configuration or conformation of the molecule upon interacting with a target changes the distance between the fluorophore and quencher. In some embodiments, the fluorophore and the quencher are located on separated molecules. For example, the fluorophore can be located on first molecule (e.g., an antibody or aptamer) and the quencher can be located on a second molecule (a second antibody or aptamer) and when the first and second molecules are in proximity to one another, the fluorophore is quenched. If the binding targets of the first molecule and the second molecule are in close proximity, binding of these reagents to their respective targets will bring the fluorophore and quencher into proximity of one another, leading to a decrease in detected fluorescence.

In some embodiments, the at least one optically detectable reporter probe includes a fluorophore-quencher pair that constitutively emits a wavelength in response to a cleavage reaction. In an aspect, the at least one optically detectable reporter probe includes at least one oligonucleotide probe with a cleavable fluorophore-quencher pair. For example, the at least one optically detectable reporter probe can include at least one TaqMan™ probe designed to anneal with a portion of a nucleic acid sequence to be amplified by a specific primer set and to release the fluorophore in response to exonuclease activity of a DNA polymerase (from Thermo Fisher Scientific, Waltham, Mass.). Other commercially available probe systems that constitutively emit a wavelength or wavelength band in response to interacting with a nucleic acid sequence during an amplification reaction include, but are not limited to, LightCycler® Probes and Scorpions® Probes (from Sigma-Aldrich, Corp. St. Louis, Mo.) and MGB Eclipse® Probes (from Integrated DNA Technologies, Skokie, Ill.).

In some embodiments, the at least one optically detectable reporter probe includes a fluorophore-quencher pair that constitutively emits a wavelength in response to a structural confirmation change in the probe. In an aspect, the at least one optically detectable reporter probe includes a molecular beacon. For example, the at least one optically detectable reporter probe can include at least one oligonucleotide sequence with a stem-loop structure in the absence of binding, e.g., hybridizing, to a target and having a 5' fluorophore and a 3' quencher. Upon binding to a target sequence, the stem-loop structure is disrupted, the fluorophore and the quencher become spatially separated, resulting in emission of detectable fluorescence from the fluorophore.

In an aspect, the at least one optically detectable reporter probe includes an antibody, aptamer, or other binding entity including a fluorophore-quencher pair. For example, the at least one optically detectable reporter probe can include an antibody with a fluorophore and a quencher in close proximity to one another which separate in response to either degradation of the antibody upon cellular internalization or a conformational change in the antibody when it binds to its specific target.

A variety of fluorophore-quencher pairs can be considered for constitutive emission of a wavelength through FRET. Non-limiting examples include Cal Fluor Cold 540 or Cal Fluor Orange 560 paired with BHQ-1; 6-FAM, JOE, TET, or HEX paired with BHQ-1, DABCYL, or TAMRA; Cyanine 3, ROX, or TxRd paired with BHQ-2 or DABCYL; or Cyanine 5 or 5.5 paired with BHQ-3 or DABCYL. Other non-limiting examples of fluorophore and quencher pairs include fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes (from, e.g., Molecular Probes, Carlsbad, Calif., USA).

In an aspect, the at least one optically detectable reporter probe is an RNA or DNA oligonucleotide-based aptamer that includes a fluorophore-quencher pair. See, e.g., Cao et al. (2005) Current Proteomics 2:31-40 and U.S. Patent Application 2009/0186342, which are incorporated herein by reference. For example, the aptamer including a fluorophore-quencher pair can have a sequence designed to undergo a conformational change upon binding a target, causing the distance between the fluorophore and the quencher to shift, leading to a change in measurable fluorescence.

In an aspect, the at least one optically detectable reporter probe 130 comprises a probe of cell viability capable of constitutively emitting the third wavelength in response to cell viability. For example, the optically detectable reporter probe can be a generic or universal probe of cell viability. For example, the optically detectable reporter probe can be a live/dead cell indicator. For example, the optically detectable reporter probe can be a viability/cytotoxicity indicator. For example, the optically detectable reporter probe can constitutively report whether a cell population is alive or dead.

In an aspect, the at least one optically detectable reporter probe 130 is a probe of cell viability that includes an indicator of cell membrane integrity. The loss of cell membrane integrity is correlated with cell death. For example, the optically detectable reporter probe can include a vital dye, e.g., trypan blue, which is excluded from cells until the integrity of the cell membrane is compromised. Other non-limiting examples of vital dyes includes eosin, propidium iodide, erythrosine, aminoactinomycin D, indocyanine green, Brilliant blue, and Janus green B. For example, the optically detectable reporter probe can include red-fluorescent ethidium homodimer-1.

In an aspect, the at least one optically detectable reporter probe 130 is a probe of cell viability that includes a substrate for an enzymatic activity associated with dead or dying cells. For example, the optically detectable reporter probe can include a substrate of lactose dehydrogenase, glyceraldehyde 3-phosphate dehydrogenase, or adenylate kinase that releases a fluorescent, chemiluminescent, or bioluminescent product in response to enzymatic activity. In an aspect, the at least one optically detectable reporter probe 130 can include a generic or universal reporter of intracellular activity. For example, the at least one optically detectable reporter probe can include green-fluorescent calcein-AM to indicate intracellular esterase activity.

In some embodiments, the at least one optically detectable reporter probe 130 is a fluorophore-labeled bacteriophage. For example, the DNA of a bacteriophage can be labeled with a fluorescent dye or fluorophore (e.g., YOYO-1, DAPI, or SYBR Green) and used to bind to the surface of bacteria (prior to actual infection). For other non-limiting examples of reporting via labeling of phage DNA, see, e.g., Smartt & Ripp (2011) Anal. Bioanal. Chem. 400:991-1007, which is incorporated herein by reference.

In an aspect, the at least one optically detectable reporter probe 130 comprises a bacteriophage with a reporter gene capable of constitutively emitting the third wavelength. For example, a reporter gene or genes can be incorporated into the phage genome and upon infection of bacteria, the reporter gene(s) carried by the bacteriophage is expressed. As such, bacteriophage including a reporter gene can be used as an indicator of bacterial viability. In an aspect, the bacteriophage includes a reporter gene that generates a colorimetric, fluorescent, chemiluminescent, or bioluminescent signal in response to infection and propagation of viable bacterial cells. In some instances, the response is spontaneous (e.g., autofluorescence associated with green fluorescent protein). In some instances, the response requires a substrate or cofactor, either endogenous or exogenous to the bacteria (e.g., when the reporter gene is an enzyme). Non-limiting examples of reporter genes include those encoding green, yellow or red fluorescent protein (GFP, YFP, or RFP, respectively), bacterial luciferase, firefly luciferase, beta-galactosidase (lacZ), chloramphenyl acetyltransferase (CAT), beta-glucuronidase (GUS). For other non-limiting examples of reporting via reporter genes, see, e.g., Smartt & Ripp (2011) *Anal. Bioanal. Chem.* 400:991-1007, which is incorporated herein by reference.

In an aspect, the at least one optically detectable reporter probe 130 comprises a substrate capable of constitutively emitting the third wavelength in response to interaction with an enzyme. In an aspect, the substrate is at least one of a chemical substrate, a lipid-based substrate, a peptide-based substrate, or a protein-based substrate. In an aspect, the interaction of the substrate with a target enzyme produces a colorimetric or fluorogenic product. In an aspect, the interaction of the substrate with a target enzyme is detected by chemiluminescence. In an aspect, the at least one optically detectable reporter probe includes a substrate for at least one of beta-glucuronidase, beta-glucosidase, beta-galactosidase, beta-lactamase, beta-glucuronidase, alkaline phosphatase, luciferase, cytochrome P450, deubiquitinating enzyme, kinase, phosphatase, lipase, phospholipase, protease, or peptidase. In an aspect, the at least one optically detectable reporter probe includes a substrate that interacts with a component of a cell membrane (e.g., lipids, proteins and protein receptors, and carbohydrates). A number of substrates which constitutively emit a wavelength in response to interaction with an enzymatic target are available from commercial sources (from, e.g., Thermo Fisher Scientific, Waltham, Mass.).

In an aspect, the at least one optically detectable reporter probe 130 includes a substrate for beta-glucuronidase. For example, the substrate for beta-glucuronidase can include a substrate that generates a colorimetric precipitate in response to the interaction. Non-limiting examples include 5-bromo-4-chloro-3-indolyl-beta-D-glucuronide (X-GlcA), para-nitrophenyl-β-D glucuronide (pNPG), and phenolphthalein-β-D-glucuronide (PHTG). For example, the substrate for beta-glucuronidase can include a substrate that generates a fluorogenic product in response to the interaction. A non-limiting example includes 4-methylumbelliferyl-β-D-glucuronide (MUG).

In an aspect, the at least one optically detectable reporter probe 130 includes a substrate for beta-galactosidase. For example, the substrate for beta-galactosidase can include a substrate that generates a colorimetric precipitate in response to the interaction, non-limiting examples of which include 5-bromo-4-chloro-3-indolyl-β-d-galactopyranoside (X-gal), halogenated indolyl-β-galactoside, or ortho-nitrophenyl-β-D-galactopyranoside (ONPG). For example, the substrate of beta-galactosidase can include a substrate that generates a fluorogenic product in response to the interaction, a non-limiting example of which includes 4-methyl-umbelliferyl-β-D-galactosidase.

In an aspect, the system further includes one or more reaction reagents for performing the multiplex analysis. In an aspect, the one or more reaction reagents include one or more reagents suitable for performing an amplification reaction. For example, the one or more reaction reagents can include one or more reagents for performing polymerase chain reaction (PCR) amplification such as, e.g., a DNA polymerase (e.g., Taq polymerase), deoxynucleoside triphosphates or deoxynucleotide triphosphates (dNTPs), a buffer solution, bivalent cations (e.g., magnesium or manganese ions), and monovalent cations (e.g., potassium ions). In an aspect, the one or more reaction reagents comprise one or more reagents suitable for performing isothermal amplification. For example, the one or more reaction reagents can include reagents for performing recombinase polymerase amplification (RPA), loop-mediated isothermal amplification (LAMP), nucleic acid sequence based amplification (NASBA), helicase-dependent amplification (HAD), and nicking enzyme amplification reaction (NEAR). For example, the one or more reaction reagents can include one or more of a recombinase, a single-stranded DNA-binding protein, a strand displacing polymerase, a helicase, an endonuclease.

In an aspect, the one or more reaction reagents include one or more components of a growth or culture medium. For example, the one or more reaction reagents can include components of a growth or culture medium for culturing cells and can be either synthetic or chemically defined or non-synthetic or chemically undefined. The culture or growth medium can be selected or designed to support growth of microorganisms (e.g., bacteria or fungi) or cells (tissue culture cells or primary cells) and may include a carbon source (e.g., glucose), various salts, and a source of amino acids and nitrogen. In some embodiments, the culture or growth medium includes a selective medium for selective growth of a type(s) of cell. In some embodiments, the culture or growth medium includes a differential or indicator medium for detecting selective growth of a type(s) of cell. The one or more reaction reagents can include any of a number of nutrients, amino acids, lipids, carbohydrates, sugars, and salts necessary to promote growth of a given cell type(s). In some embodiments, the one or more reaction reagents include one or more reagents for lysing cells. For example, the reaction reagents can include enzymes (e.g., lysozyme) and detergents (e.g., NP-40, sodium deoxycholate).

In an aspect, the one or more reaction reagents include one or more reagents necessary or sufficient for performing a chemical reaction. In an aspect, the one or more reaction reagents include one or more reagents necessary or sufficient for an enzymatic reaction. For example, the one or more reaction reagents can include enzymes, substrates, buffers, salts, ions, inorganic or organic co-factors, co-enzymes, and any other reagents necessary or sufficient for a given enzymatic reaction.

Described herein is a system for multiplexed detection of two or more nucleic acid sequences in a test sample. The system includes two or more sets of particles including a first set of particles, each particle of the first set of particles degradable in response to a first environmental condition and having associated therewith a first amplification primer set and a first optically detectable identifier capable of emitting a first wavelength, the first amplification primer set selected to specifically interact with a first nucleic acid sequence, and the first optically detectable identifier indicative of the first amplification primer set; and at least one second set of particles, each particle of the at least second set of particles degradable in response to a second environmental condition and having associated therewith a second amplification primer set and a second optically detectable identifier capable of emitting a second wavelength, the second amplification primer set selected to specifically interact with a second nucleic acid sequence, and the second optically detectable identifier indicative of the second amplification primer set; and at least one optically detectable reporter probe capable of constitutively emitting a third wavelength in response to amplification of the first nucleic acid sequence in the test sample and/or the second nucleic acid sequence in the test sample.

FIG. 3 illustrates a non-limiting example of a system for multiplexed detection of two or more nucleic acid sequences in a test sample. System 300 includes two or more sets of particles 305 and at least one optically detectable reporter probe 330. The two or more sets of particles include a first set of particles 310 and at least one second set of particles 320. Particles 312a, 312b, 312c, 312d, 312e, and 312f are representative of particles in the first set of particles 310 and are degradable in response to a first environmental condition (e.g., temperature, pH, chemical reaction, electric field, or electromagnetic energy). Each of the particles 312a-312f include a first amplification primer set 314 and a first optically detectable identifier 316. The first amplification primer set 314 is selected to specifically interact with a first nucleic acid sequence. First optically detectable identifier 316 is capable of emitting a first wavelength (as represented by the horizontal line pattern in particles 312a-312f) and is indicative of the first amplification primer set. Particles 322a, 322b, 322c, 322d, 322e, and 322f are representative of particles in the at least one second set of particles and are degradable in response to a second environmental condition. In some embodiments, the second environmental condition is the same as the first environmental condition. In other embodiments, the second environmental condition differs from the first environmental condition. Each of the particles 322a-322f include a second amplification primer set 324 and a second optically detectable identifier 326. Second amplification primer set 324 is selected to specifically interact with a second nucleic acid sequence. Second optically detectable identifier 326 is capable of emitting a second wavelength (represented by the diagonal line pattern in particles 322a-322f) and is indicative of the second amplification primer set. The first amplification primer set 314 and the second amplification primer set 324 have sequence(s) selected or designed to hybridize to their respective first and second target nucleic acid sequences. For example, the amplification primer sets can include complimentary nuclei acid sequences that at least partially hybridize to a corresponding target nucleic acid sequence. At least one optically detectable reporter probe 330 is capable of constitutively (as shown by arrow 332) emitting a third wavelength 334 (represented by the cross-hatched lines) in response to amplification of the first nucleic acid sequence in the test sample by the first amplification primer set 314 and/or the second nucleic acid sequence in the test sample by the second amplification primer set 324.

In an aspect, system 300 for multiplexed detection of two or more nucleic acid sequences in a test sample includes components designed to detect two or more nucleic acid sequences derived from one or more types of bacteria. In an aspect, the first amplification primer set 314 and the second amplification primer set 324 are selected to specifically interact with nucleic acid sequences derived from one or more types of bacteria. For example, the first amplification primer set can have sequence(s) selected or designed to specifically interact (e.g., at least partially hybridize) with a first nucleic acid sequence derived from a bacteria type and the second amplification primer set can have sequence(s) selected or designed to specifically interact (e.g., at least partially hybridize) with a second nucleic acid sequence derived from the same bacteria type or a second bacteria type. For example, the amplification primer sets can have sequence(s) selected or designed to specifically interact (e.g., at least partially hybridize) with nucleic acid sequences derived from bacteria and/or other microorganisms suspected of contaminating a water source, e.g., a well or reservoir. For example, the amplification primer sets can have sequence(s) selected or designed to specifically interact (e.g., at least partially hybridize) with nucleic acid sequences derived from a sputum sample suspected of containing *Mycobacterium tuberculosis* and/or other forms of *Mycobacterium*. For example, the amplification primer sets can have sequence(s) selected or designed to specifically interact (e.g., at least partially hybridize) with nucleic acid sequences derived from a blood sample of an individual diagnosed with sepsis. In an aspect, the amplification primer sets can have sequence(s) selected or designed to specifically interact (e.g., at least partially hybridize) with nucleic acid sequences associated with and/or derived from at least one of methicillin resistant *Staphylococcus aureus*, methicillin susceptible *Staphylococcus aureus, Escherichia coli, Streptococcus pneumonia, Pseudomonas aeruginosa, Staphylococcus epidermidis, Salmonella enterica, Klebsiella pneumonia, Streptococcus pyogenes, Acinetobacter baumannii*, or *Enterococcus faecalis*.

In an aspect, system 300 for multiplexed detection of two or more nucleic acid sequences in a test sample includes components designed to detect two or more nucleic acid sequences derived from one or more cell types. In an aspect, the first amplification primer set 314 and the second amplification primer set 324 of system 300 are selected to specifically interact with nucleic acid sequences derived from one or more cell types. For example, the amplification primer sets can have sequence(s) selected or designed to specifically interact (e.g., at least partially hybridize) with two or more nucleic acid sequences derived from microorganisms, e.g., bacteria, fungi, viruses, parasites, and the like. For example, the amplification primer sets can have sequence(s) selected or designed to specifically interact (e.g., at least partially hybridize) with two or more nucleic acid sequences derived from pathogens. For example, the amplification primer sets can have sequence(s) selected or designed to specifically interact (e.g., at least partially hybridize) with two or more nucleic acid sequences derived from a body fluid or tissue. For example, the amplification primer sets can have sequence(s) selected or designed to specifically interact (e.g., at least partially hybridize) with two or more nucleic acid sequences derived from blood cells (e.g., red blood cells, white blood cells, platelets), inflammatory cells (e.g., macrophage, T-cells, B-cells, mast cells, eosinophils, basophils, neutrophils, monocytes), epithelial cells, hormone secreting cells, nerve cells, adipocytes, renal cells, contractile cells, and/or germ cells). In some embodiments, the amplification primer sets can have sequence(s) selected or designed to specifically interact (e.g., at least partially hybridize) with two or more nucleic acid sequences derived from a tumor, malignant, and/or cancerous cell.

In an aspect, at least one of the two or more nucleic acid sequences in the test sample comprises a single stranded DNA sequence, a double stranded DNA sequence, or an RNA sequence. In an aspect, the first amplification primer set 314 and the second amplification primer set 324 of system 300 are selected to specifically interact with at least one of single stranded DNA sequences, double stranded DNA sequences, or RNA sequences. In an aspect, the amplification primer sets have sequence(s) selected or designed to detect and/or amplify single or double stranded DNA or RNA sequence. In some embodiments amplification is done to detect the presence of a particular nucleic acid sequence as an indicator of the presence of a particular cell type. In some embodiments, amplification is done to quantify the amount of a particular nucleic acid sequence. Each amplification primer set can include from one to ten short oligonucleotide primers having from 10-40 bases each. In an aspect, the first amplification primer set 314 and the second amplification primer set 324 are designed for use with polymerase chain reaction (PCR) amplification. In an aspect, the first amplification primer set 314 and the second amplification primer set 324 are designed for real-time or quantitative PCR. For example, each amplification primer set can include a pair of DNA primers or oligonucleotides that are complementary to the three prime ends of each of the sense and anti-sense strands of the target nucleic acid sequence. For example, each amplification primer set can include a forward primer and a reverse primer.

In an aspect, the first amplification primer set 314 and the second amplification primer set 324 are designed for use with an isothermal amplification process. For example, each amplification primer set can include from one to four pairs of DNA primers or oligonucleotides having 10-40 bases each. For example, the amplification primer set can include one or more loop primers. For example, the amplification primer set can include two or more inner primers and two or more outer primers. For example, the amplification primer set can include one or more forward primers and one or more reverse primers. For example, the first amplification primer set and the second amplification primer set can be designed for one or more of recombinase polymerase amplification (RPA), loop-mediated isothermal amplification (LAMP), nucleic acid sequence based amplification (NASBA), helicase-dependent amplification (HAD), or nicking enzyme amplification reaction (NEAR).

The first set of particles 310 are degradable in response to a first environmental condition and the at least one second set of particles 320 are degradable in response to a second environmental condition. In an aspect, the first environmental condition and the second environmental condition comprise at least one of temperature, pH, chemical reaction, electric field, or electromagnetic energy. For example, the first set of particles and the second set of particles are degradable in response to a change in at least one of temperature, pH, chemical reaction, electric field, or electromagnetic energy. For example, the first set of particles and the second set of particles can be formed from materials that are degradable in response to a change in at least one of temperature, pH, chemical reaction, electric field, or electromagnetic energy.

In some embodiments, the first environmental condition and the second environmental condition are identical environmental conditions. For example, the first set of particles and the at least one second set of particles can be degradable in response to identical environmental conditions, for example, an identical condition of temperature, pH, chemical reaction, electric field, and/or electromagnetic energy. For example, the first set of particles and the at least one second set of particles can be formed from materials that are degradable in response to identical environmental conditions of temperature, pH, chemical reaction, electric field, and/or electromagnetic energy.

In an aspect, the particles of the first set of particles 310 and of the at least one second set of particles 320 include a structure formed from a degradable material that is degradable in response to at least the first environmental condition or the second environmental condition. In an aspect, the particles of the first set of particles 310 and of the at least one second set of particles 320 include a structure formed from a degradable gel. In an aspect, the particles of the first set of particles 310 and of the at least one second set of particles 320 include a structure formed from low melt agarose. In an aspect, the particles of the first set of particles 310 and of the at least one second set of particles 320 include a structure formed from a degradable alginate. In an aspect, the particles of the first set of particles 310 and of the at least one second set of particles 320 include a structure formed from a degradable sugar. In an aspect, the particles of the first set of particles 310 and of the at least one second set of particles 320 include a structure formed from a temperature-responsive degradable material. In an aspect, the particles of the first set of particles 310 and of the at least one second set of particles 320 include a structure formed from a pH-responsive degradable material. In an aspect, the particles of the first set of particles 310 and of the at least one second set of particles 320 include a structure formed from a chemically-responsive degradable material. In an aspect, the particles of the first set of particles 310 and of the at least one second set of particles 320 include a structure formed from an electric field-responsive degradable material. In an aspect, the particles of the first set of particles 310 and of the at least one second set of particles 320 include a structure formed from an electromagnetic energy-responsive degradable material. Non-limiting examples of environmental condition-responsive degradable materials for forming the particles are presented above herein.

The two or more sets of particles 305 are designed for use in a multiplex analysis of two or more nucleic acid sequences in a test sample. In some embodiments, the multiplex analysis includes performing reactions in aqueous-in-oil droplets or an emulsion system. In an aspect, at least a portion of the particles of the first set of particles 310 and of the at least one second set of particles 320 are distributable into an aqueous portion of aqueous-in-oil droplets. In an aspect, the particles of the first set of particles 310 and of the at least one second set of particles 320 are hydrophilic. In an aspect, the particles of the first set of particles 310 and of the at least one second set of particles 320 include a structure at least partially formed from a hydrophilic material. Non-limiting examples of materials for forming hydrophilic particles have been described above herein.

System 300 for multiplexed detection of two or more nucleic acid sequences in a test sample includes a first set of particles 310 including a first optically detectable identifier 316 capable of emitting a first wavelength, at least one second set of particles 320 including a second optically detectable identifier 326 capable of emitting a second wavelength, and at least one optically detectable reporter probe 330 capable of constitutively emitting a third wavelength. In an aspect, the first wavelength emitted by the first optically detectable identifier 316 is a first detectable color, the second wavelength emitted by the second optically detectable identifier 326 is a second detectable color, and the third wavelength constitutively emitted by the at least one optically detectable reporter probe 330 is a third detectable color. In an aspect, the first wavelength, the second wavelength, and the third wavelength are optically discernable from one another. In an aspect, the first wavelength, the second wavelength, or the third wavelength is an ultraviolet wavelength or wavelength band of electromagnetic energy. In an aspect, at least one of the first wavelength, the second wavelength, or the third wavelength is a visible wavelength or wavelength band of electromagnetic energy. In an aspect, the first wavelength, the second wavelength, or the third wavelength is a near infrared wavelength or wavelength band of electromagnetic energy.

In an aspect, the first optically detectable identifier 316 is a first colored dye or pigment and the second optically detectable identifier 326 is a second colored dye or pigment. In an aspect, the first optically detectable identifier 316 includes a first fluorophore capable of emitting fluorescence at the first wavelength and the second optically detectable identifier 326 includes a second fluorophore capable of emitting fluorescence at the second wavelength. In an aspect, the first optically detectable identifier 316 is a first quantum dot capable of emitting the first wavelength and the second optically detectable identifier 326 is a second quantum dot capable of emitting the second wavelength. Non-limiting examples of dyes, pigments, fluorescent dyes/fluorophores, colored or fluorescent particles, and quantum dots have been described above.

System 300 for multiplexed detection of two or more nucleic acid sequences in a test sample includes at least one optically detectable reporter probe 330 capable of constitutively emitting a third wavelength in response to amplification of the first nucleic acid sequence in the test sample and/or the second nucleic acid sequence in the test sample. In some embodiments, the at least one optically detectable reporter probe 330 is associated with each particle of the first set of particles 310 and with each particle of the at least one second set of particles 320. In some embodiments, the at least one optically detectable reporter probe 330 includes a first optically detectable reporter probe specific for amplification of the first nucleic acid sequence and a second optically detectable reporter probe specific for amplification of the second nucleic acid sequence. For example, the first optically detectable reporter probe can be designed to constitutively emit a detectable wavelength in response to binding or hybridizing to the first nucleic acid sequence while the second optically detectable reporter probe can be designed to constitutively emit a second wavelength in response to binding or hybridizing to the second nucleic acid sequence. For example, the first optically detectable reporter probe and the second detectable reporter probe can include sequence specific TaqMan-like probes or molecular beacons.

In an aspect, the at least one optically detectable reporter probe 330 comprises a donor-acceptor pair capable of constitutively emitting the third wavelength. In an aspect, the at least one optically detectable reporter probe 330 comprises a fluorophore-quencher pair capable of constitutively emitting the third wavelength. For example, the optically detectable reporter probe can include a fluorophore-quencher pair in which a quencher molecule quenches fluorescence emitted by the fluorophore as long as the pair are in close proximity to one another. In some embodiments, the fluorophore-quencher pair are located on the same molecule and changes in the configuration or conformation of the molecule upon interacting with a target changes the distance between the fluorophore and quencher. In some embodiments, the fluorophore and the quencher are located on separate binding molecules (e.g., oligonucleotides, aptamers, or antibodies,) such that if the targets of a first binding molecule and a second binding molecule are in close proximity, binding of these molecules to their respective targets will bring the fluorophore and quencher into proximity of one another, leading to a decrease in detected fluorescence.

In some embodiments, the at least one optically detectable reporter probe 330 includes a fluorophore-quencher pair that constitutively emits a wavelength in response to a cleavage reaction triggered by the amplification of the first or the second nucleic acid sequence. In an aspect, the at least one optically detectable reporter probe 330 includes at least one oligonucleotide probe with a cleavable fluorophore-quencher pair. For example, the at least one optically detectable reporter probe can include at least one TaqMan™ probe designed to anneal with a portion of a nucleic acid sequence to be amplified by a specific primer set and to release the fluorophore in response to exonuclease activity of a DNA polymerase (from Thermo Fisher Scientific, Waltham, Mass.). Other commercially available probe systems that constitutively emit a wavelength or wavelength band in response to interacting with a nucleic acid sequence during an amplification reaction include, but are not limited to, LightCycler® Probes and Scorpions® Probes (from Sigma-Aldrich, Corp. St. Louis, Mo.) and MGB Eclipse® Probes (from Integrated DNA Technologies, Skokie, Ill.).

In some embodiments, the at least one optically detectable reporter probe 330 includes a fluorophore-quencher pair that constitutively emits a wavelength in response to a structural confirmation change in the probe. In an aspect, the at least one optically detectable reporter probe 330 includes a molecular beacon. For example, the at least one optically detectable reporter probe can include at least one oligonucleotide sequence with a stem-loop structure in the absence of binding, e.g., hybridizing, to a target and having a 5' fluorophore and a 3' quencher. Upon binding to a target nucleic acid sequence, the stem-loop structure is disrupted, the fluorophore and the quencher become spatially separated, resulting in emission of detectable fluorescence from the fluorophore.

In an aspect, the at least one optically detectable reporter probe 330 is an RNA or DNA oligonucleotide-based aptamer that includes a fluorophore-quencher pair. In an aspect, the at least one optically detectable reporter probe 330 includes an antibody or other binding entity including a fluorophore-quencher pair. Non-limiting examples of fluorophore-quencher pairs have been described above herein.

In an aspect, the at least one optically detectable reporter probe 330 comprises a DNA intercalating agent capable of constitutively emitting the third wavelength. For example, the optically detectable reporter probe can include any of a number of fluorescing DNA-binding agents that preferentially bind to double stranded DNA and can be used as a quantification of amplification of a nucleic acid sequence. Non-limiting examples include ethidium bromide, propidium iodide, DAPI, SYTO-9, SYTO-13, SYTO-82, SYBR Green 1, SYBR Gold, EvaGreen, and acridine orange.

In some embodiments, system 300 for multiplexed detection of two or more nucleic acid sequences further includes one or more reaction reagents for performing the multiplexed detection of the two or more nucleic acid sequences in the test sample. In an aspect, the one or more reaction reagents comprise one or more reaction reagents for amplification of the two or more nucleic acid sequences in the test sample. For example, the one or more reaction reagents can include one or more reagents for performing polymerase chain reaction (PCR) amplification such as, e.g., a DNA polymerase (e.g., Taq polymerase), deoxynucleoside triphosphates or deoxynucleotide triphosphates (dNTPs), a buffer solution, bivalent cations (e.g., magnesium or manganese ions), and monovalent cations (e.g., potassium ions). In an aspect, the one or more reaction reagents comprise one or more reagents suitable for performing isothermal amplification. For example, the one or more reaction reagents can include reagents for performing recombinase polymerase amplification (RPA), loop-mediated isothermal amplification (LAMP), nucleic acid sequence based amplification (NASBA), helicase-dependent amplification (HAD), and nicking enzyme amplification reaction (NEAR). For example, the one or more reaction reagents can include, but are not limited to, one or more of a reverse transcriptase, an RNase, an RNA polymerase, a ligase, a recombinase, a single-stranded DNA-binding protein, a strand displacing polymerase, a helicase, an endonuclease.

In an aspect, system 300 for multiplexed analysis of two or more nucleic acid sequences in a test sample includes more than two sets of particles. In an aspect, system 300 includes three, four, five, six, seven, eight, nine, ten, eleven, twelve, thirteen, fourteen, fifteen, sixteen, seventeen, eighteen, nineteen, or twenty sets of particles, each set of particles includes an amplification primer set and an optically detectable identifier.

In an aspect, system 300 includes at least one third set of particles, each particle of the at least one third set of particles degradable in response to at least one of the first, the second, or a third environmental condition and having associated therewith a third amplification primer set and a third optically detectable identifier capable of emitting a fourth wavelength, the third amplification primer set selected to specifically interact with a third nucleic acid sequence, and the third optically detectable identifier indicative of the third amplification primer set; and wherein the at least one optically detectable reporter probe is capable of constitutively emitting the third wavelength in response to amplification of the first nucleic acid sequence in the test sample, the second nucleic acid sequence in the test sample, and/or the third nucleic acid sequence in the test sample; and wherein the first wavelength, the second wavelength, the third wavelength, and the fourth wavelength are optically discernable from one another. In an aspect, the first, second, and third environmental condition is the same environmental condition (e.g., temperature, pH, chemical reaction, electric field, or electromagnetic energy).

Described herein is a system for multiplexed detection of two or more bacterial nucleic acid sequences in a test sample. The system includes two or more sets of particles including a first set of particles, each particle of the first set of particles degradable in response to a first temperature condition and having associated therewith a first amplification primer set and a first fluorescent identifier capable of emitting at a first wavelength, the first amplification primer set selected to specifically interact with a first bacterial nucleic acid sequence, and the first fluorescent identifier indicative of the first amplification primer set; and at least one second set of particles, each particle of the at least one second set of particles degradable in response to a second temperature condition and having associated therewith a second amplification primer set and a second fluorescent identifier capable of emitting at a second wavelength, the second amplification primer set selected to specifically interact with a second bacterial nucleic acid sequence, and the second fluorescent identifier indicative of the second amplification primer set; and at least one fluorescent intercalating agent capable of constitutively emitting at a third wavelength in response to amplification of the first bacterial nucleic acid sequence in the test sample and/or the second bacterial nucleic acid sequence in the test sample.

FIG. 4 illustrates a non-limiting example of a system for multiplexed detection of two or more bacterial nucleic acid sequences in a test sample. System 400 includes two or more sets of particles 405 and at least one fluorescent intercalating agent 430. The two or more sets of particles include a first set of particles 410 and at least one second set of particles 420. Particles 412a, 412b, 412c, 412d, 412e, and 412f are representative of particles in the first set of particles 410 and are degradable in response to a first temperature condition. Each of the particles 412a-412f include a first amplification primer set 414 and a first fluorescent identifier 416. The first amplification primer set 414 is selected to specifically interact with a first bacterial nucleic acid sequence. First fluorescent identifier 416 is capable of emitting at a first wavelength (as represented by the diagonal line pattern in particles 412a-412f) and is indicative of the first amplification primer set. Particles 422a, 422b, 422c, 422d, 422e, and 422f are representative of particles in the at least one second set of particles and are degradable in response to a second temperature condition. In some embodiments, the second temperature condition is the same as the first temperature condition. For example, the first set of particles 410 and the at least one second set of particles 420 can be formed from a material(s) that degrades at a temperature encountered during amplification cycling. Each of the particles 422a-422f include a second amplification primer set 424 and a second fluorescent identifier 426. Second amplification primer set 424 is selected to specifically interact with a second bacterial nucleic acid sequence. Second fluorescent identifier 426 is capable of emitting at a second wavelength (represented by the vertical line pattern in particles 422a-422f) and is indicative of the second amplification primer set. The first amplification primer set 414 and the second amplification primer set 424 have sequence(s) selected or designed to hybridize to their respective first and second target bacterial nucleic acid sequences. For example, the amplification primer sets can include complimentary nuclei acid sequences that at least partially hybridize to a corresponding target bacterial nucleic acid sequence. At least one fluorescent intercalating agent 430 is capable of constitutively (as shown by arrow 432) emitting at a third wavelength 434 (represented by the cross-hatched lines) in response to amplification of the first bacterial nucleic acid sequence in the test sample by the first amplification primer set 414 and/or the second bacterial nucleic acid sequence in the test sample by the second amplification primer set 424.

System 400 includes components designed to detect two or more bacterial nucleic acid sequences derived from one or more types of bacteria. In an aspect, the first amplification primer set 414 and the second amplification primer set 424 are selected to specifically interact with bacterial nucleic acid sequences derived from one or more types of bacteria. For example, the first amplification primer set can have sequence(s) selected or designed to specifically interact (e.g., at least partially hybridize) with a first bacterial nucleic acid sequence derived from a bacteria type and the second amplification primer set can have sequence(s) selected or designed to specifically interact (e.g., at least partially hybridize) with a second bacterial nucleic acid sequence derived from the same bacteria type or a second bacteria type. For example, the amplification primer sets can have sequence(s) selected or designed to specifically interact (e.g., at least partially hybridize) with bacterial nucleic acid sequences derived from bacteria suspected of contaminating a water source, e.g., a well or reservoir. For example, the amplification primer sets can have sequence(s) selected or designed to specifically interact (e.g., at least partially hybridize) with nucleic acid sequences derived from a sputum sample suspected of containing *Mycobacterium tuberculosis* and/or other forms of *Mycobacterium*. For example, the amplification primer sets can have sequence(s) selected or designed to specifically interact (e.g., at least partially hybridize) with bacterial nucleic acid sequences derived from a blood sample or other biological sample of an individual diagnosed with sepsis. In an aspect, the amplification primer sets can have sequence(s) selected or designed to specifically interact (e.g., at least partially hybridize) with bacterial nucleic acid sequences associated with and/or derived from at least one of methicillin resistant *Staphylococcus aureus*, methicillin susceptible *Staphylococcus aureus, Escherichia coli, Streptococcus pneumonia, Pseudomonas aeruginosa, Staphylococcus epidermidis, Salmonella enterica, Klebsiella pneumonia, Streptococcus pyogenes, Acinetobacter baumannii*, or *Enterococcus faecalis*.

In an aspect, at least one of the two or more nucleic acid sequences in the test sample comprises a single stranded DNA sequence, a double stranded DNA sequence, or an RNA sequence. In an aspect, the first amplification primer set 414 and the second amplification primer set 424 of system 400 are selected to specifically interact with at least one of single stranded DNA sequences, double stranded DNA sequences, or RNA sequences. In an aspect, the amplification primer sets have sequence(s) selected or designed to detect and/or amplify single or double stranded DNA or RNA sequence derived from bacteria. In some embodiments amplification is done to detect the presence of a particular bacterial nucleic acid sequence as an indicator of the presence of a particular bacteria type. In some embodiments, amplification is done to quantify the amount of a particular bacterial nucleic acid sequence. Each amplification primer set can include from one to ten short oligonucleotide primers having from 10-40 bases each. In an aspect, the first amplification primer set 414 and the second amplification primer set 424 are designed for use with polymerase chain reaction (PCR) amplification. In an aspect, the first amplification primer set 414 and the second amplification primer set 424 are designed for real-time or quantitative PCR. For example, each amplification primer set can include a pair of DNA primers or oligonucleotides that are complementary to the three prime ends of each of the sense and anti-sense strands of the target bacterial nucleic acid sequence. For example, each amplification primer set can include a forward primer and a reverse primer.

In an aspect, first amplification primer set 414 and the second amplification primer set 424 are designed for use with an isothermal amplification process. For example, each amplification primer set can include from one to four pairs of DNA primers or oligonucleotides having 10-40 bases each. For example, the amplification primer set can include one or more loop primers. For example, the amplification primer set can include two or more inner primers and two or more outer primers. For example, the amplification primer set can include one or more forward primers and one or more reverse primers. For example, the first amplification primer set and the second amplification primer set can be designed for one or more of recombinase polymerase amplification (RPA), loop-mediated isothermal amplification (LAMP), nucleic acid sequence based amplification (NASBA), helicase-dependent amplification (HAD), or nicking enzyme amplification reaction (NEAR).

The first set of particles 410 are degradable in response to a first temperature condition and the at least one second set of particles 420 are degradable in response to a second temperature condition. In some embodiments, the first temperature condition and the second temperature condition are the same temperature condition. For example, the first set of particles and the at least one second set of particles can be degradable in response to identical temperature conditions. For example, the first set of particles and the at least one second set of particles can be formed from materials that are degradable in response to identical temperature conditions.

In an aspect, the particles of the first set of particles 410 and of the at least one second set of particles 420 include a structure formed from a degradable material that is degradable in response to at least the first temperature condition or the second temperature condition. In an aspect, the particles of the first set of particles 410 and of the at least one second set of particles 420 include a structure formed from a degradable gel that is degradable in response to at least the first temperature condition or the second temperature condition. In an aspect, the particles of the first set of particles 410 and of the at least one second set of particles 420 include a structure formed from low melt agarose that is degradable in response to at least the first temperature condition or the second temperature condition. In an aspect, the particles of the first set of particles 410 and of the at least one second set of particles 420 include a structure formed from a temperature-responsive degradable material that is degradable in response to at least the first temperature condition or the second temperature condition. Non-limiting examples of temperature condition-responsive degradable materials for forming the particles are presented above herein.

The two or more sets of particles 405 are designed for use in a multiplex analysis of two or more bacterial nucleic acid sequences in a test sample. In some embodiments, the multiplex analysis includes performing reactions in aqueous-in-oil droplets or an emulsion system. In an aspect, at least a portion of the particles of the first set of particles 410 and of the at least one second set of particles 420 are distributable into an aqueous portion of aqueous-in-oil droplets. In an aspect, the particles of the first set of particles 410 and of the at least one second set of particles 420 are hydrophilic. In an aspect, the particles of the first set of particles 410 and of the at least one second set of particles 420 include a structure at least partially formed from a hydrophilic material. Non-limiting examples of materials for forming hydrophilic particles have been described above herein.

System 400 for multiplexed detection of two or more bacterial nucleic acid sequences in a test sample includes a first set of particles 410 including a first fluorescent identifier 416 capable of emitting at a first wavelength, at least one second set of particles 420 including a second fluorescent identifier 426 capable of emitting at a second wavelength, and at least one fluorescent intercalating agent 430 capable of constitutively emitting at a third wavelength. In an aspect, the first wavelength emitted by the first fluorescent identifier 416 is a first detectable color, the second wavelength emitted by the second fluorescent identifier 426 is a second detectable color, and the third wavelength constitutively emitted by the at least one fluorescent intercalating agent 430 is a third detectable color. In an aspect, the first wavelength, the second wavelength, and the third wavelength are optically discernable from one another. In an aspect, the first wavelength, the second wavelength, or the third wavelength is an ultraviolet wavelength or wavelength band of electromagnetic energy. In an aspect, at least one of the first wavelength, the second wavelength, or the third wavelength is a visible wavelength or wavelength band of electromagnetic energy. In an aspect, the first wavelength, the second wavelength, or the third wavelength is a near infrared wavelength or wavelength band of electromagnetic energy.

In an aspect, the first fluorescent identifier 416 is a first fluorescent dye or pigment and the second fluorescent identifier 426 is a second fluorescent dye or pigment. In an aspect, the first fluorescent identifier 416 includes a first fluorophore capable of emitting fluorescence at the first wavelength and the second fluorescent identifier 426 includes a second fluorophore capable of emitting fluorescence at the second wavelength. In an aspect, the first fluorescent identifier 416 is a first quantum dot capable of emitting the first wavelength and the second fluorescent identifier 426 is a second quantum dot capable of emitting the second wavelength. Non-limiting examples of dyes, pigments, fluorescent dyes/fluorophores, colored or fluorescent particles, and quantum dots have been described above.

System 400 for multiplexed detection of two or more bacterial nucleic acid sequences in a test sample includes at least one fluorescent intercalating agent 430 capable of constitutively emitting at a third wavelength in response to amplification of the first bacterial nucleic acid sequence in the test sample and/or the second bacterial nucleic acid sequence in the test sample. In some embodiments, the at least one fluorescent intercalating agent 430 is associated with each particle of the first set of particles 410 and with each particle of the at least one second set of particles 420.

In an aspect, the fluorescent intercalating agent 430 includes a fluorescent DNA intercalating agent. For example, the fluorescent intercalating agent can include any of a number of fluorescing DNA-binding agents that preferentially bind to double stranded DNA and can be used as an optically detectable reporter probe of amplification of a nucleic acid sequence. Non-limiting examples of fluorescent intercalating agents include, but are not limited to, ethidium bromide, propidium iodide, DAPI, SYTO-9, SYTO-13, SYTO-82, SYBR Green 1, SYBR Gold, EvaGreen, and acridine orange.

In some embodiments, system 400 may further include other optically detectable reporter probes capable of constitutively emitting at the third wavelength or at a fourth wavelength in response to amplification of the first bacterial nucleic acid sequence in the test sample and/or the second bacterial nucleic acid sequence in the test sample, a capable of constitutively emitting the third wavelength. Non-limiting examples include a donor-acceptor pair or fluorophore-quencher pair capable of constitutively emitting at the third wavelength or at a fourth wavelength in response to an amplification reaction and have been described above herein.

In some embodiments, system 400 for multiplexed detection of two or more bacterial nucleic acid sequences further includes one or more reaction reagents for performing the multiplexed detection of the two or more bacterial nucleic acid sequences in the test sample. In an aspect, the one or more reaction reagents include one or more reaction reagents for amplification of the two or more bacterial nucleic acid sequences in the test sample. For example, the one or more reaction reagents can include one or more reagents for performing polymerase chain reaction (PCR) amplification such as, e.g., a DNA polymerase (e.g., Taq polymerase), deoxynucleoside triphosphates or deoxynucleotide triphosphates (dNTPs), a buffer solution, bivalent cations (e.g., magnesium or manganese ions), and monovalent cations (e.g., potassium ions). In an aspect, the one or more reaction reagents comprise one or more reagents suitable for performing isothermal amplification. For example, the one or more reaction reagents can include reagents for performing recombinase polymerase amplification (RPA), loop-mediated isothermal amplification (LAMP), nucleic acid sequence based amplification (NASBA), helicase-dependent amplification (HAD), and nicking enzyme amplification reaction (NEAR). For example, the one or more reaction reagents can include, but are not limited to, one or more of a reverse transcriptase, an RNase, an RNA polymerase, a ligase, a recombinase, a single-stranded DNA-binding protein, a strand displacing polymerase, a helicase, an endonuclease. In some embodiments, the one or more reaction reagents include one or more reagents for lysing bactera. For example, the reaction reagents can include enzymes (e.g., lysozyme, lysostaphin) and detergents (e.g., NP-40, sodium deoxycholate).

In an aspect, system 400 for multiplexed analysis of two or more bacterial nucleic acid sequences in a test sample includes more than two sets of particles. In an aspect, system 400 includes three, four, five, six, seven, eight, nine, ten, eleven, twelve, thirteen, fourteen, fifteen, sixteen, seventeen, eighteen, nineteen, or twenty sets of particles, each set of particles includes an amplification primer set and a fluorescent identifier.

In an aspect, system 400 includes at least one third set of particles, each particle of the at least one third set of particles degradable in response to at least one of the first, the second, or a third temperature condition and having associated therewith a third amplification primer set and a third fluorescent identifier capable of emitting at a fourth wavelength, the third amplification primer set selected to specifically interact with a third bacterial nucleic acid sequence, and the third fluorescent identifier indicative of the third amplification primer set; and wherein the at least one fluorescent intercalating agent is capable of constitutively emitting at the third wavelength in response to amplification of the first bacterial nucleic acid sequence in the test sample, the second bacterial nucleic acid sequence in the test sample, and/or the third bacterial nucleic acid sequence in the test sample; and wherein the first wavelength, the second wavelength, the third wavelength, and the fourth wavelength are optically discernable from one another. In an aspect, the first, second, and third temperature condition is the same temperature condition.

Described herein is a system for multiplexed analysis of antibiotic resistance in a bacterial sample. The system includes two or more sets of particles including a first set of particles, each particle of the first set of particles degradable in response to a first environmental condition and having associated therewith a first antibiotic and a first optically detectable identifier capable of emitting a first wavelength, the first antibiotic having at least one of bactericidal or bacteriostatic activity against a first subset of bacteria, and the first optically detectable identifier indicative of the first antibiotic; and at least one second set of particles, each particle of the at least second set of particles degradable in response to a second environmental condition and having associated therewith a second antibiotic and a second optically detectable identifier capable of emitting a second wavelength, the second antibiotic having at least one of bactericidal or bacteriostatic activity against a second subset of bacteria, and the second optically detectable identifier indicative of the second antibiotic; and at least one optically detectable reporter probe capable of constitutively emitting a third wavelength in response to viability of bacteria in the bacterial sample.

FIG. 5 illustrates a non-limiting example of a system 500 for multiplexed analysis of antibiotic resistance in a bacterial sample. System 500 includes two or more sets of particles 505 and at least one optically detectable reporter probe 530. The two or more sets of particles 505 include a first set of particles 510 and at least one second set of particles 520. Particles 512a, 512b, 512c, 512d, 512e, and 512f are representative of particles in the first set of particles 510 and are degradable in response to a first environmental condition (e.g., temperature, pH, chemical reaction, electric field, or electromagnetic energy). Each of the particles 512a-512f include a first antibiotic 514 and a first optically detectable identifier 516. The first antibiotic 514 has at least one of bactericidal or bacteriostatic activity against a first subset of bacteria. First optically detectable identifier 516 is capable of emitting a first wavelength (as represented by the diagonal lines in particles 512a-512f) and is indicative of the first antibiotic 514. Particles 522a, 522b, 522c, 522d, 522e, and 522f are representative of particles in the at least one second set of particles 520 and are degradable in response to a second environmental condition. In some embodiments, the second environmental condition is the same as the first environmental condition. In other embodiments, the second environmental condition differs from the first environmental condition. Each of the particles 522a-522f includes a second antibiotic 524 and a second optically detectable identifier 526. Second antibiotic 524 has at least one of bactericidal or bacteriostatic activity against a second subset of bacteria. In some embodiments, the second subset of bacteria differs from first subset of bacteria. In other embodiments, the second subset of bacteria is identical to the first subset of bacteria. For example, system 500 can be configured for multiplexed analysis of bacterial resistance of a single subset or type of bacteria against multiple antibiotics, each antibiotic in its own set of particles with its own optically detectable identifier. Second optically detectable identifier 526 is capable of emitting a second wavelength (represented by the vertical line pattern in particles 522a-522f) and is indicative of the second antibiotic 524. At least one optically detectable reporter probe 530 is capable of constitutively (as shown by arrow 532) emitting a third wavelength 534 (represented by the cross-hatched lines) in response to viability of bacteria in the bacterial sample.

System 500 is configured for multiplexed analysis of antibiotic resistance in a bacterial sample. The bacterial sample can include a sample taken from a subject, e.g., a mammalian subject, and can include a sample from a bodily fluid, a tissue, or a swab. Alternatively, the bacterial sample can include a sample taken from an environmental source, e.g., water, air, soil, a surface, food, beverage, medicine, or other component of the environment.

The two or more sets of particles 505 of system 500 for multiplexed analysis of antibiotic resistance in a bacterial sample include a first set of particles 510 including a first antibiotic 514 having bactericidal or bacteriostatic activity against a first subset of bacteria and at least one second set of particles 520 including second antibiotic 524 having bactericidal or bacteriostatic activity against a second subset of bacteria. In an aspect, the subsets of bacteria include subsets of Gram positive bacteria, Gram negative bacteria, Mycobacteria, aerobic bacteria, anaerobic bacteria. In an aspect, a subset of bacteria includes a phylum of bacteria, a class of bacteria, an order of bacteria, a family of bacteria, a genus of bacteria, a species of bacteria, or a sub-species or strain of bacteria.

In an aspect, the first subset of bacteria and the second subset of bacteria are different subsets of bacteria. For example, the first subset of bacteria and the second subset of bacteria are part of a test sample derived from a bodily fluid, e.g., urine, or an environmental sample, e.g., a water sample. In an aspect, the first subset of bacteria and the second subset of bacteria are identical subsets of bacteria. For example, the test sample can include a defined subset of bacteria for use in the multiplexed analysis of antibiotic resistance. For example, the system for multiplexed analysis of antibiotic resistance can include two or more subsets of particles, each subset of particles including a different antibiotic for assessing antibiotic resistance against a specific bacteria or subset of bacteria.

In an aspect, the first subset of bacteria or the second subset of bacteria includes one or more strains of *Escherichia coli*. For example, the subset of bacteria can include one or more strains of *Escherichia coli* associated with gastrointestinal infection (e.g., O157:H7, O104:H4, and O104:H21). For example, the subset of bacteria can include one or more strains of *Escherichia coli* associated with urinary tract infection (e.g., uropathogenic *E. coli*).

In an aspect, the first subset of bacteria or the second subset of bacteria includes one or more species of *Mycobacterium*. In an aspect, the first subset of bacteria or the second subset of bacteria includes *Mycobacterium tuberculosis*. For example, the system can be designed for multiplexed analysis of antibiotic resistance of bacteria associated with tuberculosis. For example, the system can be designed for multiplexed analysis of antibiotic resistance against *Mycobacterium tuberculosis*. For example, each set of the two or more sets of particles can include a different antibiotic for testing against a sample containing strains of *Mycobacterium tuberculosis* or other disease causing *Mycobacterium*, non-limiting examples of antibiotic including isoniazid, rifampicin, bedaquiline, delamanid, streptomycin, clofazimine, ethambutol, pyrazinamide, linezolid, fluoroquinolones, ethionamide, capreomycin, and para-aminosalicylic acid. In an aspect, the first subset of bacteria or the second subset of bacteria includes one or more bacteria or strains of bacteria from the *Mycobacterium tuberculosis* complex (e.g., *M. africanum*, *M. bovis* BCG, *M. tuberculosis*, and *M. canetti*, to name just a few).

In an aspect, the first subset of bacteria and the second subset of bacteria includes one or more of methicillin resistant *Staphylococcus aureus*, methicillin susceptible *Staphylococcus aureus*, *Escherichia coli*, *Streptococcus pneumonia*, *Pseudomonas aeruginosa*, *Staphylococcus epidermidis*, *Salmonella enterica*, *Klebsiella pneumonia*, *Streptococcus pyogenes*, *Acinetobacter baumannii*, or *Enterococcus faecalis*. For example, the system can be designed for multiplexed analysis of antibiotic resistance of bacteria associated with sepsis.

System 500 for multiplexed analysis of antibiotic resistance in a bacterial sample includes a first set of particles 510 degradable in response to a first environmental condition and a second set of particles 520 degradable in response to a second environmental condition. In an aspect, the first environmental condition and the second environmental condition comprise at least one of temperature, pH, chemical reaction, electric field, or electromagnetic energy. For example, the first set of particles and the at least one second set of particles can be degradable in response to a change in at least one of temperature, pH, chemical reaction, electric field, or electromagnetic energy. For example, the first set of particles and the at least one second set of particles can be formed from materials that are degradable in response to a change in at least one of temperature, pH, chemical reaction, electric field, or electromagnetic energy.

In some embodiments, the first environmental condition and the second environmental condition are identical environmental conditions. For example, the first set of particles and the at least one second set of particles can be degradable in response to identical environmental conditions, for example, an identical condition of temperature, pH, chemical reaction, electric field, and/or electromagnetic energy. For example, the first set of particles and the at least one second set of particles can be formed from materials that are degradable in response to identical environmental conditions of temperature, pH, chemical reaction, electric field, and/or electromagnetic energy.

In an aspect, the particles of the first set of particles 510 and of the at least one second set of particles 520 include a structure formed from a degradable material that is degradable in response to at least the first environmental condition or the second environmental condition. In an aspect, the particles of the first set of particles 510 and of the at least one second set of particles 520 include a structure formed from a degradable gel. In an aspect, the particles of the first set of particles 510 and of the at least one second set of particles 520 include a structure formed from low melt agarose. In an aspect, the particles of the first set of particles 510 and of the at least one second set of particles 520 include a structure formed from a degradable alginate. In an aspect, the particles of the first set of particles 510 and of the at least one second set of particles 520 include a structure formed from a degradable sugar. In an aspect, the particles of the first set of particles 510 and of the at least one second set of particles 520 include a structure formed from a temperature-responsive degradable material. In an aspect, the particles of the first set of particles 510 and of the at least one second set of particles 520 include a structure formed from a pH-responsive degradable material. In an aspect, the particles of the first set of particles 510 and of the at least one second set of particles 520 include a structure formed from a chemically-responsive degradable material. In an aspect, the particles of the first set of particles 510 and of the at least one second set of particles 520 include a structure formed from an electric field-responsive degradable material. In an aspect, the particles of the first set of particles 510 and of the at least one second set of particles 520 include a structure formed from an electromagnetic energy-responsive degradable material. Non-limiting examples of environmental condition-responsive degradable materials for forming the particles of the two or more sets of particles are presented above herein.

The two or more sets of particles 505 are designed or selected for use in a multiplex analysis of antibiotic resistance. In some embodiments, the multiplex analysis of antibiotic resistance includes performing reactions in aqueous-in-oil droplets or an emulsion system. In an aspect, at least a portion of the particles of the first set of particles 510 and of the at least one second set of particles 520 are distributable into an aqueous portion of aqueous-in-oil droplets or emulsion. In an aspect, the particles of the first set of particles 510 and of the at least one second set of particles 520 are hydrophilic. In an aspect, the particles of the first set of particles 510 and of the at least one second set of particles 520 include a structure at least partially formed from a hydrophilic material. Non-limiting examples hydrophilic material for use in forming degradable particles have been described above herein.

System 500 for multiplexed analysis of antibiotic resistance in a bacterial sample includes two or more sets of particles 505 including a first set of particles 510 including a first antibiotic 514 and at least one second set of particles 520 including a second antibiotic 524. The first antibiotic 514 and the second antibiotic 524 can include any of a number of antibiotic reagents having bactericidal activity (i.e., kills bacteria) or bacteriostatic activity (i.e., inhibits bacterial growth). Non-limiting examples of antibiotics specific for Gram-negative bacteria, Gram-positive positive bacteria, Mycobacterium, and with narrow spectrum or broad-spectrum of reactivity include aminoglycosides, ansamycins, carbapenems, aminoglycosides, clindamycin, trimethoprim, cephalosporins, glycopeptides, lincosamides, macrolides, beta-lactams, monobactams, tetracyclines, sulfonamides, quinolones, penicillins, nitrofurans, and oxazolidinones. In an aspect, the antibiotics can include any of a number of antibiotics used in the treatment of tuberculosis, non-limiting examples of which include capreomycin, cycloserine, ethambutol, ethionamide, isoniazid, pyrazinamide, rifampicin, rifabutin, rifapentine, and streptomycin. Other non-limiting examples of antibiotics include chloramphenicol, fosfomycin, fusidic acid, metronidazole, thiamphenicol, and tigecycline. It is also anticipated that new antibiotics in development or not yet described can be incorporated into the two or more sets of particles of the system.

System 500 for multiplexed analysis of antibiotic resistance in a bacterial sample includes a first set of particles 510 including a first optically detectable identifier 516 capable of emitting a first wavelength, at least one second set of particles 520 including a second optically detectable identifier 526 capable of emitting a second wavelength, and at least one optically detectable reporter probe 530 capable of constitutively emitting a third wavelength. In an aspect, the first wavelength emitted by the first optically detectable identifier 516 is a first detectable color, the second wavelength emitted by the second optically detectable identifier 526 is a second detectable color, and the third wavelength constitutively emitted by the at least one optically detectable reporter probe 530 is a third detectable color. In an aspect, the first wavelength, the second wavelength, and the third wavelength are optically discernable from one another. In an aspect, the first wavelength, the second wavelength, or the third wavelength is an ultraviolet wavelength or wavelength band of electromagnetic energy. In an aspect, at least one of the first wavelength, the second wavelength, or the third wavelength is a visible wavelength or wavelength band of electromagnetic energy. In an aspect, the first wavelength, the second wavelength, or the third wavelength is a near infrared wavelength or wavelength band of electromagnetic energy.

In an aspect, the first optically detectable identifier 516 is a first colored dye or pigment and the second optically detectable identifier 526 is a second colored dye or pigment. In an aspect, the first optically detectable identifier 516 is a first fluorophore capable of emitting fluorescence at the first wavelength and the second optically detectable identifier 526 is a second fluorophore capable of emitting fluorescence at the second wavelength. In an aspect, the first optically detectable identifier 516 is a first quantum dot capable of emitting the first wavelength and the second optically detectable identifier 526 is a second quantum dot capable of emitting the second wavelength. Non-limiting examples of dyes, pigments, fluorophores, colored and fluorescent particles, and quantum dots have been described above.

System 500 for multiplexed analysis of antibiotic resistance in a bacterial sample includes at least one optically detectable reporter probe 530 capable of constitutively emitting a third wavelength in response to viability of bacteria in the bacterial sample. In some embodiments, the at least one optically detectable reporter probe 530 is associated with each particle of the first set of particles 510 and with each particle of the at least one second set of particles 520. In some embodiments, the at least one optically detectable reporter probe 530 includes a first optically detectable reporter probe specific for viability of the first subset of bacteria and a second optically detectable reporter probe specific for viability of the second subset of bacteria. For example, a first optically detectable reporter probe can include a bacteriophage specific for the first subset of bacteria and a second optically detectable reporter probe can include a second bacteriophage specific for the second subset of bacteria, wherein each bacteriophage type includes a luciferase reporter gene for constitutively emitting the third wavelength in response to infecting their respective bacteria subsets. In this instance, the two different reporter probes constitutively emit the same wavelength, i.e., the third wavelength, while the optically detectable identifiers provide an indication of which antibiotics are present in a given droplet.

In an aspect, the at least one optically detectable reporter probe 530 comprises a donor-acceptor pair capable of constitutively emitting the third wavelength. In an aspect, the at least one optically detectable reporter probe 530 comprises a fluorophore-quencher pair capable of constitutively emitting the third wavelength. For example, the optically detectable reporter probe can include a donor-acceptor pair/fluorophore-quencher pair capable or constitutively emitting the third wavelength in response to viability of bacteria in the bacterial sample. For example, the optically detectable reporter probe can include a fluorophore-quencher pair in which the quencher molecule quenches fluorescence emitted by the fluorophore as long as the pair are in close proximity by the process of FRET. In an aspect, the at least one optically detectable reporter probe includes an antibody, aptamer, or other binding entity including a fluorophore-quencher pair. For example, the at least one optically detectable reporter probe can include an antibody with a fluorophore and a quencher in close proximity to one another which separate in response to either degradation of the antibody upon cellular internalization or a conformational change in the antibody when it binds to its specific target. Non-limiting examples of fluorophore-quencher pairs with antibodies, oligonucleotide, or aptamer substrates have been described above herein.

In an aspect, the at least one optically detectable reporter probe 530 comprises a DNA intercalating agent capable of constitutively emitting the third wavelength. For example, the optically detectable reporter probe can include a DNA intercalating agent capable of constitutively emitting the third wavelength in response to viability of bacteria in the bacterial sample. Non-limiting examples include ethidium bromide, propidium iodide, DAPI, SYTO-9, SYTO-13, SYTO-82, SYBR Green 1, SYBR Gold, EvaGreen, and acridine orange. In some embodiments, the DNA intercalating agent is capable of entering a viable bacterial cell. In some embodiments, the DNA intercalating agent is only able to enter a bacterial cell with a compromised cell membrane, i.e., a dead or dying bacterial cell. In an aspect, the at least one optically detectable reporter probe 530 comprises a probe of membrane integrity capable of constitutively emitting the third wavelength. For example, the optically detectable reporter probe can include a DNA intercalating dye or vital dye that is capable of entering and concentrating in bacteria once the membrane has become compromised as a result of cell death.

In an aspect, the at least one optically detectable reporter probe 530 comprises a bacteriophage with a reporter gene. For example, the optically detectable reporter probe can include a bacteriophage with a reporter gene capable of constitutively emitting the third wavelength in response to viability of bacteria in the bacterial sample. For example, a reporter gene or genes can be incorporated into the phage genome and upon infection of bacteria, the reporter gene(s) carried by the bacteriophage is expressed. As such, bacteriophage including a reporter gene can be used as an indicator of bacterial viability. In an aspect, the reporter probe is a bacteriophage with a broad spectrum of bacterial infection. In an aspect, the reporter probe is a bacteriophage with a narrow spectrum of bacterial infection. Additional information regarding the breadth of bacteriophage can be found on various database websites, non-limiting examples of which have been cited above herein.

In an aspect, the at least one optically detectable reporter probe 530 comprises a bacteriophage including a reporter gene that generates a colorimetric, fluorescent, chemiluminescent, or bioluminescent signal in response to infection and propagation of viable bacterial cells. In some instances, the response is spontaneous (e.g., autofluorescence associated with green fluorescent protein). In some instances, the response requires a substrate or cofactor, either endogenous or exogenous to the bacteria (e.g., when the reporter gene is an enzyme). Non-limiting examples of reporter genes include those encoding green, yellow or red fluorescent protein (GFP, YFP, or RFP, respectively), bacterial luciferase, firefly luciferase, beta-galactosidase (lacZ), chloramphenyl acetyltransferase (CAT), beta-glucuronidase (GUS). For other non-limiting examples of reporting via reporter genes, see, e.g., Smartt & Ripp (2011) *Anal. Bioanal. Chem.* 400:991-1007, which is incorporated herein by reference.

In an aspect, the at least one optically detectable reporter probe 530 comprises a substrate capable of constitutively emitting the third wavelength in response to interaction with an enzyme. In an aspect, the substrate is at least one of a chemical substrate, a lipid-based substrate, a peptide-based substrate, or a protein-based substrate. In an aspect, the interaction of the substrate with a target enzyme produces a colorimetric or fluorogenic product. In an aspect, the interaction of the substrate with a target enzyme is detected by chemiluminescence. In an aspect, the at least one optically detectable reporter probe includes a substrate for at least one of beta-glucuronidase, beta-glucosidase, beta-galactosidase, beta-lactamase, beta-glucuronidase, alkaline phosphatase, luciferase, cytochrome P450, deubiquitinating enzyme, kinase, phosphatase, lipase, phospholipase, protease, or peptidase. In an aspect, the at least one optically detectable reporter probe includes a substrate that interacts with a component of a cell membrane (e.g., lipids, proteins and protein receptors, and carbohydrates). A number of substrates which constitutively emit a wavelength in response to interaction with an enzymatic target are available from commercial sources (from, e.g., Thermo Fisher Scientific, Waltham, Mass.).

In an aspect, the at least one optically detectable reporter probe 530 includes a substrate for beta-glucuronidase capable of constitutively emitting the third wavelength in response to viability of bacteria in the bacterial sample. For example, the substrate for beta-glucuronidase can include a substrate that generates a colorimetric precipitate in response to the interaction, non-limiting examples of which have been described above herein. For example, the substrate for beta-glucuronidase can include a substrate that generates a fluorogenic product in response to the interaction, a non-limiting example of which 4-methylumbelliferyl-β-D-glucuronide (MUG).

In an aspect, the at least one optically detectable reporter probe 530 includes a substrate for beta-galactosidase capable of constitutively emitting the third wavelength in response to viability of bacteria in the bacterial sample. For example, the substrate for beta-galactosidase can include a substrate that generates a colorimetric precipitate in response to the interaction, non-limiting examples of which have been described above herein. For example, the substrate of beta-galactosidase can include a substrate that generates a fluorogenic product in response to the interaction, a non-limiting example of which includes 4-methyl-umbelliferyl-β-D-galactosidase.

In some embodiments, system 500 for multiplexed analysis of antibiotic resistance in a bacterial sample includes one or more reaction reagents for performing the multiplexed analysis. In an aspect, system 500 includes one or more components of a culture medium for growing bacteria. For example, the one or more reaction reagents can include components of a growth, nutrient, or culture medium for culturing cells and can be either synthetic or chemically defined or non-synthetic or chemically undefined. The culture or growth medium can include components to support growth of bacteria and may include a carbon source (e.g., glucose), various salts, and a source of amino acids and nitrogen. In some embodiments, the culture, nutrient, or growth medium includes a selective medium for selective growth of a type(s) of cell. In some embodiments, the culture, nutrient, or growth medium includes a differential or indicator medium for detecting selective growth of a type(s) of cell. The one or more reaction reagents can include any of a number of nutrients, amino acids, lipids, carbohydrates, sugars, and salts necessary to promote growth of bacteria. The one or more reaction reagents can further include one or more reagents for lysing bacteria, e.g., lysozyme.

In an aspect, system 500 for multiplexed analysis of antibiotic resistance in a bacterial sample includes more than two sets of particles. In an aspect, system 500 includes three, four, five, six, seven, eight, nine, ten, eleven, twelve, thirteen, fourteen, fifteen, sixteen, seventeen, eighteen, nineteen, or twenty sets of particles, each set of particles includes an antibiotic and an optically detectable identifier.

In an aspect, system 500 includes at least one third set of particles, each particle of the at least one third set of particles degradable in response to at least one of the first, the second, or a third environmental condition and having associated therewith a third antibiotic and a third optically detectable identifier capable of emitting a fourth wavelength, the third antibiotic having at least one of bactericidal or bacteriostatic activity against a third subset of bacteria, and the third optically detectable identifier indicative of the third antibiotic; and wherein the at least one optically detectable reporter probe is capable of constitutively emitting the third wavelength in response to viability of bacteria in the bacterial sample; and wherein the first wavelength, the second wavelength, the third wavelength, and the fourth wavelength are discernable or distinguishable from one another. In an aspect, the first, second, and third environmental condition is the same environmental condition (e.g., temperature, pH, chemical reaction, electric field, or electromagnetic energy). In an aspect, the third subset of bacteria is identical to the first and second subset of bacteria, such that a single subset of bacteria is assessed for antibiotic resistance against the first, second, and the at least third antibiotic in the system.

Described herein is a system configured for multiplexed analysis of two or more antigens in a test sample. In an embodiment, the system for multiplexed analysis of two or more antigens includes two or more sets of particles including a first set of particles, each particle of the first set of particles degradable in response to a first environmental condition and having associated therewith a first antibody set and a first optically detectable identifier capable of emitting a first wavelength, the first antibody set including two or more antibodies specific for proximal targets on a first antigen, wherein the two or more antibodies of the first antibody set include modifications capable of interacting in an antibody-based proximity assay, and the first optically detectable identifier indicative of the first antibody set; and at least one second set of particles, each particle of the at least one second set of particles degradable in response to a second environmental condition and having associated therewith a second antibody set and a second optically detectable identifier capable of emitting a second wavelength, the second antibody set including two or more antibodies specific for proximal targets on a second antigen, wherein the two or more antibodies of the second antibody set include modifications capable of interacting in an antibody-based proximity assay, and the second optically detectable identifier indicative of the second antibody set; and at least one optically detectable reporter probe capable of constitutively emitting a third wavelength in response to the two or more antibodies of the first antibody set binding to their proximal targets on the first antigen and/or the two or more antibodies of the second antibody set binding to their proximal targets on the second antigen.

FIG. 6 illustrates a non-limiting example of a system for multiplexed analysis of two or more antigens in a test sample. System 600 includes two or more sets of particles 605 and at least one optically detectable reporter probe 630. The two or more sets of particles 605 include a first set of particles 610 and at least one second set of particles 620. Particles 612*a*, 612*b*, 612*c*, 612*d*, 612*e*, and 612*f* are representative of particles in the first set of particles 610 and are degradable in response to a first environmental condition (e.g., temperature, pH, chemical reaction, electric field, or electromagnetic energy). Each of the particles 612*a*-612*f* include a first antibody set 614 and a first optically detectable identifier 616. The first antibody set 614 includes two or more antibodies specific for proximal targets on a first antigen, wherein the two or more antibodies of the first antibody set 614 include modifications capable of interacting in an antibody-based proximity assay. First optically detectable identifier 616 is capable of emitting a first wavelength (as represented by the vertical line pattern in particles 612*a*-612*f*) and is indicative of the first antibody set. Particles 622*a*, 622*b*, 622*c*, 622*d*, 622*e*, and 622*f* are representative of particles in the at least one second set of particles 620 and are degradable in response to a second environmental condition. In some embodiments, the second environmental condition is the same as the first environmental condition. In other embodiments, the second environmental condition differs from the first environmental condition. Each of the particles 622*a*-622*f* includes a second antibody set 624 and a second optically detectable identifier 626. Second antibody set 624 includes two or more antibodies specific for proximal targets on a second antigen, wherein the two or more antibodies of the second antibody set 624 include modifications capable of interacting in an antibody-based proximity assay. Second optically detectable identifier 626 is capable of emitting a second wavelength (represented by the horizontal line pattern in particles 622*a*-622*f*) and is indicative of the second antibody set. System 600 further includes at least one optically detectable reporter probe 630 capable of constitutively (as shown by arrow 632) emitting a third wavelength 634 (represented by the cross-hatched lines) in response to the two or more antibodies of the first antibody set 614 binding to their proximal targets on the first antigen and/or the two or more antibodies of the second antibody set 624 binding to their proximal targets on the second antigen.

In an aspect, the two or more antigens in the test sample are free in solution. In an aspect, the two or more antigens in the test sample are located on the surface of one or more cell types in the test sample. For example, the two or more antigens can be associated with blood derived cells (e.g., two or more antigens in or on red blood cells, platelets, white blood cells, etc.). For example, the two or more antigens can be associated with malignant cells (e.g., human epidermal growth factor receptor type 2 (Her2/neu) and carcinoembryonic antigen).

In an aspect, at least the first antibody set 614 or the second antibody set 624 comprises at least one polyclonal antibody. For example, each antibody set can include a polyclonal antibody which by definition includes a collection of immunoglobulins which may react with different epitopes (i.e., different targets) on the same antigen. In an aspect, the first antibody set 614 includes one or more first polyclonal antibodies specific for proximal targets on the first antigen and the second antibody set 624 includes one or more second polyclonal antibodies specific for proximal targets on the second antigen. In an aspect, at least the first antibody set 614 or the second antibody set 624 comprises two or more monoclonal antibodies. For example, each antibody set can include two or more monoclonal antibodies, each of which binds to different epitopes on the same antigen. In an aspect, the first antibody set 614 includes two or more monoclonal antibodies specific for proximal targets on the first antigen and the second antibody set 624 includes two or more monoclonal antibodies specific for proximal targets on the second antigen.

The two or more antibodies of the first antibody set 614 and of the second antibody set 624 include modifications capable of interacting in an antibody-based proximity assay. The modifications can include a pair of molecules, wherein a first molecule of the pair is associated with one of the two or more antibodies and the second molecule of the pair is associated with a second of the two or more antibodies. When the first molecule and the second molecule come in contact with one another by virtue of the respective antibodies binding to their targets, the first molecule and the second molecule are able to interact. In some embodiments, the modification to the antibodies is a covalent modification. For example, the pair of molecules can be covalently attached to the antibodies through a cross-linking agent(s), non-limiting examples of which include NETS-ester, imidoester, maleimide, pyridyldithiol, hydrazide, and carbodiimide reactive groups (see, e.g., Thermo Fisher Scientific for an extensive listing of cross-linking agents). In some embodiments, the modification to the antibodies is a non-covalent modification. For example, the pair of molecules can be non-covalently attached to the antibodies through an avidin/biotin binding interaction.

In an aspect, the two or more antibodies of the first antibody set 614 and the two or more antibodies of the second antibody set 624 include oligonucleotide modifications. For example, the modifications can include a pair of oligonucleotides, wherein a first oligonucleotide of the pair is associated with one of the two or more antibodies of a given set of antibodies and the second oligonucleotide of the pair is associated with a second of the two or more antibodies of that given set of antibodies. When the first oligonucleotide and the second oligonucleotide come in contact with one another by virtue of the respective antibodies binding to their targets, the first oligonucleotide and the second oligonucleotide are able to interact. In an aspect, a first antibody of the two or more antibodies of an antibody set is modified with a first oligonucleotide and a second antibody of the two or more antibodies of the antibody set is modified with a second oligonucleotide, wherein the first oligonucleotide and the second oligonucleotide are capable of interacting with one another when the first antibody and the second antibody bind their respective proximal targets on an antigen. In an aspect, the oligonucleotide modifications form a template for amplification when in close proximity. In an aspect, the oligonucleotide modifications are capable of undergoing a ligation reaction when in close proximity. For example, when a first oligonucleotide associated with one of the two or more antibodies of an antibody set and a second oligonucleotide associated with a second of the two or more antibodies of the antibody set come into proximity to one another by virtue of the antibodies binding their respective proximal targets, a ligation assay can be performed to connect the first and second oligonucleotides to form a single oligonucleotide for use as an amplification target. See, e.g., Greenwood, et al. (2015) *Biomolecular Detection Quantification* 4:10-16, which is incorporated herein by reference. In this instance, the at least one optically detectable reporter probe can include a DNA intercalating dye, e.g., EvaGreen, that can be used to detect formation of an amplification product from the ligated oligonucleotide template.

In an aspect, the oligonucleotide modifications are capable of hybridizing to one another when in close proximity. For example, when a first oligonucleotide associated with one of the two or more antibodies of a given set of antibodies and a second oligonucleotide associated with a second of the two or more antibodies of the given set of antibodies come into proximity to one another by virtue of the antibodies binding their respective proximal targets, at least a portion of the first and second oligonucleotides are capable of hybridizing to one another to create a double stranded DNA. The overlapped double stranded DNA can be extended using standard amplification procedures. Amplification can be monitored by an optically detectable reporter probe that is a DNA intercalating dye, non-limiting examples of which have been described above herein.

In an aspect, the two or more antibodies of the first antibody set 614 and the two or more antibodies of the second antibody set 624 include at least one donor-acceptor pair. In an aspect, a donor molecule is incorporated into a first antibody of an antibody set and an acceptor molecule is incorporated into a second antibody of the antibody set. When the first antibody and the second antibody bind to proximal targets on the surface of a cell, the donor molecule and the acceptor molecule are able to come into close contact and interact with one another. In an aspect, the donor molecule is capable of being excited by a stimulus (e.g., light, pH, temperature) causing a reaction (usually emission of some specific wavelength of light) to occur from the acceptor molecule if the donor and the acceptor are in close proximity. In an aspect, the donor-acceptor pair includes a fluorophore-quencher pair, wherein a fluorophore molecule is incorporated into a first antibody of an antibody set and a quencher molecule is incorporated into a second antibody of the antibody set and upon binding of the first antibody and the second antibody to their respectively proximal targets, the fluorophore is quenched. Non-limiting examples of donor-acceptor pairs and fluorophore-quencher pairs have been described above herein.

System 600 for multiplexed analysis of two or more antigens in a test sample includes a first set of particles 610 degradable in response to a first environmental condition and at least one second set of particles 620 degradable in response to a second environmental condition. In an aspect, the first environmental condition and the second environmental condition comprises at least one of temperature, pH, chemical reaction, electric field, or electromagnetic energy. For example, the first set of particles and the at least one second set of particles can be degradable in response to a change in at least one of temperature, pH, chemical reaction, electric field, or electromagnetic energy. For example, the first set of particles and the at least one second set of particles can be formed from materials that are degradable in response to a change in at least one of temperature, pH, chemical reaction, electric field, or electromagnetic energy.

In some embodiments, the first environmental condition and the second environmental condition are identical environmental conditions. For example, the first set of particles and the at least one second set of particles can be degradable in response to identical environmental conditions, for example, an identical condition of temperature, pH, chemical reaction, electric field, and/or electromagnetic energy. For example, the first set of particles and the at least one second set of particles can be formed from materials that are degradable in response to identical environmental conditions of temperature, pH, chemical reaction, electric field, and/or electromagnetic energy.

In an aspect, the particles of the first set of particles 610 and of the at least one second set of particles 620 include a structure formed from a degradable material that is degradable in response to at least the first environmental condition or the second environmental condition. In an aspect, the particles of the first set of particles 610 and of the at least one second set of particles 620 include a structure formed from low melt agarose. In an aspect, the particles of the first set of particles 610 and of the at least one second set of particles 620 include a structure formed from at least one of a degradable gel, a degradable alginate, or a degradable sugar. In an aspect, the particles of the first set of particles 610 and of the at least one second set of particles 620 include a structure formed from a temperature-responsive material. In an aspect, the particles of the first set of particles 610 and of the at least one second set of particles 620 include a structure formed from at least one of a pH-responsive degradable material, a chemically-responsive degradable material, an electric field-responsive degradable material, or an electromagnetic energy-responsive degradable material. Non-limiting examples of environmental condition-responsive degradable materials for forming the particles of the two or more sets of particles are presented above herein.

The two or more sets of particles 605 include components for multiplex analysis two or more antigens. In some embodiments, the multiplex analysis of two or more antigens includes performing reactions in aqueous-in-oil droplets or an emulsion system. In an aspect, at least a portion of the particles of the first set of particles 610 and of the at least one second set of particles 620 are distributable into an aqueous portion of aqueous-in-oil droplets or emulsion. In an aspect, the particles of the first set of particles 610 and of the at least one second set of particles 620 are hydrophilic. In an aspect, the particles of the first set of particles 610 and of the at least one second set of particles 620 include a structure at least partially formed from a hydrophilic material. Non-limiting examples of hydrophilic material for use in forming hydrophilic degradable particles have been described above herein.

System 600 for multiplexed analysis of two or more antigens in a test sample includes a first set of particles 610 including a first optically detectable identifier 616 capable of emitting a first wavelength, at least one second set of particles 620 including a second optically detectable identifier 626 capable of emitting a second wavelength, and at least one optically detectable reporter probe 630 capable of constitutively emitting a third wavelength. In an aspect, the first wavelength emitted by the first optically detectable identifier 616 is a first detectable color, the second wavelength emitted by the second optically detectable identifier 626 is a second detectable color, and the third wavelength constitutively emitted by the at least one optically detectable reporter probe 630 is a third detectable color. In an aspect, the first wavelength, the second wavelength, and the third wavelength are optically discernable from one another. In an aspect, the first wavelength, the second wavelength, or the third wavelength is an ultraviolet wavelength or wavelength band of electromagnetic energy. In an aspect, at least one of the first wavelength, the second wavelength, or the third wavelength is a visible wavelength or wavelength band of electromagnetic energy. In an aspect, the first wavelength, the second wavelength, or the third wavelength is a near infrared wavelength or wavelength band of electromagnetic energy.

In an aspect, the first optically detectable identifier 616 is a first colored dye or pigment and the second optically detectable identifier 626 is a second colored dye or pigment. In an aspect, the first optically detectable identifier 616 includes a first fluorophore capable of emitting fluorescence at the first wavelength and the second optically detectable identifier 626 includes a second fluorophore capable of emitting fluorescence at the second wavelength. In an aspect, the first optically detectable identifier 616 is a first quantum dot capable of emitting the first wavelength and the second optically detectable identifier 626 is a second quantum dot capable of emitting the second wavelength. Non-limiting examples of dyes, pigments, fluorophores, colored or fluorescing particles, or quantum dots have been described above.

System 600 for multiplexed analysis of two or more antigens in a test sample includes at least one optically detectable reporter probe 630 capable of constitutively emitting a third wavelength in response to the two or more antibodies of the first antibody set 614 binding to their proximal targets on the first antigen and/or the two or more antibodies of the second antibody set 624 binding to their proximal targets on the second antigen. In some embodiments, the at least one optically detectable reporter probe 630 is associated with each particle of the first set of particles 610 and with each particle of the at least one second set of particles 620. In some embodiments, the at least one optically detectable reporter probe 630 includes a first optically detectable reporter probe for specifically signaling in response to the two or more antibodies of the first antibody set 614 binding their proximal targets on the first antigen and a second optically detectable reporter probe for specifically signaling in response to the two or more antibodies of the second antibody set 624 binding their proximal targets on the second antigen. For example, a first optically detectable reporter probe can include a first donor-acceptor pair modification to the two or more antibodies associated with the first set of antibodies 614 and a second optically detectable reporter probe can include a second donor-acceptor pair modification to the two or more antibodies associated with the second set of antibodies 624. In some instance, the first donor-acceptor pair of the first antibody set and the second donor-acceptor pair of the second antibody set are the same, emitting the same third wavelength in response to respective binding of the first antibody set to proximal targets on the first antigen and binding of the second antibody set to proximal targets on the second antigen. In this instance, the two different reporter probes constitutively emit the same wavelength indicative of antibody binding while the optically detectable identifier provides an indication of which antigen is present.

In an aspect, the at least one optically detectable reporter probe 630 comprises a donor-acceptor pair capable of constitutively emitting the third wavelength. In an aspect, a donor molecule of a donor-acceptor pair is incorporated into a portion of a first antibody and an acceptor molecule of the donor-acceptor pair is incorporated into a second antibody and upon binding of the first antibody and the second antibody to their respectively proximal targets, the donor is excited by a stimulus (e.g., light, pH, temperature) causing a reaction (usually emission of some specific wavelength of light) to occur from the acceptor if the donor and the acceptor are in close proximity.

In an aspect, the at least one optically detectable reporter probe 630 is capable of constitutively emitting the third wavelength in response to an amplification reaction. For example, the optically detectable reporter probe can detect amplification of oligonucleotide modifications to the two or more antibodies of an antibody set. Non limiting examples of optically detectable reporter probes for detecting amplification have been describe above herein. In an aspect, the at least one optically detectable reporter probe 630 includes a TaqMan-like probe capable of constitutively emitting the third wavelength. For example, the at least one optically detectable reporter probe can include a TaqMan probe configured to interact with the amplified nucleic acid sequence presented by the interaction of oligonucleotides on antibodies bound to proximal targets on a cell surface. In an aspect, the at least one optically detectable reporter probe 630 comprises a DNA intercalating agent capable of constitutively emitting the third wavelength. For example, the at least one optically detectable reporter probe can include EvaGreen or other intercalating dye capable of emitting a wavelength in response to binding to double stranded DNA.

In an aspect, system 600 for multiplexed analysis of two or more antigens in a test sample includes more than two sets of particles. In an aspect, system 600 includes three, four, five, six, seven, eight, nine, ten, eleven, twelve, thirteen, fourteen, fifteen, sixteen, seventeen, eighteen, nineteen, or twenty sets of particles, each set of particles includes an antibody set and an optically detectable identifier.

In an aspect, system 600 includes at least one third set of particles, each particle of the at least one third set of particles degradable in response to at least one of the first, the second, or a third environmental condition and having associated therewith a third antibody set and a third optically detectable identifier capable of emitting a fourth wavelength, the third antibody set including two or more antibodies specific for proximal targets on a third antigen, wherein the two or more antibodies of the third antibody set include modifications capable of interacting in an antibody-based proximity assay, and the third optically detectable identifier indicative of the third antigen; and wherein the at least one optically detectable reporter probe is capable of constitutively emitting the third wavelength in response to the two or more antibodies of the first antibody set binding to their proximal targets on the first antigen, the two or more antibodies of the second antibody set binding to their proximal targets on the second antigen, and/or the two or more antibodies of the third antibody set binding to their proximal targets on the third antigen.

In some embodiments, system 600 is configured for multiplexed analysis of two or more antigens on a surface of two or more cell types. In an aspect, each particle of the first set of particles 610 is degradable in response to the first environmental condition and has associated therewith a first antibody set including two or more antibodies specific for proximal targets on a surface of a first cell type, wherein the two or more antibodies of the first antibody set include modifications capable of interacting in an antibody-based proximity assay, and wherein the first optically detectable identifier capable of emitting the first wavelength is indicative of the first antibody set; wherein each particle of the at least one second set of particles 620 is degradable in response to the second environmental condition and has associated therewith a second antibody set including two or more antibodies specific for proximal targets on a surface of a second cell type, wherein the two or more second antibodies of the second antibody set include modifications capable of interacting in an antibody-based proximity assay, and wherein the second optically detectable identifier capable of emitting the second wavelength is indicative of the second antibody set; and wherein the at least one optically detectable reporter probe 630 is capable of constitutively emitting the third wavelength in response to the two or more antibodies of the first antibody set binding to their proximal targets on the surface of the first cell type and/or the two or more antibodies of the second antibody set binding to their proximal targets on the surface of the second cell type.

In an aspect, the two or more antigens in the test sample are located on the surface of one or more cell types in the test sample. For example, the two or more antigens can be associated with blood derived cells (e.g., red blood cells, platelets, white blood cells, etc.). In an aspect, the first cell type and the second cell type are immune cell types. For example, the first antibody set and the second antibody set can be selected or designed to bind antigens on the surface of immune cells. Non-limiting examples of immune cells include granulocytes (e.g., basophils, eosinophils, and neutrophils), mast cells, monocytes, macrophages, dendritic cells, lymphocytes (e.g., B cells and T cells), and NK cells. For example, the two or more antigens can be associated with malignant cells (e.g., human epidermal growth factor receptor type 2 (Her2/neu) and carcinoembryonic antigen).

In an aspect, the two or more antibodies of the first antibody set bind to the same antigen on the surface of the first cell type and the two or more antibodies of the second antibody set bind to the same antigen on the second cell type. For example, the two or more antibodies can be designed to bind different epitopes on the same antigen. In an aspect, the two or more antibodies of the first antibody set bind to different antigens that are proximal to one another on the surface of the first cell type and the two or more antibodies of the second antibody set bind to different antigens that are proximal to one another on the surface of the second cell type. For example, a subset of the two or more antibodies can be designed to bind one target on a cell, e.g., T-cell receptor, and a second subset of the two or more antibodies can be designed to bind a second proximal target on a cell, e.g., CD3, wherein the T-cell receptor and CD3 form a complex on the cell membrane in response to T-cell activation.

In some embodiments, a kit may be provided, containing one or more of the above composition. A "kit," as used herein, typically defines a package or an assembly including one or more of the compositions of the invention, and/or other compositions associated with the invention, for example, as previously described. In some embodiments, each kit includes two or more sets of particles and at least one optically detectable reporter probe, non-limiting aspects of which have been described herein. For example, a kit may include two or more sets of particles and at least one optically detectable reporter probe for multiplexed analysis of two or more targets in a test sample. For example, a kit may include two or more sets of particles and at least one optically detectable reporter probe for multiplexed analysis of two or more nucleic acid sequences in a test sample. For example, a kit may include two or more sets of particles and at least one optically detectable reporter probe for multiplexed analysis of antibiotic resistance in a bacterial sample. For example, a kit may include two or more sets of particles and at least one optically detectable reporter probe for multiplexed analysis of two or more antigens in a test sample.

In other embodiments, multiple kits may be combined to perform a multiplexed analysis. For example, a first kit may include at least one first set of particles and the at least one optically detectable reporter probe and at least one second kit may include at least one second set of particles and the at least one optically detectable reporter probe, wherein the first kit and the at least one second kit are combined to perform multiplexed analysis of two or more targets in a sample. In this way, kits containing specific sets of particles can be mixed and matched as appropriate for the multiplexed analysis.

Each composition of a kit, e.g., each set of particles and at least one optically detectable reporter probe, can be proved in liquid form (e.g., in solution), in solid form (e.g., a dried powder), etc. A kit may further include one or more emulsifiers, e.g., mineral oil, and/or surfactants for use in forming reaction droplets. A kit may further include other compositions, e.g., one or more reaction reagents, suitable for performing a reaction with the set of particles and the at least one optically detectable reporter probe. For example, the kit can include reaction reagents necessary to perform an amplification reaction. For example, the kit can include reaction reagents necessary to culture cells, e.g., mammalian cells or bacteria. A kit may further include instructions. For example, the kit may include instructions for the use, modification, mixing, diluting, preserving, administering, assembly, storage, packaging, and/or preparations of the compositions and/or other compositions associated with the kit. The instructions may be provided in any form recognizable by one of ordinary skill in the art as a suitable means for obtaining such instructions, e.g., written or published, verbal, audible, digital, optical, visual, or electronic communication (e.g., via the Internet or web-based communication).

Methods are described herein for multiplexed analysis. FIG. 7 provides a block diagram of a non-limiting example of a method 700 for multiplexed analysis of two or more targets in a test sample. Method 700 includes in block 710 combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first set of one or more target-specific reagents specific for a first target and a first optically detectable identifier capable of emitting a first wavelength indicative of the first set of one or more target-specific reagents, wherein each particle of the at least one second set of particles is degradable in response to a second environmental condition and has associated therewith a second set of one or more target-specific reagents specific for a second target and a second optically detectable identifier emitting a second wavelength indicative of the second set of one or more target-specific reagents, and wherein the at least one optically detectable reporter probe constitutively emits a third wavelength in response to reaction of the first set of one or more target-specific reagents with the first target in the test sample and/or to reaction of the second set of one or more target-specific reagents with the second target in the test sample; in block 720, forming a plurality of reaction droplets by adding an immiscible carrier fluid to the aqueous medium; in block 730 performing a reaction with the plurality of formed reaction droplets; in block 740, interrogating at least a portion of the plurality of formed reaction droplets for emission of the first wavelength indicative of the first set of one or more target-specific reagents, the second wavelength indicative of the second set of one or more target-specific reagents, and the third wavelength indicative of constitutive emission from the at least one optically detectable reporter probe; in block 750 reporting a number of the formed reaction droplets emitting both the first wavelength and the third wavelength; and in block 760 reporting a number of the formed reaction droplets emitting both the second wavelength and the third wavelength.

Method 700 provides steps for multiplexed analysis of two or more targets in a test sample. The two or more targets can include two or more specific targets in the test sample. The two or more targets can include two or more specific analytes in the test sample. For example, the two or more targets can include two or more specific DNA targets, RNA targets, protein targets, antigen targets, carbohydrate targets, lipid targets, and the like. For example, the two or more targets can further include oligonucleotides, peptides, receptors, cell surface markers, small molecule compounds, organic compounds, inorganic compounds. For example, the two or more targets can include two or more targets (e.g., DNA, RNA, protein, carbohydrate, lipid, and the like) associated with a specific cell type(s) (e.g., blood, body fluid, or tissue cells, bacteria, fungi, parasites, and the like).

Method 700 includes combining in an aqueous medium the test sample, one or more reaction reagents, a first set of particles, at least one second set of particles, and at least one optically detectable reporter probe. In an aspect, the aqueous medium comprises water. In an aspect, the aqueous medium comprises a physiological saline solution. For example, the aqueous medium can include a 0.9% solution of sodium chloride in water. In an aspect, the aqueous medium comprises a buffered solution. For example, the aqueous medium can include phosphate buffered saline (PBS). In an aspect, the aqueous medium comprises a cell culture medium. For example, the aqueous medium can include a cell culture medium appropriate for culture and growth of isolated mammalian cells. For example, the aqueous medium can include a nutrient rich medium or broth (e.g., Luria broth) appropriate for culture and growth of bacteria. For example, the aqueous medium can include a culture broth appropriate for culture and growth of other microorganisms (e.g., yeast or other fungi).

Method 700 includes in block 710 combining the test sample with an aqueous medium. In an aspect, the test sample is a complex test sample, including many components. In an aspect, the test sample is a simple or defined test sample, including just two or more components. In an aspect, the test sample includes at least a portion of a bodily fluid (e.g., blood, urine, lymph, sputum, cerebrospinal fluid, semen, saliva, synovial fluid, mucus, amniotic fluid, vaginal secretions, breast milk, bile, aqueous humor, gastric acid, pus, phlegm, feces, or other bodily fluid or secretion), a tissue sample (e.g., a biopsy sample), or a at least a portion of a swab sample (e.g., a swab sample taken from a surface of a body or body part. In some embodiments, the test sample includes an environmental sample (e.g., a sample of water, air, soil, a surface, food, beverage, medicine, and the like). In an aspect, the test sample has been processed in some manner prior to combining with the other reagents. For example, the test sample may be processed to extract DNA or RNA from the sample prior to combining with the other reagents. For example, the test sample may be processed to extract one or more of proteins, peptides, lipids, carbohydrates, or other cellular components prior to combining with the other reagents. In an aspect, the test sample is a defined sample including a defined population of targets. For example, the test sample can be formulated to contain a defined number and set of targets for use in the multiplexed analysis.

Method 700 includes in block 710 adding one or more reaction reagents to the aqueous medium. In an aspect, the one or more reaction reagents are necessary and/or sufficient for performing the multiplex analysis. In an aspect, the one or more reaction reagents include one or more reagents suitable for performing an amplification reaction. For example, the one or more reaction reagents can include one or more reagents for performing polymerase chain reaction (PCR) amplification such as, e.g., a DNA polymerase (e.g., Taq polymerase), deoxynucleoside triphosphates or deoxynucleotide triphosphates (dNTPs), a buffer solution, bivalent cations (e.g., magnesium or manganese ions), and monovalent cations (e.g., potassium ions). In an aspect, the one or more reaction reagents comprise one or more reagents suitable for performing isothermal amplification, non-limiting examples of which have been described above herein.

In an aspect, the one or more reaction reagents include one or more components of a growth or culture medium. For example, the one or more reaction reagents can include components of a growth or culture medium for culturing cells and can be either synthetic or chemically defined or non-synthetic or chemically undefined. The culture or growth medium can include components to support growth of microorganisms (e.g., bacteria or fungi) or cells (tissue culture cells or primary cells) and may include a carbon source (e.g., glucose), various salts, and a source of amino acids and nitrogen. In some embodiments, the culture or growth medium includes a selective medium for selective growth of a type(s) of cell. In some embodiments, the culture or growth medium includes a differential or indicator medium for detecting selective growth of a type(s) of cell. The one or more reaction reagents can include any of a number of nutrients, amino acids, lipids, carbohydrates, sugars, and salts necessary to promote growth of a given cell type(s).

In an aspect, the one or more reaction reagents include one or more reagents necessary or sufficient for performing a chemical reaction. In an aspect, the one or more reaction reagents include one or more reagents necessary or sufficient for an enzymatic reaction. For example, the reaction reagents can include a ligase and other reagents necessary to perform a ligation reaction. For example, the one or more reaction reagents can include enzymes, substrates, buffer, salts, ions, inorganic or organic co-factors, co-enzymes, and any other reagents necessary or sufficient for a given enzymatic reaction.

Method 700 further includes in block 720 forming a plurality of reaction droplets by adding an immiscible carrier fluid to the aqueous medium. The potential targets in the test sample as well as the two or more sets of particles and the at least one optically detectable reporter probe in the aqueous medium are stochastically distributed into the plurality of reaction droplets. The immiscible carrier fluid can include an oil, e.g., non-limiting examples of which include mineral oil, dioctyl phthalate (DOP), oleic acid, octamethyltrisiloxane (OMTS), fluorinated oils, perfluorinated oils, fluorocarbon oils (e.g., Fluorinert™ FC-40, from 3M Company, Minneapolis Minn.). In some embodiments, the immiscible carrier fluid further includes a surfactant. For example, the immiscible carrier fluid can include a fluorocarbon carrier oil with 0.01%-2% (v/v) of a surfactant. In an aspect, the surfactant may act as a detergent, wetting agent, emulsifier, foaming agent, and/or dispersant. Non-limiting examples of surfactants include Zonyl®FSO-100, ABIL®EM 90, Tween 20, Triton X-100, and SPAN 80.

In an aspect, method 700 includes forming the plurality of reaction droplets through bulk emulsion. For example, the plurality of reaction droplets can be formed by vigorously shaking the mixture of the aqueous medium and the immiscible carrier fluid. In some embodiments, the bulk emulsion by shaking can be done manually, e.g., vigorous shaking by hand. In some embodiments, the bulk emulsion by shaking can be done using a machine (e.g., a vortex mixer or sonicator) with more specific "shaking" (e.g., vortexing or sonication).

In an aspect, method 700 includes forming the plurality of reaction droplets through micro-emulsification or two-phase microfluidic flow-focusing. See, e.g., Gu, et al. (2011) *Int. J. Mol. Sci.* 12(4):2572-2597, which is incorporated herein by reference. For example, droplets of the aqueous medium including the sample, reaction reagents, two or more sets of particles, and the at least one optically detectable reporter probe dispersed in the immiscible carrier fluid, e.g., oil, can be formed using flow-focusing geometry. In an aspect, the plurality of reaction droplets are formed using a T-junction device. For example, the reaction droplets can be formed by flowing the aqueous medium through a microfluidic device by pumping or pressure and independently flowing in the immiscible carrier fluid at right angles (e.g., through a T junction) to the flow of the aqueous medium to pinch off aqueous droplets. In an aspect, the plurality of reaction droplets are formed using a flow focusing device. For example, the reaction droplets can be formed by flowing the aqueous medium through a central channel of a microfluidic device and flowing the immiscible carrier fluid through channels on both sides and at right angle to the flow of the aqueous medium prior to passing through a small orifice in the flow channel to focus and pinch off the droplets. Devices for generating droplet through two-phase microfluidic flow-focusing are commercially available (e.g., QX200 Droplet Generator from Bio-Rad Laboratories Inc., Hercules, Calif.; Model 1530 Monodisperse Droplet Generator from MSP Corporation, Shoreview, Minn.).

In an aspect, method 700 includes forming the plurality of reaction droplets using a microfluidic chip, e.g., using SlipChip or similar technology. See, e.g., Du et al. (2009) *Lab Chip* 9(16):2286-2292, which is incorporated herein by reference.

Method 700 further includes in block 730 performing a reaction with the plurality of formed reaction droplets. Reactions can include chemical, enzymatic, or biochemical reactions, binding reactions, proliferation reactions, and inhibition reactions. In an aspect, the method includes performing an amplification reaction. For example, the set of one or more target-specific reagents associated with each particle of the two or more sets of particles can include a set of amplification primers and the reaction reagents can include reagents sufficient for performing the amplification reaction. In an aspect, the amplification reaction comprises a polymerase chain reaction (PCR) amplification. In an aspect, the amplification reaction comprises an isothermal amplification reaction. Non-limiting examples of isothermal amplification reactions include recombinase polymerase amplification (RPA), loop-mediated isothermal amplification (LAMP), nucleic acid sequence based amplification (NASBA), helicase-dependent amplification (HAD), and nicking enzyme amplification reaction (NEAR).

Method 700 further includes in block 740 interrogating at least a portion of the plurality of formed reaction droplets for emission of at least the first wavelength indicative of the first set of one or more target-specific reagents, the second wavelength indicative of the second set of one or more target-specific reagents, and the third wavelength indicative of constitutive emission from the at least one optically detectable reporter probe. In some embodiments, interrogating the at least a portion of the plurality of reaction droplets includes interrogating each of the plurality of reaction droplets. In other embodiments, interrogating the at least a portion of the plurality of reaction droplets includes interrogating a representative portion or statistically significant portion of the plurality of reaction droplets to allow for extrapolation of the number and/or percentage of reaction droplets emitting the first, second, third wavelengths, and combinations thereof.

In an aspect, method 700 includes interrogating at least a portion of the plurality of formed reaction droplets using multiple lasers, light emitting diodes, and/or bandwidth filters to interrogate and report the reactions occurring on the interrogated portion of the reaction droplets. In an aspect, interrogation is performed on a planar surface (e.g., multi-welled plate or microscope slide). For example, at least a portion of the reaction droplets can be interrogated using light microscopy. For example, at least a portion of the reaction droplets can be interrogated using fluorescence microscopy with various filter cubes to allow detection of reaction droplets fluorescing at at least one of the first wavelength, the second wavelength, the third wavelength, or a combination thereof. For example, a representative sample of the reaction droplets can be placed on a microscope slide or similar planar substrate and analyzed for a first wavelength of fluorescence (e.g., red), a second wavelength of fluorescence (e.g., blue), and a third wavelength of fluorescence (e.g., green).

In an aspect, method 700 includes interrogating at least a portion of the plurality of formed reaction droplets using multiple lasers, light emitting diodes, and/or bandwidth filters and high-speed digital-signal processing to report the reactions occurring on each individual reaction droplet. For example, interrogating at least a portion of the plurality of reaction droplets for emission of the first, second, and third wavelengths can be performed using a form of droplet reader that includes a means for interrogating emissions, e.g., fluorescence, from reaction droplets. A non-limiting example of a droplet reader includes the QX200 Droplet Reader (from Bio-Rad Laboratories, Hercules, Calif.). In an aspect, the method includes interrogating at least a portion of the plurality of reaction droplets for emission of the first, second, and third wavelengths using flow cytometry.

In an aspect, method 700 includes interrogating at least a portion of the plurality of formed reaction droplets with electromagnetic energy. For example, the reaction droplets can be interrogated by shining a light or using ambient light to observe one or more emitted wavelengths, e.g., color(s), from each of the at least a portion of the reaction droplets. For example, the reaction droplets can be interrogated using a light microscope, either by manually counting the number of different colored reaction droplets or automatically by taking digital images of multiple fields and using signal processing to count the number of different colored reaction droplets.

In an aspect, method 700 includes directing a specific wavelength or wavelength band on the plurality of formed reaction droplets to elicit emission of a wavelength or wavelength band from the optically detectable identifiers and/or the optically detectable reporter probe associated with the reaction droplets. For example, each of the plurality of reaction droplets can be interrogated with electromagnetic energy from a laser (e.g., helium-neon or argon lasers) to elicit emission of fluorescence (e.g., red, green, yellow, or blue fluorescence) from one or more of the optically detectable identifiers and/or the optically detectable reporter probe associated with the reaction droplets. A laser for use in interrogating the reaction droplets can include a gas laser, a solid-state laser, a photonic crystal laser, a semiconductor laser (e.g., laser diodes), or dye lasers.

Method 700 includes in block 750 and 760 reporting results from interrogation of the at least a portion of the plurality of formed reaction droplets. Method 700 includes in block 750 reporting a number of the formed reaction droplets emitting both the first wavelength and the third wavelength. In an aspect, a reaction droplet emitting both the first wavelength and third wavelength can be classified as a positive droplet. For a given reaction droplet, emitting the first wavelength is an indication that at least one particle from the first set of particles is incorporated into the reaction droplet. That first wavelength is correlated with a first target. If that same reaction droplet emits the third wavelength, this indicates that the desired reaction occurred, e.g., amplification, and the desired target, e.g., the first target, is in fact present in the test sample and was amplified. Method 700 further includes in block 760 reporting a number of the formed reaction droplets emitting both the second wavelength and the third wavelength. Droplets emitting the second wavelength have at least one particle from the at least one second set of particles incorporated into the reaction droplet, wherein that second wavelength is correlated with a second target. Again, if the same droplet emits both the second wavelength and the third wavelength, it is an indication that the second target has been identified in the sample. In an aspect, a reaction droplet emitting both the second wavelength and third wavelength can be classified as a positive droplet indicative of the second target. In general, either manual counting or automated counting combined with signal processing is employed to count the number and/or percentage of reaction droplets emitting at least one of the first, second, and third wavelengths.

In an aspect, the method includes reporting the number of reaction droplets emitting the first and third wavelengths and a number of reaction droplets emitting the second and third wavelengths. For example, the reporting can include reporting a number of droplets emitting both a red fluorescence and a blue fluorescence and a number of droplets emitting both a green fluorescence and a blue fluorescence. In an aspect, reporting can include providing a percentage of reaction droplets interrogated emitting the first and third wavelengths and a percentage of reaction droplets interrogated emitting the second and third wavelengths. For example, the reporting can include reporting a percentage of droplets emitting both a red fluorescence and a blue fluorescence and a percentage of droplets emitting both a green fluorescence and a blue fluorescence. In an aspect, reporting can be numerical. For example, the reporting can include a number or percentage of positive droplets. In an aspect, reporting can be graphical. For example, the reporting can include a graphical representation (e.g., scatter blot, bar graph, etc.) representing of positive droplets.

In some embodiments, the method described in FIG. 7 is designed or configured for multiplexed analysis of two or more nucleic acid sequences in a test sample, such as illustrated in the block diagram of FIG. 8. FIG. 8 illustrates the steps of method 800 for multiplexed analysis of two or more nucleic acid sequence targets in a test sample. Method 800 includes in block 810, combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first amplification primer set selected to interact with a first nucleic acid sequence and a first optically detectable identifier capable of emitting a first wavelength indicative of the first amplification primer set, wherein each particle of the at least one second set of particles is degradable in response to a second environmental condition and has associated therewith a second amplification primer set selected to interact with a second nucleic acid sequence and a second optically detectable identifier emitting a second wavelength indicative of the second amplification primer set, and wherein the at least one optically detectable reporter probe is capable of constitutively emitting a third wavelength in response to amplification of the first nucleic acid sequence and/or the second nucleic acid sequence; in block 820, forming a plurality of reaction droplets by adding an immiscible carrier fluid to the aqueous medium; in block 830, performing an amplification reaction with the plurality of formed reaction droplets; in block 840, interrogating at least a portion of the plurality of formed reaction droplets for emission of the first wavelength indicative of the first amplification primer set, the second wavelength indicative of the second amplification primer set, and the third wavelength indicative of constitutive emission from the at least one optically detectable reporter probe in response to amplification of the first and/or the second nucleic acid sequence in the formed reaction droplets; in block 850, reporting a number of the formed reaction droplets emitting both the first wavelength and the third wavelength; and in block 860, reporting a number of the formed reaction droplets emitting both the second wavelength and the third wavelength.

In some embodiments, the method described in FIG. 7 is designed or configured for multiplexed analysis of two or more bacterial nucleic acid sequences in a test sample. The method can include combining in an aqueous medium the test sample, one or more reaction reagents, a first set of particles, at least one second set of particles, and at least one fluorescent intercalating agent, wherein each particle of the first set of particles is degradable in response to a first temperature condition and has associated therewith a first amplification primer set selected to interact with a first bacterial nucleic acid sequence and a first fluorescent identifier capable of emitting a first wavelength indicative of the first amplification primer set, wherein each particle of the at least one second set of particles is degradable in response to a second temperature condition and has associated therewith a second amplification primer set selected to interact with a second bacterial nucleic acid sequence and a second fluorescent identifier emitting a second wavelength indicative of the second amplification primer set, and wherein the at least one fluorescent intercalating agent is capable of constitutively emitting a third wavelength in response to amplification of the first bacterial nucleic acid sequence and/or the second bacterial nucleic acid sequence; forming a plurality of reaction droplets by adding an immiscible carrier fluid to the aqueous medium; performing an amplification reaction with the plurality of formed reaction droplets; interrogating at least a portion of the plurality of formed reaction droplets for emission of the first wavelength indicative of the first amplification primer set, the second wavelength indicative of the second amplification primer set, and the third wavelength indicative of constitutive emission from the at least one fluorescent intercalating agent in response to amplification of the first and/or the second bacterial nucleic acid sequence in the formed reaction droplets; reporting a number of the formed reaction droplets emitting both the first wavelength and the third wavelength; and reporting a number of the formed reaction droplets emitting both the second wavelength and the third wavelength.

In some embodiments, the method described in FIG. 7 is designed or configured for multiplexed analysis of antibiotic resistance in a bacterial sample, such as illustrated in the block diagram of FIG. 9. FIG. 9 illustrates the steps of method 900 for multiplexed analysis of antibiotic resistance in a bacterial sample. Method 900 includes in block 910, combining in an aqueous medium the bacterial sample, one or more reaction reagents, a first set of particles, at least one second set of particles, and at least one optically detectable reporter probe, wherein each particle of the first set of particles is degradable in response to a first environmental condition and has associated therewith a first antibiotic having at least one of bactericidal or bacteriostatic activity against a first subset of bacteria and a first optically detectable identifier capable of emitting a first wavelength indicative of the first antibiotic, wherein each particle of the at least one second set of particles is degradable in response to a second environmental condition and has associated therewith a second antibiotic having at least one of bactericidal or bacteriostatic activity against a second subset of bacteria and a second optically detectable identifier capable of emitting a second wavelength indicative of the second antibiotic, and wherein the at least one optically detectable reporter probe is capable of constitutively emitting a third wavelength in response to viability of bacteria in the bacterial sample; in block 920, forming a plurality of reaction droplets by adding an immiscible carrier fluid to the aqueous medium; in block 930, performing a reaction with the plurality of formed reaction droplets; in block 940, interrogating at least a portion of the plurality of formed reaction droplets for emission of the first wavelength indicative of the first antibiotic, the second wavelength indicative of the second antibiotic, and the third wavelength indicative of constitutive emission from the at least one optically detectable reporter probe in response to viability of bacteria in the bacterial sample; in block 950, reporting a number of the formed reaction droplets emitting both the first wavelength and the third wavelength; and in block 960, reporting a number of the formed reaction droplets emitting both the second wavelength and the third wavelength.

In an aspect, method 900 includes performing a reaction with the plurality of formed reaction droplets including a bacterial sample and antibiotics. In some embodiments, the reaction includes a proliferation assay in which the bacteria in the bacterial sample are allowed to proliferate or not depending upon their susceptibility to the antibiotics present in the multiplex assay.

In some embodiments, the method described in FIG. 7 is designed or configured for multiplexed analysis of two or more antigens in a test sample, such as illustrated in the block diagram of FIG. 10. FIG. 10 illustrates the steps of method 1000 for multiplexed analysis of two or more antigens in a test sample. Method 1000 includes in block 1010, combining in an aqueous medium the test sample, one or more reaction reagents, a first set of particles, at least one second set of particles, and at least one optically detectable reporter probe, wherein each particle of the first set of particles is degradable in response to a first environmental condition and has associated therewith a first antibody set and a first optically detectable identifier capable of emitting a first wavelength, the first antibody set including two or more antibodies specific for proximal targets on a first antigen, the two or more antibodies of the first antibody set including modifications capable of interacting in an antibody-based proximity assay, and the first optically detectable identifier indicative of the first antibody set, wherein each particle of the second set of particles is degradable in response to a second environmental condition and has associated therewith a second antibody set and a second optically detectable identifier capable of emitting a second wavelength, the second antibody set including two or more antibodies specific for proximal targets on a second antigen, the two or more antibodies of the second antibody set including modifications capable of interacting in an antibody-based proximity assay, and the second optically detectable identifier indicative of the second antibody set, and wherein the at least one optically detectable reporter probe is capable of constitutively emitting a third wavelength in response to the two or more antibodies of the first antibody set binding to their proximal targets on the first antigen and/or the two or more antibodies of the second antibody set binding to their proximal targets on the second antigen; in block 1020, forming a plurality of reaction droplets by adding an immiscible carrier fluid to the aqueous medium; in block 1030, performing a reaction with the plurality of formed reaction droplets; in block 1040, interrogating at least a portion of the plurality of formed reaction droplets for emission of the first wavelength indicative of the first antibody set, the second wavelength indicative of the second antibody set, and the third wavelength indicative of constitutive emission from the at least one optically detectable reporter probe in response to the two or more antibodies of the first antibody set binding to their proximal targets on the first antigen and/or the two or more antibodies of the second antibody set binding to their proximal targets on the second antigen; in block 1050, reporting a number of the formed reaction droplets emitting both the first wavelength and the third wavelength; and in block 1060, reporting a number of the formed reaction droplets emitting both the second wavelength and the third wavelength.

In an aspect, method 1000 includes performing a reaction with the plurality of formed reaction droplets including a test sample and sets of modified antibodies. In some embodiments, method 1000 includes performing an antibody-based proximity assay. For example, the reaction can include binding sets of antibodies modified with donor-acceptor pairs to their respective targets and measuring a signal from the donor-acceptor pair. In some embodiments, method 1000 includes performing an amplification reaction. For example, the reaction can include amplifying a template formed by hybridization of oligonucleotides associated with the antibody sets. In some embodiments, method 1000 includes performing a ligation reaction followed by an amplification reaction. For example, the reaction can include ligating the ends of an oligonucleotide pair associated with the antibody set together to form a template for amplification, e.g., PCR amplification or isothermal amplification.

Example 1: Forming Agarose Particles with Reagents

Described is a method for forming agarose particles including fluorescent FluoSpheres.

A 0.50% solution of agarose for forming the particles was generated as follows: 275 mg of low melt agarose (Sigma A9414) was added to 50 mL of water and heated in a microwave for 1 minute to dissolve the low melt agarose. 3.6 mL of the agarose solution was combined with 400 uL of FluoSphere F8801 (red fluorescing 580/605 nm; from Thermo Fisher Scientific, Waltham, Mass.) in a 4 mL glass vial. The solution of agarose/FluoSpheres was kept warm.

A mineral oil solution with 3% SPAN 80 was generated as follows: 120 uL of SPAN 80 surfactant was added to 3.88 mL of mineral oil and vigorously shaken to ensure proper mixing of the surfactant in the mineral oil.

Agarose particles were formed as follows using a Dolomite microfluidics system (Dolomite Microfluidics, Norwell, Mass.):

A remote chamber was heated on a hot plate at 130° C. Pumps for pumping mineral oil solution and the heated agarose solution were primed and connected to a microfluidics chip. The system was primed by flowing oil through the chip at 500 mbar. Agarose was then flowed into system and pressure adjusted to allow for formation of agarose droplets. The formed agarose particles were collected and stored in oil at 4° C.

To remove oil from the agarose particles, the agarose particles were diluted 1:50 in water, placed in an Amicon Ultra-0.5 Centrifugal Filter Device, and centrifuged at 14,000×g for 5 min. Filtration was repeated twice more with 1:50 dilution in water.

FIGS. 11A-11D show the formed agarose particles and the fluorescence associated with the FluoSphere F8801. FIG. 11A shows a brightfield microscope image at 200× magnification of formed agarose particles 1100 in mineral oil/SPAN 80. FIG. 11B shows a composite image of the brightfield image of FIG. 11A overlaid with a fluorescent image of the same field. In this grayscale image, the red fluorescence from the FluoSphere F8801 is seen as bright dots 1110 overlaid with the agarose particles 1100. FIG. 11C shows a brightfield microscope image at 200× magnification of formed agarose particles 1100 after multiple washings in water. FIG. 11D shows a composite image of the brightfield image of FIG. 11C overlaid with a fluorescent image of the same field. In this grayscale image, the red fluorescence from the FluoSphere F8801 is seen as bright dots 1110.

Example 2: Forming Reaction Droplets with Quantum Dots

Figure 12:
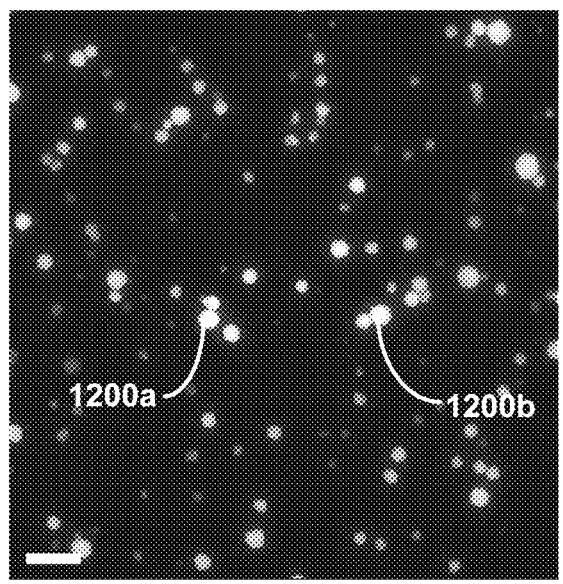
FIG. 12 shows a fluorescence microscope image at 200× magnification of the formed agarose particles with quantum dots.

Low melt agarose particles were formed as described above. CdSeS/ZnS alloyed quantum dots with fluorescence emission at 630 nm were added to the agarose during particle formation. FIG. 12 shows a fluorescent microscope image at 200× magnification of the formed agarose particles. The agarose particles are fluorescing due to the associated quantum dots as is represented by particles 1200*a* and 1200*b*.

Example 3: Amplification Reaction

Figure 13:
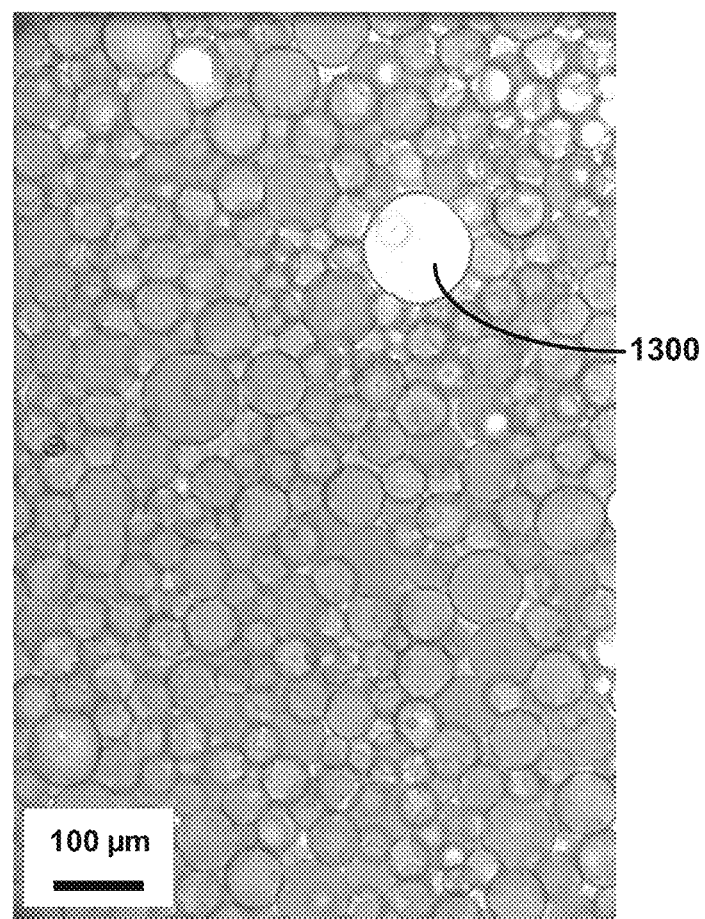
FIG. 13 shows a microscope image at 200× magnification of the formed reaction droplets post PCR amplification.

An amplification reaction was performed using reaction droplets. A set of particles was generated with low melt agarose as described above. The particles included forward and reverse amplification primers for the rodA gene of *E. coli* and CdSeS/ZnS alloyed quantum dots with fluorescence emission at 630 nm for the optically detectable identifier. The optically detectable reporter probe was a sequence specific probe with FAM fluorophore (fluorescence emission at 520; green) and BHQ1 quencher. FIG. 13 shows a microscope image at 200× magnification of the formed reaction droplets post PCR amplification. The bright reaction droplet 1300 is positive for amplification (i.e., has detectable fluorescence attributable to un-quenching of the FAM fluorophore), suggesting that the imaged reaction droplet 1300 included the target of interest and at least one agarose particle including the amplification primers.

Example 4: Forming Multiple Sets of Particles with Amplification Primers

A system for performing multiplexed PCR reactions to detect DNA from four different bacteria associated with sepsis in a sample includes at least the following: a first set of particles, a second set of particles, a third set of particles, a fourth set of particles and a reporter probe.

A first set of particles specific for *Staphylococcus aureus* bacteria is formed as follows. A solution including 500 nM each of forward and reverse primers specific to Staph ST228 gene and FluoSphere F8801 (red fluorescing 580/605 nm; from Thermo Fisher Scientific, Waltham, Mass.) in 0.5% to 3.0% low melt agarose in water at 65° C. is flowed through the center channel of a heated microfluidic device and focused by mineral oil/1% SPAN 80 (v/v) through a 14 micron nozzle to produce droplets ranging in size from 5 to 30 microns in diameter. The resulting first set of droplets are allowed to solidify by cooling for 30 minutes (and rinsed with X prior to storage in X or Y?).

A second set of particles specific for *Staphylococcus aureus* that is methicillin resistant (MRSA) bacteria is formed as follows. A solution including 500 nM each of forward and reverse primers specific to Staph mecA gene which indicates resistance to first line antibiotics and FluoSphere F8797 (blue fluorescing 350/440 nm; from Thermo Fisher Scientific) in 0.5% to 3.0% low melt agarose in water at 65° C. is flowed through the center channel of the heated microfluidic device and focused by mineral oil/1% SPAN 80 (v/v), cooled, and stored as described above with regard to the first set of particles.

A third set of particles specific for *E. coli* bacteria is formed as follows. A solution including 500 nM forward and reverse primers specific to *E. coli* rodA gene and FluoSphere F8800 (orange fluorescing 540/560 nm; from Thermo Fisher Scientific) in 0.5% to 3.0% low melt agarose in water at 65° C. is flowed through the center channel of the heated microfluidic device and focused by mineral oil/1% SPAN 80 (v/v), cooled, and stored as described above with regard to the first set of particles.

A fourth set of particles specific for *Streptococcus pneumoniae* bacteria is formed as follows. A solution including 500 nM forward and reverse primers specific to Strep lytA gene and FluoSphere F8789 (dark red fluorescing; 660/680 nm; from Thermo Fisher Scientific) in 0.5% to 3.0% low melt agarose in water at 65° C. is flowed through the center channel of the heated microfluidic device and focused by mineral oil/1% SPAN 80 (v/v) cooled, and stored as described above with regard to the first set of particles.

The reporter probe is EvaGreen (green fluorescing (498/533 nm; from Biotium, Inc., Fremont Calif.). In some embodiments, the EvaGreen is incorporated into each of the four set of particles during the formation of each set of agarose particles. In some embodiments, the EvaGreen is added during the stochastic formation of PCR reaction droplets (see below).

Example 5: Isolating DNA

DNA is isolated from a blood sample of an individual diagnosed with sepsis using standard procedures. Briefly, a small quantity of blood (e.g., 200 ul) is extracted by finger prick from the subject. A commercially available DNA extraction kit (e.g., QIAamp DNA Blood (from QIAGEN, North American Headquarters, Germantown, Md.) or a similar kit) can be used to extract DNA from the blood by treating the sample with protease or proteinase K, binding DNA to a spin column, washing, and eluting. The blood sample may be pre-treated with an additional lysis reagent (e.g., lysozyme (20 mg/ml) and/or lysostaphin (200 ug/ml)) adequate for lysing Gram-positive and difficult to lyse bacteria.

Example 6: Forming Reaction Droplets and Performing Amplification

Method of determining presence of bacterial DNA in sepsis sample with the four sets of particles includes at least the steps as follows. An aqueous solution including a plurality of each of the four sets of particles is mixed with the genomic DNA extracted from blood, the reporter probe EvaGreen and a PCR master mix including a DNA polymerase (e.g., Taq DNA Polymerase), deoxyribonucleotide triphosphates (e.g., dATP, dTTP, dGTP, and dCTP), and magnesium chloride in a buffered solution. In some embodiments, a PCR master mix including EvaGreen may be used for the purpose (from, e.g., Biotium).

Reaction droplets including the above components are generated as follows. The aqueous solution described above is added in a 1:2 ratio to an oil/surfactant mixture (e.g., mineral oil/1% SPAN 80 (v/v)) to a 1.7 mL Eppendorf tube. These immiscible fluids are vortexed with a vortex mixer (e.g., VWR analog vortex mixer (cat. #10153-838; Radnor, Pa., USA) at a maximum speed for 10-20 seconds to create a population of polydisperse droplets. Alternatively, the reaction droplets are formed using the above described aqueous solution in an automated droplet generator (from, e.g., BioRad, Hercules, Calif., USA) using a microfluidic chip and focusing with an oil/surfactant mixture.

The reaction droplets are then run in a thermocycler (e.g., a C100 or C1000 thermocycler from BioRad, Hercules, Calif.) using the following protocol: 50° C. hold for 60 minutes, 95° C. hold for 10 minutes, 40 cycles of 95° C. for 30 seconds and 60° C. for 1 minute. Fluorescence associated with fluorescent spheres and the EvaGreen is read using a fluorescent reader (e.g., QX200 Droplet Reader, BioRad) and appropriate software.

Example 7: Multiplexed Analysis of Bacteria in a Test Sample

Described is an example of a system for multiplexed analysis of bacteria in a test sample of water. The system includes a set of particles including the enzymatic substrate 4-methylumbelliferyl-β-D-glucuronide (MUG) for detecting enterobacteria (e.g., *E. coli*) and the generic cell growth marker resazurin. Methylumbelliferyl-β-D-glucuronide fluoresces blue in response to hydrolysis by β-D-glucuronide. Resazurin is a cell-permeable and non-toxic oxidation-reduction indicator which in viable cells is reduced to red fluorescing resorufin. Particles containing methylumbelliferyl-β-D-glucuronide and resazurin (both from, e.g., Sigma-Aldrich, St. Louis, Mo.) are mixed into 0.5% to 3.0% low melt agarose in water at 65° C. and flowed through a center channel of a heated microfluidic device and focused by mineral oil/1% SPAN 80 (v/v), cooled, and stored.

The test sample of water is mixed with the set of particles as well as a nutrient broth (e.g., LB broth). The aqueous solution is mixed with an immiscible carrier fluid, e.g., mineral oil to form reaction droplets. Droplets are formed with bacteria as described in Byrnes et al. *Analyst* (2018) 143:2828-2836, which is incorporated herein by reference. The droplets can be formed either by bulk emulsion using a vortex mixer or by flow-focusing using a microfluidic device as described above herein.

Example 8: Multiplexed Immunoassay Detection

Described is an example of a system for multiplexed immunoassay detection combined with DNA amplification. A first set of particles includes a polyclonal antibody specific for IL-8 protein. A second set of particles includes a polyclonal antibody specific for IL-12 protein. Polyclonal antibodies for both IL-8 and IL-12 are available from a variety of commercial sources (see, Linscott's Directory on the World Wide Web at linscottsdirectory.com for an extensive list of suppliers). Each of these polyclonal antibodies is reactive against multiple epitopes on the target proteins. The anti-IL-8 polyclonal antibody and the anti-IL-12 polyclonal antibody are modified with succinimidyl-4-[p-maleimidopheynyl]butyrate (SMPB) (from, e.g., Pierce/Thermo Fischer Scientific) using the manufacturer's instructions. A G-50 spin column is used to remove excess SMPB. An oligonucleotide pair, each modified with either a 5 prime-SH group or a 3 prime-SH group, are incubated with half each of the SMPB-modified anti-IL-8 and anti-IL-12 polyclonal antibodies to allow cross-linking of the oligonucleotides to the antibodies (see, e.g., Gullberg, et al. (2004) Proc. Natl. Acad. Sci. 101:8420-8424, which is incorporated herein by reference).

A first set of particles specific for IL-8 protein is formed as follows. A solution including the anti-IL-8 polyclonal antibodies modified with the oligonucleotide pair and FluoSphere F8801 (red fluorescing 580/605 nm; from Thermo Fisher Scientific, Waltham, Mass.) in 0.5% to 3.0% low melt agarose in water at 65° C. is flowed through the center channel of a heated microfluidic device and focused by mineral oil/1% SPAN 80 (v/v) through a 14 micron nozzle to produce droplets ranging in size from 5 to 30 microns in diameter. The resulting first set of droplets are allowed to solidify by cooling for 30 minutes.

A second set of particles specific for IL-12 protein is formed as follows. A solution including the anti-IL-12 polyclonal antibodies modified with the oligonucleotide pair and FluoSphere F8797 (blue fluorescing 350/440 nm; from Thermo Fisher Scientific) in 0.5% to 3.0% low melt agarose in water at 65° C. is flowed through the center channel of the heated microfluidic device and focused by mineral oil/1% SPAN 80 (v/v), and cooled as described above.

The reporter probe is EvaGreen (green fluorescing (498/533 nm; from Biotium, Inc., Fremont Calif.). In some embodiments, the EvaGreen is incorporated into the particles during the formation of each set of agarose particles. In some embodiments, the EvaGreen is added to the aqueous solution (see below).

The particles including the anti-IL-8 and anti-IL-12 polyclonal antibodies are mixed in an aqueous solution with EvaGreen, ligation reagents, amplification reagents, and a test sample including IL-8 and IL-12 proteins. The ligation/amplification reagents can include T4 DNA ligase, a connector oligonucleotide, dNTPs, and DNA polymerase (see, e.g., Gullberg, et al. (2004) Proc. Natl. Acad. Sci. 101:8420-8424, which is incorporated herein by reference). Aqueous-in-oil droplets are formed as described above. Ligation is carried out at room temperature followed by PCR amplification as described above. Fluorescence associated with FluoSphere 8801, FluoSphere 8797, and EvaGreen is read using a fluorescence reader.

One skilled in the art will recognize that the herein described component, devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components, devices, and objects should not be taken as limiting.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Aspects of the subject matter described herein are set out in the following numbered paragraphs:

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A system for multiplexed analysis of two or more targets in a test sample, comprising:
    two or more sets of particles including
        a first set of particles, each particle of the first set of particles degradable in response to a first environmental condition and having associated therewith a first set of one or more target-specific antibodies and a first optically detectable identifier capable of emitting a first wavelength, the first set of one or more target-specific antibodies selected to specifically interact with a first target, and the first optically detectable identifier indicative of the first set of one or more target-specific antibodies; and
        at least one second set of particles, each particle of the at least one second set of particles degradable in response to a second environmental condition and having associated therewith a second set of one or more target-specific antibodies and a second opti-cally detectable identifier capable of emitting a second wavelength, the second set of one or more target-specific antibodies selected to specifically interact with a second target, and the second optically detectable identifier indicative of the second set of one or more target-specific antibodies; and
    at least one optically detectable reporter probe capable of constitutively emitting a third wavelength in response to a reaction of the first set of one or more target-specific antibodies with the first target in the test sample and/or a reaction of the second set of one or more target-specific antibodies with the second target in the test sample, wherein the at least one optically detectable reporter probe is a separate component relative to the first set of particles and the at least one second set of particles, and wherein the at least one optically detectable reporter probe comprises a probe of cell viability capable of constitutively emitting the third wavelength in response to cell viability.

2. The system of claim 1, wherein the particles of the first set of particles and of the at least one second set of particles include a structure at least partially formed from a hydrophilic material and degradable in response to at least a first temperature condition or a second temperature condition, wherein at least a portion of the particles of the first set of particles and of the at least one second set of particles are distributable into an aqueous portion of an aqueous-in-oil droplet.

3. The system of claim 1, wherein the first wavelength emitted by the first optically detectable identifier is a first detectable color, the second wavelength emitted by the second optically detectable identifier is a second detectable color, and the third wavelength constitutively emitted by the at least one optically detectable reporter probe is a third detectable color; and wherein the first wavelength, the second wavelength, and the third wavelength are optically discernable from one another.

4. The system of claim 1, wherein the first optically detectable identifier includes a first fluorophore capable of emitting fluorescence at the first wavelength and the second optically detectable identifier includes a second fluorophore capable of emitting fluorescence at the second wavelength; and wherein the at least one optically detectable reporter probe comprises a fluorescent DNA intercalating agent capable of constitutively emitting the third wavelength.

5. The system of claim 1, wherein the one or more target-specific antibodies in the first set of one or more target-specific antibodies and in the second set of one or more target-specific antibodies recognize bacteriophage.

* * * * *